(12) United States Patent
Conzen et al.

(10) Patent No.: US 12,062,444 B2
(45) Date of Patent: Aug. 13, 2024

(54) METHODS AND COMPOSITIONS RELATED TO TRIPLE-NEGATIVE BREAST CANCER

(71) Applicant: THE UNIVERSITY OF CHICAGO, Chicago, IL (US)

(72) Inventors: Suzanne Conzen, Chicago, IL (US); Lei Huang, Chicago, IL (US); Maria Kocherginsky, Chicago, IL (US); Diana Szymanski, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1527 days.

(21) Appl. No.: 16/217,350

(22) Filed: Dec. 12, 2018

(65) Prior Publication Data

US 2019/0279769 A1 Sep. 12, 2019

Related U.S. Application Data

(60) Provisional application No. 62/597,534, filed on Dec. 12, 2017.

(51) Int. Cl.
| | |
|---|---|
| G16H 50/20 | (2018.01) |
| C12Q 1/6809 | (2018.01) |
| C12Q 1/6827 | (2018.01) |
| C12Q 1/6837 | (2018.01) |
| C12Q 1/6886 | (2018.01) |
| G16H 50/30 | (2018.01) |

(52) U.S. Cl.
CPC .......... *G16H 50/20* (2018.01); *C12Q 1/6809* (2013.01); *C12Q 1/6827* (2013.01); *C12Q 1/6837* (2013.01); *C12Q 1/6886* (2013.01); *G16H 50/30* (2018.01); *C12Q 2600/106* (2013.01); *C12Q 2600/112* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2016/0289261 A1   10/2016   Arora et al.

OTHER PUBLICATIONS

Stavraka et al., "The La-Related Proteins, a Family with Connections to Cancer" 5 Biomolecules 2701-2722 (Year: 2015).*
Armakolas et al., "Subdivision of molecularly-classified groups by new gene signatures in breast cancer patients" 28 Oncology Reports 2255-2263 (Year: 2012).*
Kota et al., "SUMO-Modification of the La Protein Facilitates Binding to mRNA In Vitro and in Cells" 11(5) PLoS One e0156365 1-19 (Year: 2016).*
Abduljabbar et al., "Clinical and biological significance of glucocorticoid receptor (GR) expression in breast cancer." *Breast Cancer Res Treat* 2015, 150, 335-346.
Balko et al., "Molecular profiling of the residual disease of triple-negative breast cancers after neoadjuvant chemotherapy identifies actionable therapeutic targets." *Cancer Discov* 2014, 4, 232-245.
Balko et al., "Triple-negative breast cancers with amplification of JAK2 at the 9p24 locus demonstrate JAK2-specific dependence" *Sci Transl Med* 2016, 8, 334ra353.
Barton et al., "Multiple molecular subtypes of triple-negative breast cancer critically rely on androgen receptor and respond to enzalutamide in vivo." *Mol Cancer Ther* 2015,14, 769-778.
Bauer et al., "RNA interference (RNAi) screening approach identifies agents that enhance paclitaxel activity in breast cancer cells." Breast Cancer Res 2010, 12, R41, 16 pages.
Bhola et al., "Treatment of Triple-Negative Breast Cancer with TORC1/2 Inhibitors Sustains a Drug-Resistant and Notch-Dependent Cancer Stem Cell Population." *Cancer Res* 2016, 76, 440-452.
Chodankar et al., "Hic-5 is a transcription coregulator that acts before and/or after glucocorticoid receptor genome occupancy in a gene-selective manner." *Proc Natl Acad Sci USA* 2014, 111, 4007-4012.
Clark et al., "1H-Pyrazolo[3,4-g]hexahydro-isoquinolines as selective glucocorticoid receptor antagonists with high functional activity." *Bioorg Med Chem Lett* 2008, 18, 1312-1317.
Clark, "Glucocorticoid Receptor Antagonists" *Current Topics in Medicinal Chemistry* 2008, 8(9), 813-838.
Craig et al., "Genome and transcriptome sequencing in prospective metastatic triple-negative breast cancer uncovers therapeutic vulnerabilities." *Mol Cancer Ther* 2013, 12, 104-116.
Creighton et al., "A gene transcription signature associated with hormone independence in a subset of both breast and prostate cancers." *BMC Genomics* 2007, 8, 199, 11 pages.
De Bosscher et al., "A fully dissociated compound of plant origin for inflammatory gene repression." *Proc Natl Acad Sci USA* 2005, 102, 15827-15832.
Desmet et al., "Compound A influences gene regulation of the Dexamethasone-activated glucocorticoid receptor by alternative cofactor recruitment" *Scientific Reports* 2017, 7(8063), 14 pages.
Evans et al., "The steroid and thyroid hormone receptor superfamily" *Science* 1988, 240 (4854), 889-895.
Galliher-Beckley et al., "Ligand-independent phosphorylation of the glucocorticoid receptor integrates cellular stress pathways with nuclear receptor signaling." *Mol Cell Biol* 2011, 31, 4663-4675.
Glass et al., "The coregulator exchange in transcriptional functions of nuclear receptors." *Genes Dev* 2000, 14, 121-141.
Goecks et al., "Galaxy: a comprehensive approach for supporting accessible, reproducible, and transparent computational research in the life sciences." *Genome Biol* 2010, 11(R86), 13 pages.
Gonzalez-Angulo et al., "Androgen receptor levels and association with PIK3CA mutations and prognosis in breast cancer." *Clin Cancer Res* 2009, 15, 2472-2478.

(Continued)

*Primary Examiner* — Nancy J Leith
(74) *Attorney, Agent, or Firm* — Norton Rose Fulbright US LLP

(57) ABSTRACT

Embodiments are directed to kits and methods of treating a breast cancer patient with a glucocorticoid receptor antagonist with or without an anticancer agent or compound after the patient has been determined to be susceptible to treatment with the glucocorticoid receptor antagonist.

15 Claims, 24 Drawing Sheets
Specification includes a Sequence Listing.

(56) References Cited

OTHER PUBLICATIONS

Goyeneche et al., "Mifepristone inhibits ovarian cancer cell growth in vitro and in vivo." *Clin Cancer Res* 2007, 13, 3370-3379.
Gucalp et al., "Phase II trial of bicalutamide in patients with androgen receptor-positive, estrogen receptor-negative metastatic Breast Cancer." *Clin Cancer Res* 2013, 19, 5505-5512.
Gyorffy et al "An online survival analysis tool to rapidly assess the effect of 22,277 genes on breast cancer prognosis using microarray data of 1,809 patients." *Breast Cancer Res Treat* 2010, 123, 725-731.
Herr et al., "Glucocorticoid cotreatment induces apoptosis resistance toward cancer therapy in carcinomas." *Cancer Res* 2003, 63, 3112-3120.
Hsu et al., "Genome-wide analysis of three-way interplay among gene expression, cancer cell invasion and anti-cancer compound sensitivity" *BMC Med* 2013, 11, 106, 14 pages.
Huang et al., "The mechanisms and significance of up-regulation of RhoB expression by hypoxia and glucocorticoid in rat lung and A549 cells." *J Cell Mol Med* 2016, 20, 1276-1286.
Hunt et al., "Discovery of a novel non-steroidal GR antagonist with in vivo efficacy in the olanzapine-induced weight gain model in the rat." *Bioorg Med Chem Lett* 2012, 22, 7376-7380.
Hunt et al., "Identification of the Clinical Candidate (R)-(1-(4-Fluorophenyl)-6-((1-methyl-1 H-pyrazol-4-yl)sulfonyl)-4,4a,5,6,7,8-hexahydro-1H-pyrazolo[3,4-g]isoquinolin-4a-yl) (4-(trifluoromethyl)pyridin-2-yl)methanone (CORT125134): A Selective Glucocorticoid Receptor (GR) Antagonist" *J. Med. Chem.* 2017, 60, 8, 3405-3421.
Isikbay et al., "Glucocorticoid receptor activity contributes to resistance to androgen-targeted therapy in prostate cancer." *Horm Cancer* 2014, 5, 72-89.
Jiang et al., "Mechanisms of energy restriction: effects of corticosterone on cell growth, cell cycle machinery, and apoptosis." *Cancer Res* 2002, 62, 5280-5287.
Jozwik et al., "Pioneer factors in hormone-dependent cancers." *Nat Rev Cancer* 2012, 12, 381-385.
Kanaan et al., "Metabolic profile of triple-negative breast cancer in African-American women reveals potential biomarkers of aggressive disease." *Cancer Genomics Proteomics* 2014, 11, 279-294.
Kesselring et al., "IRAK-M Expression in Tumor Cells Supports Colorectal Cancer Progression through Reduction of Antimicrobial Defense and Stabilization of STAT3." *Cancer Cell* 2016, 29, 684-696.
Kroon et al., "Glucocorticoid receptor antagonism reverts docetaxel resistance in human prostate cancer." *Endocr Relat Cancer* 2016, 23, 35-45.
Lawrence et al., "The proteomic landscape of triple-negative breast cancer." *Cell Rep* 2015, 11, 630-644.
Leehy et al., "Modifications to glucocorticoid and progesterone receptors alter cell fate in breast cancer." *J Mol Endocrinol* 2016, 56, R99-R114.
Lefstin et al., "Allosteric effects of DNA on transcriptional regulators." *Nature* 1998, 392, 885-888.
Lehmann et al., "Identification of human triple-negative breast cancer subtypes and preclinical models for selection of targeted therapies." *J Clin Invest* 2011, 121, 2750-2767.
Lehmann et al., "Refinement of Triple-Negative Breast Cancer Molecular Subtypes: Implications for Neoadjuvant Chemotherapy Selection" *PLoS One* 2016, 11(e0157368), 22 pages.
Lesovaya et al., "Discovery of Compound A—a selective activator of the glucocorticoid receptor with anti-inflammatory and anti-cancer activity" *Oncotarget.* 2015, 6(31), 30730-30744.
Love et al., "Role of the chromatin landscape and sequence in determining cell type-specific genomic glucocorticoid receptor binding and gene regulation." *Nucleic Acids Res* 2017, 45, 1805-1819.
Luz et al., "Indole Glucocorticoid Receptor Antagonists Active in a Model of Dyslipidemia Act via a Unique Association with an Agonist Binding Site." *J. Med. Chem.* 2015, 58, 16, 6607-6618.

Melhem et al., "Administration of Glucocorticoids to Ovarian Cancer Patients is Associated with Expression of the Anti-apoptotic Genes SGK1 and MKP1/DUSP1 in OvarianTissues" *Clin Cancer Res* 2009,15(9), 3196-3204.
Mihaly et al., "A meta-analysis of gene expression-based biomarkers predicting outcome after tamoxifen treatment in breast cancer." *Breast Cancer Res Treat* 2013, 140, 219-232.
Mikosz et al., "Glucocorticoid Receptor-mediated Protection from Apoptosis is Associated with Induction of the Serine/Threonine Survival Kinase Gene, sgk-1" *JBC* 2001, 276(20), 16649-16654.
Mohler et al., "Non-steroidal glucocorticoid receptor antagonists: the race to replace RU-486 for anti-glucocorticoid therapy" *Expert Opin. Ther. Patents* 2007, 17(1), 59-81.
Moran et al., "The glucocorticoid receptor mediates a survival signal in human mammary epithelial cells." *Cancer Res* 2000, 60, 867-872.
Nanda et al., "A randomized phase I trial of nanoparticle albumin-bound paclitaxel with or without mifepristone for advanced breast cancer." *Springerplus* 2016, 5(947), 9 pages.
Nguyen et al., "A mixed glucocorticoid/mineralocorticoid receptor modulator dampens endocrine and hippocampal stress responsivity in male rats." *Physiol Behav* 2017, 178, 82-92.
Pan et al., "Activation of the glucocorticoid receptor is associated with poor prognosis in estrogen receptor-negative breast cancer." *Cancer Res* 2011, 71, 6360-6370.
Pang et al., "Role of Resistin in Inflammation and Inflammation-Related Diseases" *Cell Mol Immunol* 2006, 3(1), 29-34.
Regan Anderson et al., "Breast Tumor Kinase (Brk/PTK6) Is Induced by HIF, Glucocorticoid Receptor, and PELP1-Mediated Stress Signaling in Triple-Negative Breast Cancer." *Cancer Res* 2016, 76, 1653-1663.
Shang et al., "Formation of the androgen receptor transcription complex" *Mol Cell* 2002, 9, 601-610.
Skor et al., "Glucocorticoid receptor antagonism as a novel therapy for triple-negative breast cancer." *Clin Cancer Res* 2013, 19, 6163-6172.
Sparano et al., "Prospective Validation of a 21-Gene Expression Assay in Breast Cancer." *N Engl J Med* 2015, 373, 2005-2014.
Stringer-Reasor et al., "Glucocorticoid receptor activation inhibits chemotherapy-induced cell death in high-grade serous ovarian carcinoma." *Gynecol Oncol* 2015, 138, 656-662.
Sundahl et al., "Selective glucocorticoid receptor modulation: New directions with non-steroidal scaffolds" *Pharmacology & Therapeutics* 2015, 152, 28-41.
Szász et al., "Cross-validation of survival associated biomarkers in gastric cancer using transcriptomic data of 1,065 patients." *Oncotarget* 2016, 7, 49322-49333.
The Cancer Genome Atlas Network, "Comprehensive molecular portraits of human breast tumours." *Nature* 2012, 490, 61-70.
Veneris et al., "High glucocorticoid receptor expression predicts short progression-free survival in ovarian cancer." *Gynecol Oncol* 2017, 146, 153-160.
Voronov et al., "IL-1 is required for tumor invasiveness and angiogenesis." *Proc Natl Acad Sci USA* 2003, 100, 2645-2650.
Weikum et al., "Glucocorticoid receptor control of transcription: precision and plasticity via allostery." *Nat Rev Mol Cell Biol* 2017, 18, 159-174.
West et al., "GR and ER Coactivation Alters the Expression of Differentiation Genes and Associates with Improved ER+ Breast Cancer Outcome." *Mol Cancer Res* 2016, 14, 707-719.
Wolf et al., "Coactivators and nuclear receptor transactivation." *J Cell Biochem* 2008, 104, 1580-1586.
Wu et al., "Microarray analysis reveals glucocorticoid-regulated survival genes that are associated with inhibition of apoptosis in breast epithelial cells." *Cancer Res* 2004, 64, 1757-1764.
Yang et al., "Dexamethasone decreases hepatocellular carcinoma cell sensitivity to cisplatin-induced apoptosis." *Hepatogastroenterology* 2011, 58, 1730-1735.
Zeitzer et al., "Correspondence of plasma and salivary cortisol patterns in women with breast cancer." *Neuroendocrinology* 2014, 100, 153-161.

(56) References Cited

OTHER PUBLICATIONS

Zhang et al., "Glucocorticoid-mediated inhibition of chemotherapy in ovarian carcinomas." *Int J Oncol* 2006, 28, 551-558.

\* cited by examiner

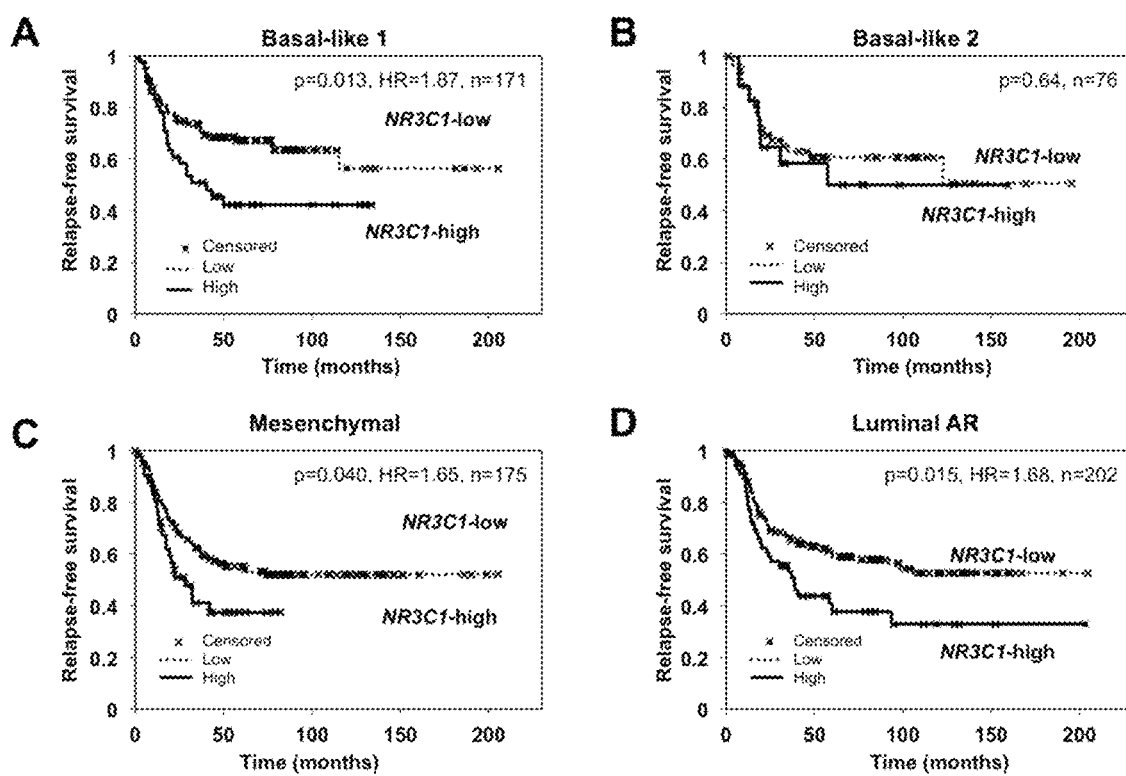
FIG. 1A-D

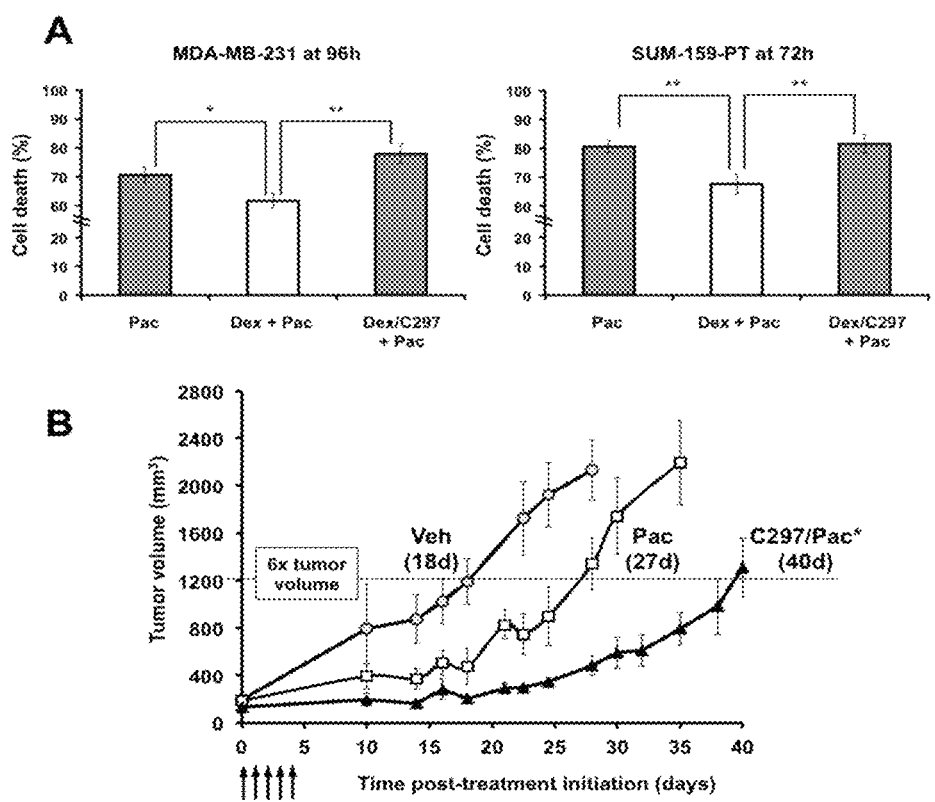
FIG. 2A-B

A
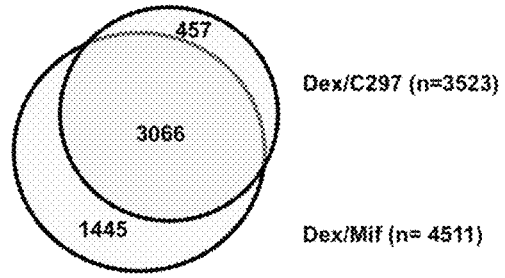
B  GR-mediated genes reversed 25% by antagonism (Mif or C297)
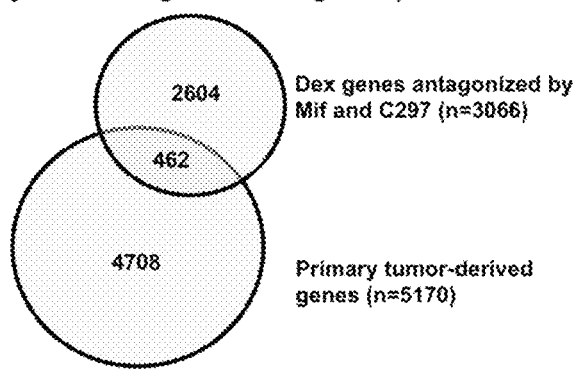
C  Commonly differentially expressed genes (from above) and primary tumor GR-high vs. GR-low gene expression
FIG. 3A-C

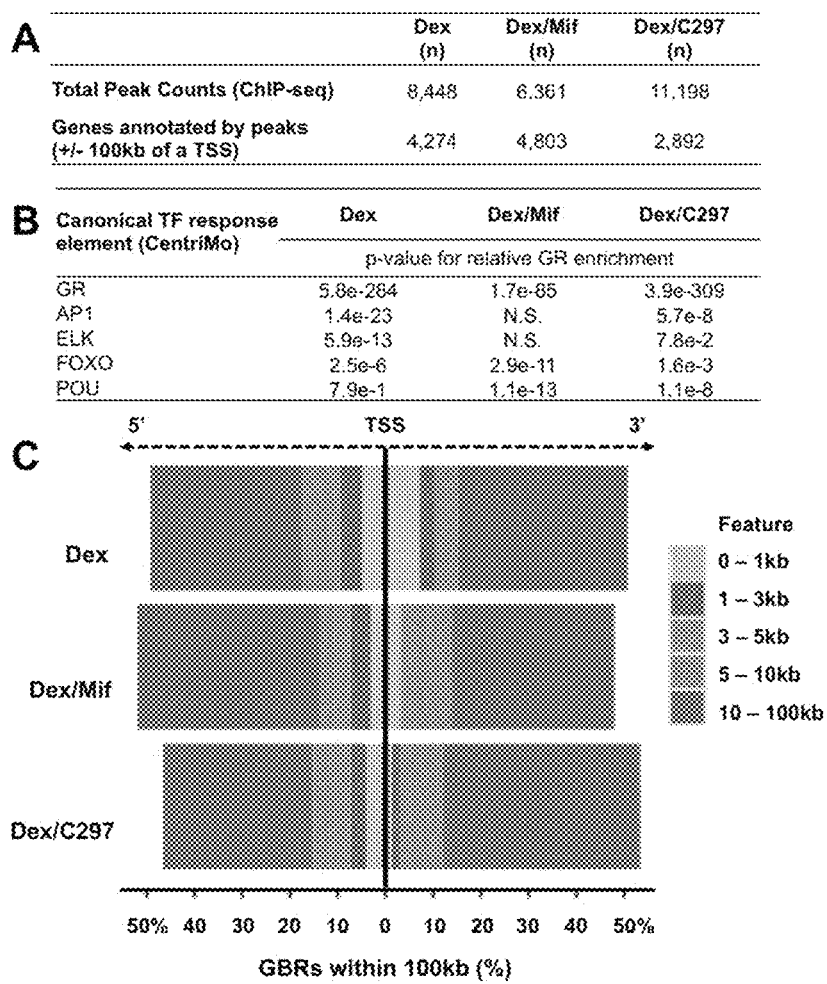
FIG. 4A-C

A

| | Total Genes (n) | Dex-upregulated (n) | Dex-downregulated (n) |
|---|---|---|---|
| GRsig | 74 | 46 | 28 |
| Subset with Dex GBRs +/- 100 kb | 31 | 17 | 14 |
| Subset with Dex GBRs lost with Mif or C297 | 28 | 15 | 13 |

B GRsig genes (n=74)
Bold genes indicate GBR within +/- 100 kb of the gene TSS Dex-upregulated genes with HR ≥ 1.5 in Discovery cohort:
ABHD5, ACSL3, AP1AR, ASMTL, ATP2B1, BBS10, BCOR, C12orf29, CCT6A, CDK7, CHMP2B, CRY1, CUL4A, DDX18, DLAT, EIF3J, ETF1, F2R, HEATR3, HOMER1, HPS5, HSPA9, IMPACT, IPO7, KCTD3, LYPLA1, NAP1L1, NOL11, PEX3, PGRMC2, PLCB4, PRPF39, RABGGTB, RMND1, RPL31, SEH1L, SERP1, SPATA5L1, SSB, TCEB1, TSEN2, USE1, UTP14A, WDR43, WNT5A, ZNF189

Dex-downregulated genes with HR ≤ 0.5 in Discovery cohort:
CACNA1G, CDKN2D, COL4A6, COL7A1, CORO2B, CPNE6, DLG4, FGF5, GLI2, GRM5, GRM6, IQCC, KISS1, LMNA, MAPRE2, MAS1, MUC5AC, NOX5, POLQ, RRH, SCN3B, SERPIND1, SLC4A4, SSBP3, SYT1, TBXA2R, TROAP, TYRO3

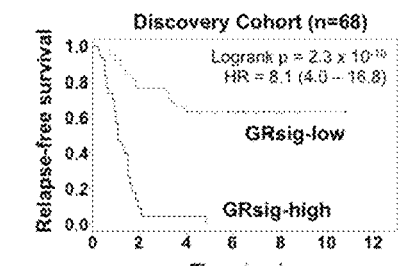
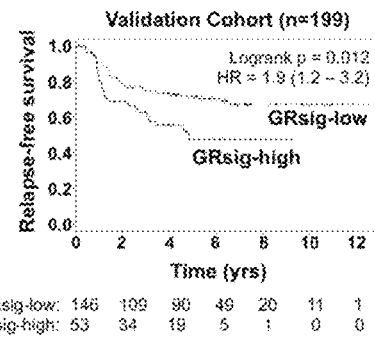

FIG. 6A-D

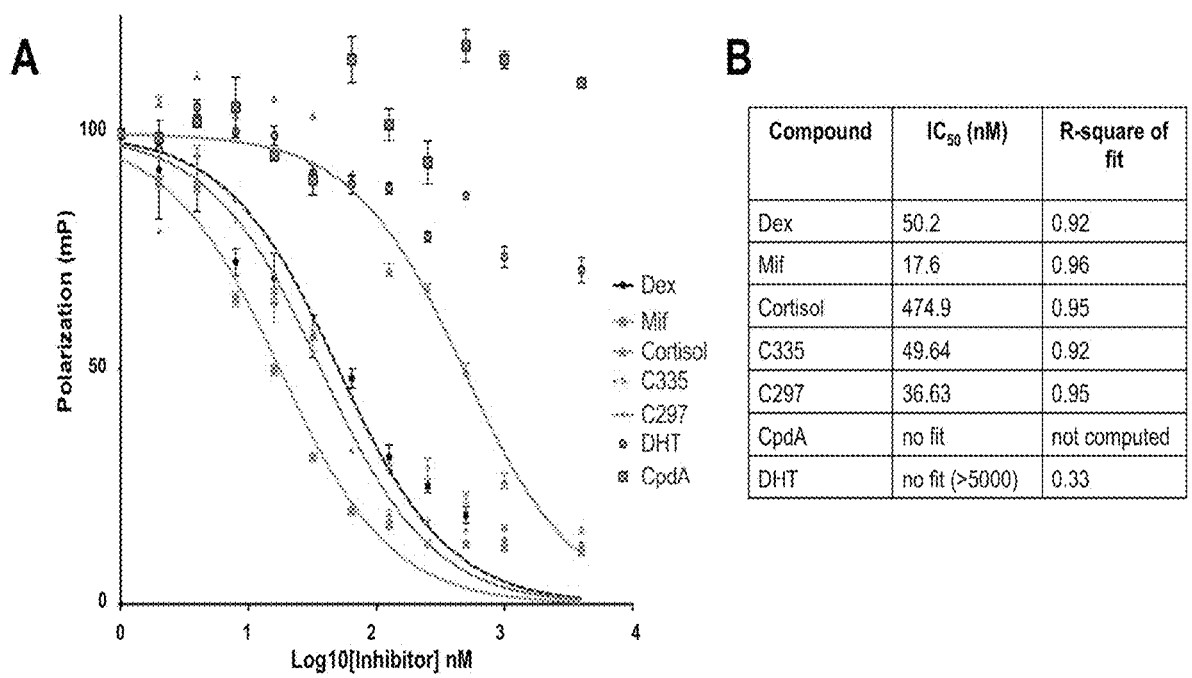
FIG. 7A-B

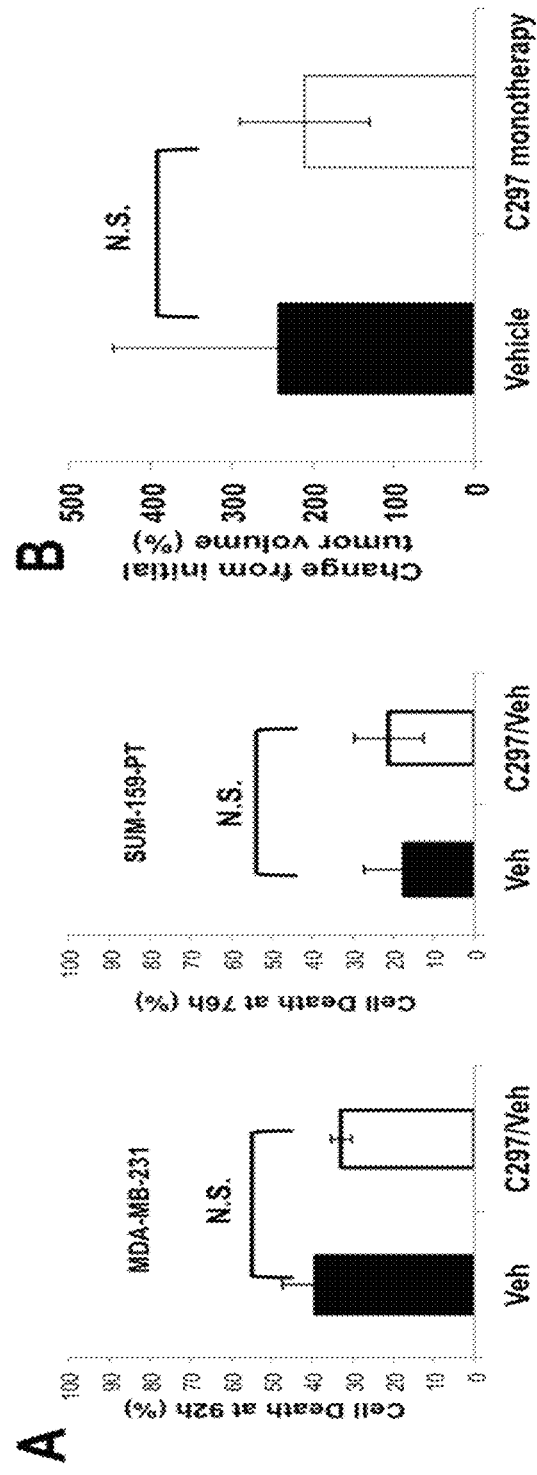
FIG. 8A-B

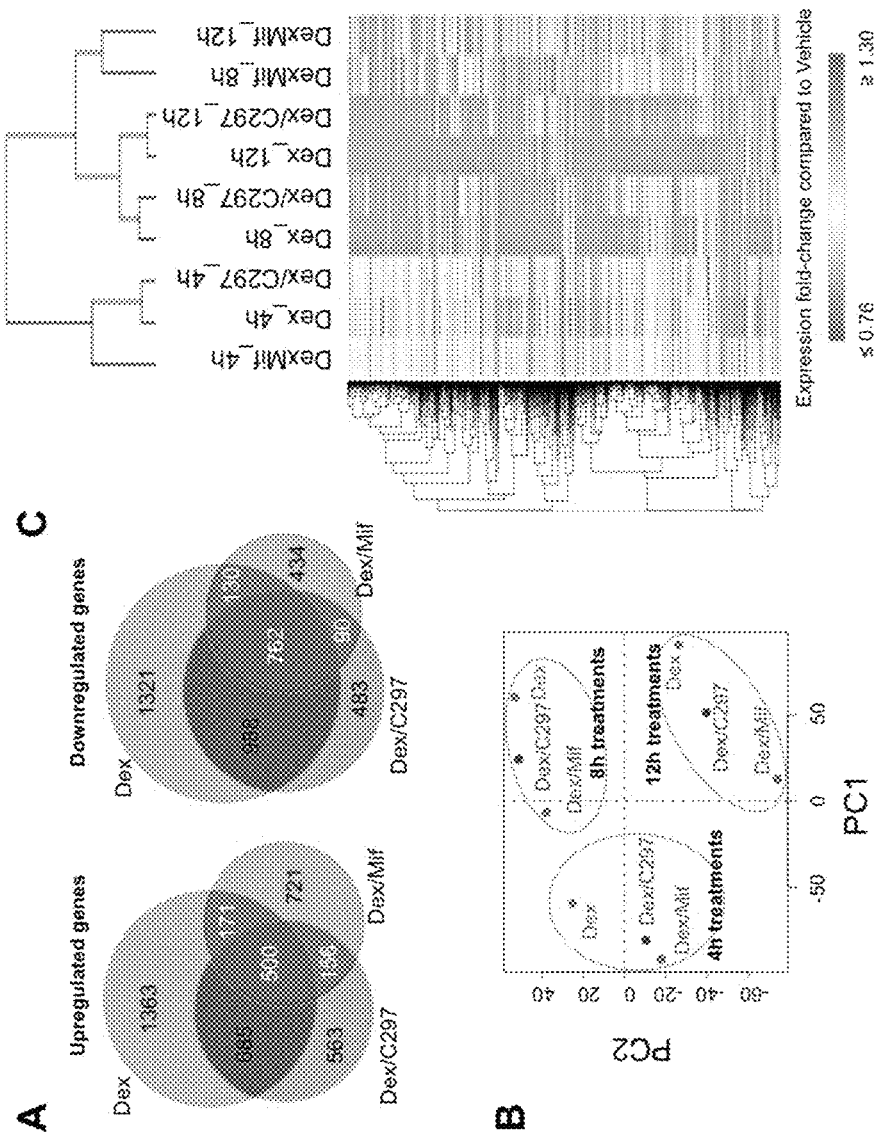
FIG. 9A-C

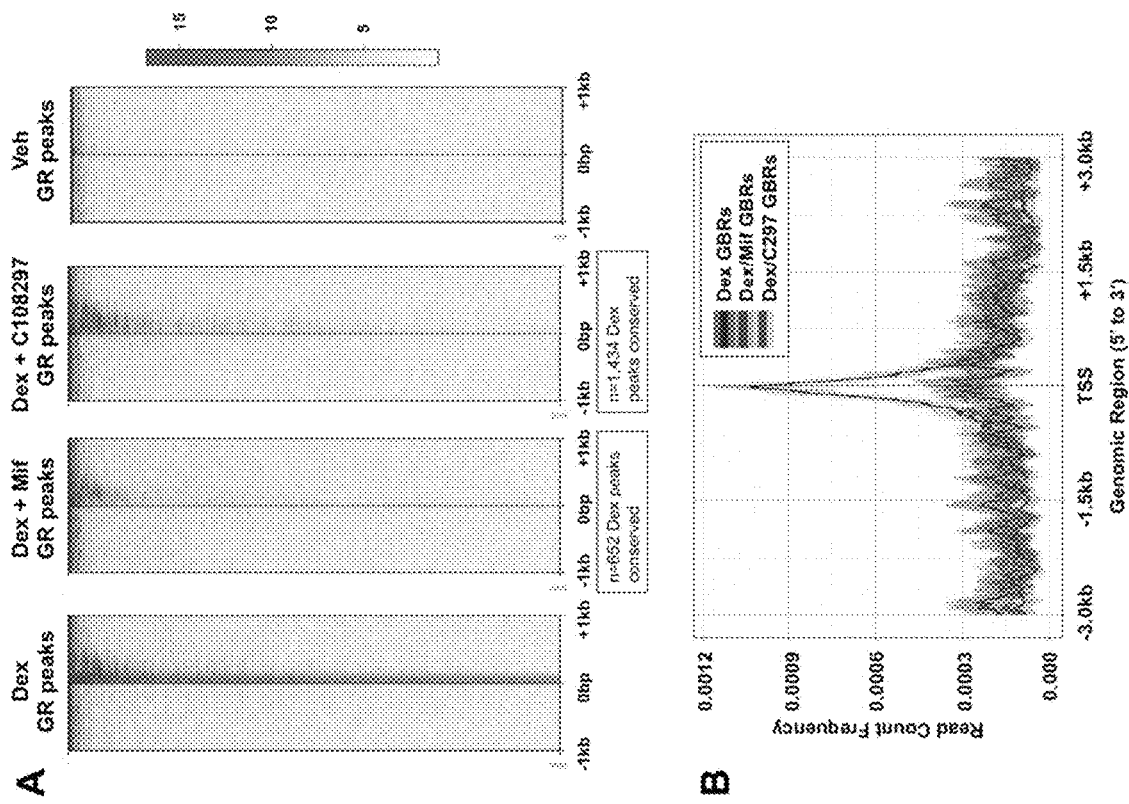
FIG. 10A-B

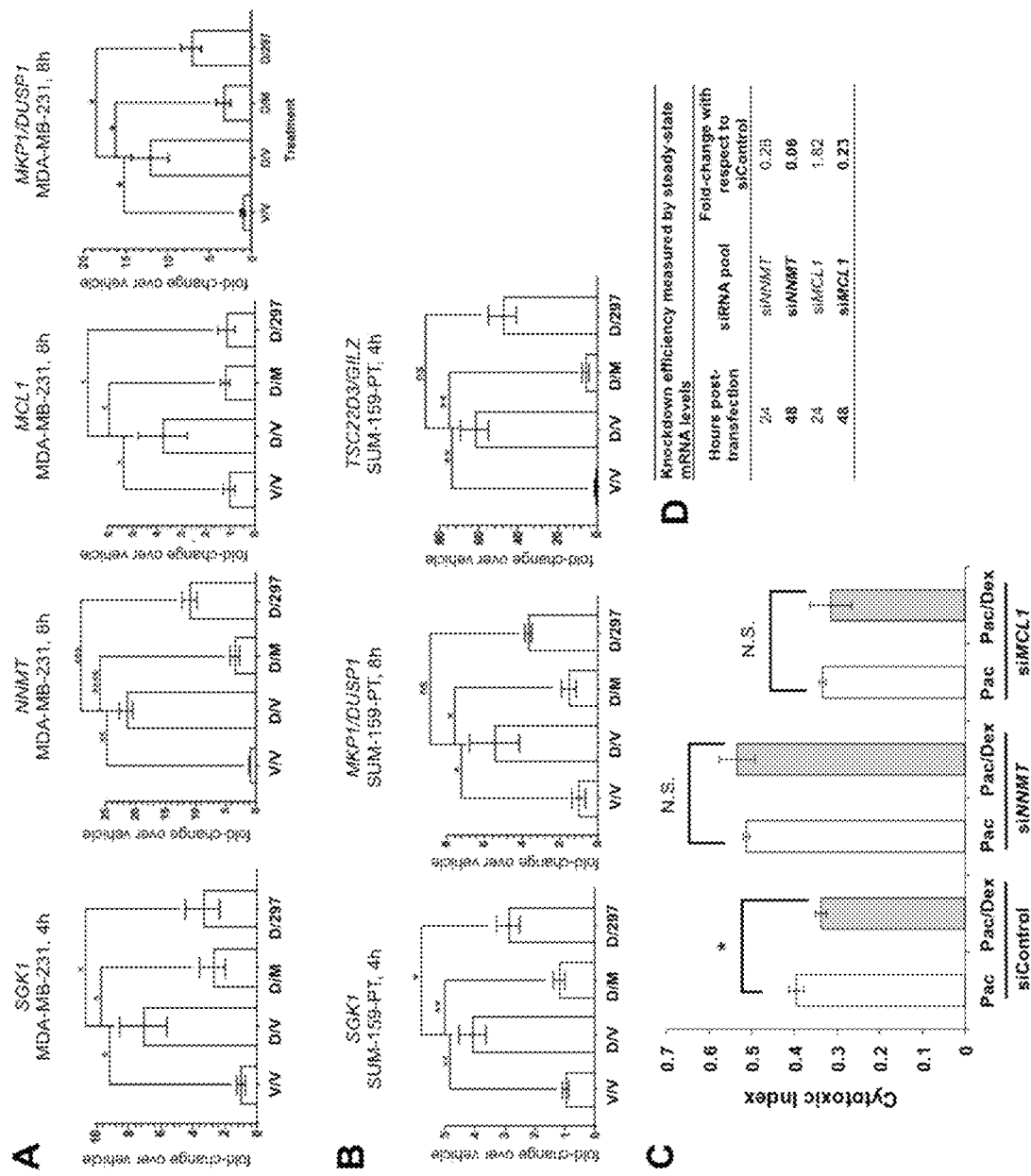
FIG. 11A-D

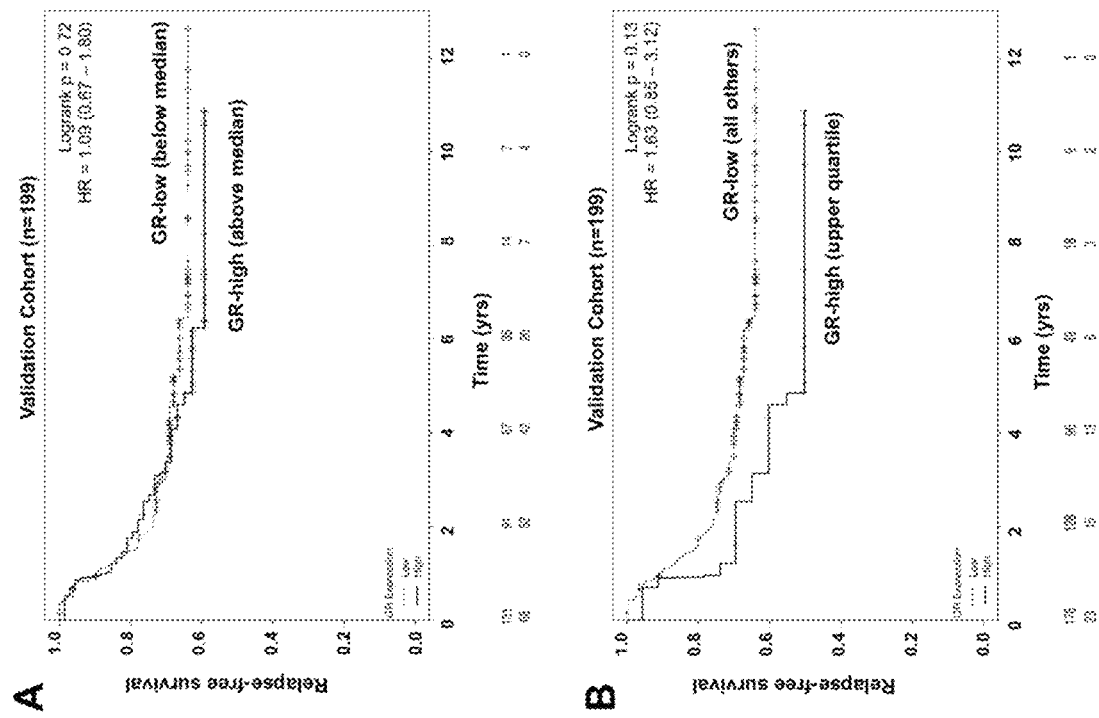
FIG. 12A-B

Table 1. GR antagonists diminish cell survival and invasive functions while promoting apoptosis

| Cell function | Activation Z-score | | | Treatment time (hr) | Number of genes (n) |
|---|---|---|---|---|---|
| | Dex | DexMif | Dex297 | | |
| synthesis of lipid (GR metabolism) | 1.91 | 0.68 | 0.83 | 4 | 46 |
| inflammatory response | 0.80 | -0.72 | 1.39 | 4 | 54 |
| invasion of tumor cell lines | 0.63 | -0.03 | 0.35 | 4 | 53 |
| colony formation of tumor cell lines (invasion) | 0.14 | 0.02 | -0.52 | 4 | 24 |
| epithelial-mesenchymal transition of breast cell lines | 0.11 | -0.34 | -0.22 | 4 | 9 |
| metastasis of tumor cell lines | 2.05 | 1.03 | 1.22 | 8 | 16 |
| transactivation | 1.62 | -0.44 | -0.28 | 8 | 39 |
| cell survival | 1.53 | -1.28 | 0.69 | 8 | 99 |
| cell proliferation of colorectal cancer cell lines | 0.72 | -1.23 | -0.71 | 8 | 27 |
| cell transformation | 0.22 | 1.86 | 1.29 | 8 | 42 |
| invasion of tumor cells | 1.46 | 0.26 | 0.29 | 12 | 15 |
| growth of tumor | 0.77 | 0.47 | 0.24 | 12 | 63 |
| growth of blood vessel | 0.44 | -0.44 | 0.22 | 12 | 10 |
| cell death of tumor cells | 1.57 | -0.55 | -0.30 | 4 | 35 |
| cytostasis of tumor cell lines | 1.80 | 0.77 | 1.03 | 4 | 15 |
| contact growth inhibition of tumor cell lines | 1.77 | 0.09 | 0.52 | 4 | 13 |
| benign neoplasia | 1.72 | -0.03 | 1.40 | 4 | 63 |
| inflammatory response | -0.14 | 1.72 | 1.34 | 8 | 54 |
| cytostasis of tumor cell lines | 1.01 | -0.45 | 0.35 | 8 | 15 |
| contact growth inhibition of tumor cell lines | 1.02 | -0.39 | 0.51 | 8 | 13 |
| apoptosis | -1.00 | 0.41 | 1.11 | 8 | 162 |
| cell death | -1.00 | 0.45 | 0.26 | 8 | 193 |
| development of epithelial tissue (differentiation) | -1.92 | 0.19 | 1.32 | 12 | 45 | inactivated ▓▓▓ activated pathway activation scale

FIG. 13

| Discovery Cohort (N=86) GEO ID | Validation Cohort (N=199) GEO ID |
|---|---|
| GSE12276 | GSE1456 |
| GSE2603 | GSE17907 |
| | GSE19615 |
| | GSE21653 |
| | GSE31519 |
| | GSE3494 |
| | GSE37946 |
| | GSE45255 |
| | GSE4611 |
| | GSE5327 |

FIG. 14

| GRsig gene | Best Affymetrix ProbeID | GRsig gene | Best Affymetrix ProbeID |
|---|---|---|---|
| ABHD5 | 213935_at | KISS1 | 205563_at |
| ACSL3 | 201661_s_at | LMNA | 212089_at |
| AP1AR | 219323_at | LYPLA1 | 212449_s_at |
| ASMTL | 36553_at | MAPRE2 | 213439_at |
| ATP2B1 | 212836_at | MAST1 | 208310_at |
| BEGIN | 219487_at | MUC5AC | 214385_at |
| BCOR | 219433_at | NAP1L3 | 208754_s_at |
| C12orf29 | 213701_at | NOL11 | 221970_s_at |
| CACNA1G | 207869_s_at | NOX5 | 220641_at |
| CC76A | 201326_at | PEX3 | 203370_s_at |
| CDK7 | 211297_s_at | PGRMC2 | 213227_at |
| CDKN20 | 210246_s_at | PLCB4 | 203896_s_at |
| CHMP2B | 202536_at | POLQ | 219510_at |
| COL4A6 | 213992_at | PRPF39 | 220533_s_at |
| COL7A1 | 204136_at | RABGGTB | 213704_at |
| CORO2B | 209789_at | RMND1 | 220329_s_at |
| CPNE6 | 210408_s_at | RPL31 | 221583_s_at |
| CRY1 | 209674_at | PRH | 208314_at |
| CUL4A | 201423_s_at | SCN3B | 204723_at |
| DDX18 | 208896_at | SEH1L | 221931_s_at |
| DLAT | 213149_at | SERP1 | 200969_at |
| DLG4 | 204592_at | SERPIND1 | 205576_at |
| EIF2J | 208264_s_at | SLC4A4 | 203908_at |
| ETP1 | 201573_at | SPATA5L1 | 222163_s_at |
| F2R | 203989_x_at | SS8 | 201139_s_at |
| FGF5 | 210311_at | SSBP3 | 217991_x_at |
| GLI2 | 207034_s_at | SYT1 | 203999_at |
| GRM5 | 214217_at | TBKA2R | 336_at |
| GRM6 | 208335_at | TCEB1 | 202823_at |
| HEATR3 | 219289_at | TROAP | 204649_at |
| HOMER1 | 213793_s_at | TSEN2 | 219581_at |
| HPS5 | 204544_at | TYRO3 | 211432_s_at |
| HSPA9 | 200690_at | USE1 | 219348_at |
| IMPACT | 218637_at | UTP14A | 221514_at |
| IPO7 | 200995_at | WDR43 | 214862_at |
| IOCC | 206650_at | WNT5A | 213425_at |
| KCTD5 | 217894_at | ZNF189 | 207513_s_at |

| Putative GR target genes (from among the 462 genes) | Direction of Dex-mediated gene expression | Promoter region | | | Dex (3.1 - 100kb +/- TSS) | Enhancer region | |
|---|---|---|---|---|---|---|---|
| | | Dex (< 3kb +/- TSS) | Dex/Mif (< 3kb +/- TSS) | Dex/297 (< 3kb +/- TSS) | | Dex/Mif (3.1 - 100kb +/- TSS) | Dex/297 (3.1 - 100kb +/- TSS) |
| ABHD5 | upregulated | | | | 1 | lost(1), gain(1) | lost(1), gain(1) |
| ACAA2 | downregulated | | lost(1) | | 1 | lost(1) | lost(1) |
| ACSL1 | upregulated | 1 | lost(1) | lost(1) | 2 | lost(2) | lost(1), conserved(1), gain(1) |
| ADAMTS12 | downregulated | 1 | lost(1) | lost(1) | 5 | lost(3), gain(3) | lost(3), gain(7) |
| ADAMTS6 | downregulated | 1 | lost(1), gain(1) | | 3 | lost(3), gain(2) | |
| AGPAT5 | upregulated | | | | 1 | lost(1) | lost(1) |
| ALCAM | upregulated | | | | 1 | lost(1) | conserved(1) |
| AMMECR1 | upregulated | | | | 2 | lost(2) | lost(2), gain(2) |
| ANGEL2 | upregulated | 1 | lost(1) | lost(1), gain(1) | | | |
| ANK2 | upregulated | | | | 1 | lost(1) | lost(1) |
| APOOL | upregulated | | | | 1 | lost(1) | lost(1), gain(2) |
| ARIH2 | upregulated | | | | 1 | lost(1) | lost(1) |
| ARMC8 | upregulated | 1 | conserved(1) | conserved(1) | | | |
| ATP2B1 | upregulated | | | | 1 | lost(1) | lost(1) |
| B3GALT5 | downregulated | 1 | lost(1) | lost(1) | | | |
| BBS10 | upregulated | | | | 1 | conserved(1) | conserved(1) |
| BCL3 | downregulated | | | | 2 | lost(2) | lost(2) |
| BCLAF1 | upregulated | 1 | lost(1) | lost(1) | | | |
| BIRC3 | upregulated | 1 | lost(1) | lost(1) | 4 | lost(3), conserved(1), gain(1) | conserved(4), gain(3) |
| BIRC5 | downregulated | 1 | lost(1) | lost(1) | 8 | lost(8), gain(10) | lost(8), gain(11) |
| BPTF | upregulated | | | | 2 | lost(2), gain(6) | lost(1), conserved(1), gain(10) |
| BRWD1 | upregulated | | | | 1 | lost(1) | lost(1) |
| C10orf10 | upregulated | | | | 1 | conserved(1) | conserved(1) |
| C1QTNF3 | upregulated | | | | 4 | lost(3), conserved(1) | lost(4), gain(3) |
| CACNA1G | downregulated | | | | 6 | lost(6), gain(3) | lost(3), conserved(3), gain(7) |

FIG. 16 (Continued)

| | | | | | |
|---|---|---|---|---|---|
| CALD1 | upregulated | | | gain(1) | |
| CAMK4 | downregulated | lost(1) | conserved(1) | 1 lost(1) | lost(1) |
| CARD10 | downregulated | | | 1 lost(1) | lost(1) |
| CAV2 | upregulated | | | 2 lost(2) | lost(1), conserved(1) |
| CBL | downregulated | | | 1 lost(1),gain(1) | conserved(1) |
| CCDC6 | upregulated | | | 1 lost(1) | lost(1),gain(1) |
| CCT6A | upregulated | | | 1 lost(1) | lost(1) |
| CDKL2 | downregulated | | | 2 lost(2),gain(1) | lost(2) |
| CDKN1C | upregulated | | | 2 lost(2), gain(1) | lost(1),conserved(1),gain(2) |
| CDKN2D | downregulated | lost(1) | lost(1) | 2 lost(2) | lost(2) |
| CHN2 | downregulated | | | 1 lost(1) | lost(1) |
| COL1A1 | downregulated | lost(1) | lost(1) | 5 lost(5), gain(3) | lost(5), gain(10) |
| COL4A6 | downregulated | lost(1) | lost(1) | | gain(1) |
| COL7A1 | downregulated | | | 2 lost(1),conserved(1) | conserved(1) |
| COPS2 | upregulated | | | 1 lost(1) | lost(1) |
| COPS8 | upregulated | | | 4 lost(3), conserved(1) | lost(3), conserved(1) |
| COX15 | upregulated | | | 3 lost(3) | lost(3) |
| CPD | upregulated | lost(1) | lost(1),gain(1) | 5 lost(5), gain(5) | lost(3), conserved(2), gain(2) |
| CPNE6 | downregulated | | | 1 lost(1) | lost(1),gain(1) |
| CREB3L1 | downregulated | | | 1 lost(1) | lost(1), gain(1) |
| CRIM1 | downregulated | | | 1 lost(1) | lost(1),gain(1) |
| CSPG4 | downregulated | | | 2 lost(1),conserved(1) | lost(1),conserved(1) |
| CUL4A | upregulated | lost(1) | lost(1) | | gain(7) |
| CYR61 | upregulated | | | 2 lost(2) | lost(2), gain(2) |
| CYTH4 | downregulated | | | 2 lost(2) | lost(2) |
| DGCR5 | downregulated | | | 2 lost(2), gain(1) | lost(1), conserved(1), gain(1) |
| DLG4 | downregulated | | | 3 lost(3), gain(1) | lost(3) |
| DNAJC15 | upregulated | lost(1) | lost(1) | 8 lost(8), gain(1) | lost(7), conserved(1), gain(4) |
| DPF3 | downregulated | | | 2 lost(2) | lost(2),gain(1) |

FIG. 16 (Continued)

| Gene | | | |
|---|---|---|---|
| DRP2 | downregulated | | |
| DUSP1 | upregulated | conserved(1) | conserved(1) | 1 lost(1),gain(1) |
| E2F2 | downregulated | | | 2 lost(1),conserved(1),gain(1) |
| EDNRA | upregulated | | | 2 lost(2),gain(1) |
| EFCAB1 | downregulated | | | 1 lost(1), gain(1) |
| EFNA2 | downregulated | | | 1 lost(1) |
| EIF1AX | upregulated | | | 1 lost(1) |
| EIF2S1 | upregulated | 1 lost(1) | | 2 lost(2),gain(4) | lost(2),gain(1) |
| EIF3C | upregulated | | | 2 lost(2) | lost(1),conserved(1) |
| EIF4E | upregulated | 1 lost(1) | | gain(1) |
| EIF5B | upregulated | | | 1 lost(1) | lost(1) |
| ELF1 | upregulated | | | 3 lost(3), gain(6) | lost(2), conserved(1), gain(5) |
| ELOVL5 | upregulated | | | 1 lost(1) | lost(1),gain(2) |
| F2R | upregulated | | | 3 lost(3) | lost(2), conserved(1) |
| FAM13A | upregulated | | | 1 lost(1) | lost(1) |
| FGFR3 | downregulated | | | 2 lost(2),gain(1) | lost(1),conserved(1) |
| FOSL2 | downregulated | | | 1 lost(1) | lost(1) |
| FOXN1 | downregulated | | | 5 lost(4),conserved(1), gain(6) | lost(4),conserved(1), gain(6) |
| FOXO1 | upregulated | | | 3 lost(3) | lost(3), gain(4) |
| FTSJ1 | upregulated | | | 4 lost(4), gain(1) | lost(4), gain(3) |
| GADD45B | upregulated | 1 lost(1) | | 2 lost(1), conserved(1) | lost(1), conserved(1) |
| GCSH | upregulated | | | 1 lost(1) | lost(1) |
| GNLY | upregulated | | | 5 lost(5), gain(1) | conserved(5) |
| GPR12 | downregulated | | | 2 lost(2), gain(5) | lost(2), gain(6) |
| GPR137 | downregulated | | | 1 lost(1) | lost(1) |
| GTPBP4 | upregulated | 1 lost(1) | | gain(2) |
| GUCA1A | downregulated | 1 lost(1) | conserved(1) | 1 gain(2) | gain(2) |
| HOMER1 | upregulated | | | 1 lost(1) | lost(1) |
| ID1 | upregulated | | | 2 lost(2) | lost(2),gain(1) |

FIG. 16 (Continued)

| Gene | Regulation | | | Count | | |
|---|---|---|---|---|---|---|
| IL15 | upregulated | | | 2 | lost(2) | lost(2) |
| IL1R1 | upregulated | | | 2 | lost(1)conserved(1) | lost(1), conserved(1) |
| IL1RAPL1 | downregulated | | | 1 | lost(1) | lost(1), gain(1) |
| IL27RA | upregulated | | | 1 | lost(1),gain(1) | conserved(1),gain(1) |
| IL7R | upregulated | | | 4 | lost(3), conserved(1), gain(2) | lost(3), conserved(1), gain(7) |
| IPO7 | upregulated | | | 2 | lost(2),gain(1) | lost(2),gain(1) |
| IQGAP2 | upregulated | | | 3 | lost(3) | lost(2),conserved(1) |
| IRAK3 | upregulated | lost(1) | | 1 | lost(1) | lost(1) |
| ITGB3 | downregulated | | | 4 | lost(4), gain(3) | lost(2), conserved(2), gain(7) |
| JAK1 | upregulated | | | 2 | lost(2) | lost(1), conserved(1) |
| JAM3 | upregulated | | | 1 | lost(1) | lost(1) |
| KCTD3 | upregulated | | | 1 | lost(1) | conserved(1) |
| KDR | upregulated | | | 1 | lost(1) | lost(1) |
| KIAA0922 | upregulated | | | 1 | lost(1) | lost(1), gain(2) |
| KIAA1462 | upregulated | | | 3 | lost(3), gain(1) | lost(2), conserved(1) |
| KIF13A | downregulated | | gain(1) | 1 | lost(1), gain(2) | lost(1), gain(1) |
| KISS1 | downregulated | | | 3 | lost(3),gain(2) | lost(3),gain(1) |
| LARP4 | upregulated | | | 1 | lost(1), gain(1) | lost(1), gain(1) |
| LMNA | downregulated | | | 4 | lost(4), gain(3) | lost(4), gain(1) |
| LRPPRC | upregulated | lost(1) | lost(1) | 1 | lost(1), gain(1) | lost(1), gain(2) |
| LRRC41 | downregulated | lost(1) | lost(1) | 1 | lost(1) | lost(1) |
| MAPRE2 | downregulated | lost(1) | lost(1) | 1 | lost(1) | lost(1) |
| MAS1 | downregulated | | | 2 | lost(2),gain(1) | lost(2) |
| MASP1 | downregulated | | | | | |
| MBNL1 | upregulated | lost(1) | conserved(1) | 2 | lost(2) | lost(2) |
| MCL1 | upregulated | gain(1) | | 4 | lost(2), conserved(2) | lost(2), conserved(2), gain(1) |
| METTL2B | upregulated | | | 2 | lost(2) | lost(1),conserved(1) |
| MFSD6 | upregulated | lost(1) | lost(1) | | | |

FIG. 16 (Continued)

| Gene | Reg | | | | |
|---|---|---|---|---|---|
| MGAT4A | upregulated | | | 1 | lost(1) |
| MICAL2 | upregulated | | | 8 | lost(7), conserved(1), gain(1) | lost(7), conserved(1) |
| MORF4L2 | upregulated | | | 2 | lost(2) | lost(2), gain(1) |
| MPL | downregulated | | | 1 | lost(1) | conserved(1),gain(1) |
| MRS2 | upregulated | | | 1 | lost(1),gain(1) | lost(1) |
| MTRR | upregulated | | | 3 | lost(3), gain(2) | lost(3), gain(7) |
| MUC1 | upregulated | lost(1) | | | | gain(1) |
| MX1 | upregulated | | | 1 | lost(1), gain(1) | lost(1) |
| MYBL1 | upregulated | | | 3 | lost(3) | lost(2),conserved(1),gain(1) |
| NAP1L1 | upregulated | | | 1 | lost(1), gain(1) | lost(1), gain(1) |
| NBN | upregulated | | | 1 | conserved(1) | conserved(1) |
| NCOR2 | downregulated | | | 1 | lost(1) | lost(1) |
| NEBL | upregulated | | | 1 | conserved(1) | conserved(1), gain(1) |
| NEDD9 | upregulated | | | 1 | lost(1) | lost(1) |
| NFKBIA | upregulated | conserved(1) | | 3 | lost(3) | lost(3) |
| NIP7 | upregulated | | | 1 | lost(1), gain(2) | lost(1) |
| NKTR | upregulated | | | 2 | lost(1),conserved(1) | lost(1),conserved(1) |
| NNMT | upregulated | conserved(1) | | 1 | lost(1), gain(4) | lost(1), gain(4) |
| NOL11 | upregulated | | | 3 | lost(3), gain(3) | lost(3), gain(13) |
| NOLC1 | upregulated | lost(2) | | 1 | lost(1) | lost(1), gain(1) |
| NOP16 | upregulated | | | 2 | lost(2) | lost(2) |
| NOX5 | downregulated | gain(1) | | | | |
| NR1D2 | upregulated | | | 2 | lost(2) | lost(1), gain(1) |
| OPA1 | upregulated | | | 1 | lost(1), gain(1) | conserved(1) |
| PAK1IP1 | upregulated | | | 2 | lost(2) | lost(2) |
| PAPPA | downregulated | | | 1 | lost(1) | conserved(1) |
| PARD6B | downregulated | | | 4 | lost(2),conserved(2) | lost(2),conserved(2), gain(2) |
| PCSK5 | upregulated | | | 1 | lost(1) | lost(1) |
| PDCD2 | upregulated | | | 1 | lost(1) | lost(1), gain(1) |

FIG. 16 (Continued)

| | | | | | |
|---|---|---|---|---|---|
| PDLIM5 | upregulated | | 1 | | conserved(1) |
| PDZD2 | upregulated | | 4 | lost(4), gain(2) | lost(4), gain(4) |
| PGRMC2 | upregulated | | 2 | lost(2) | lost(2) |
| PHB | upregulated | lost(2) | 2 | lost(1),conserved(1) | lost(5), gain(7) |
| PHF8 | downregulated | | 5 | lost(5), gain(7) | lost(3), gain(4) |
| PHLDA2 | upregulated | gain(1) | 3 | lost(3) | lost(1),conserved(1),gain(2) |
| PIK3R1 | upregulated | | 2 | lost(2) | lost(1), gain(3) |
| PKP2 | upregulated | | 1 | conserved(1), gain(4) | lost(1), conserved(1) |
| PLAC8 | upregulated | | 2 | lost(2) | lost(1), gain(1) |
| PLD1 | downregulated | | 1 | lost(1) | lost(1),gain(1) |
| PLEKHF2 | upregulated | lost(1) | 1 | lost(1) | conserved(1), gain(1) |
| PLEKHG3 | downregulated | | 1 | lost(1), gain(1) | lost(1),gain(2) |
| PLG | downregulated | | 6 | lost(5),conserved(1),gain(13) | lost(5),gain(13) |
| PLSCR1 | upregulated | | 1 | lost(1) | conserved(1) |
| PML | downregulated | lost(1) | 3 | lost(3), gain(7) | lost(2),conserved(1), gain(10) |
| PNN | upregulated | | 1 | lost(1) | conserved(1) |
| PPP1CB | upregulated | | 1 | lost(1) | conserved(1), gain(1) |
| PRKAR2B | upregulated | | 2 | lost(2) | lost(1), conserved(1), gain(1) |
| PRKX | upregulated | | 2 | lost(2) | lost(2), gain(2) |
| PTP4A1 | upregulated | | 1 | lost(1), gain(1) | lost(1) |
| PTPRG | upregulated | | 1 | lost(1) | lost(1) |
| RABEP1 | upregulated | | 1 | lost(1) | lost(1) |
| RASA2 | upregulated | conserved(1) | | | |
| RASSF4 | upregulated | | 1 | lost(1) | lost(1),gain(2) |
| RGS2 | upregulated | | 1 | lost(1), gain(1) | conserved(1), gain(1) |
| RGS3 | downregulated | | 2 | lost(2) | lost(2), gain(1) |
| RHOBTB1 | upregulated | | 1 | lost(1) | conserved(1) |

FIG. 16 (Continued)

| Gene | Regulation | | | | |
|---|---|---|---|---|---|
| RIOK2 | upregulated | | | 1 | lost(1) | lost(1), gain(1) |
| RPL13 | upregulated | | | 3 | lost(2),conserved(1) | lost(2),conserved(1) |
| RPL31 | upregulated | | | 2 | lost(2) | lost(2) |
| RPS6KA2 | upregulated | | | 1 | lost(1) | lost(1) |
| RPS6KB1 | upregulated | 1 | lost(1) | 10 | lost(9), conserved(1), gain(4) | lost(7), conserved(3), gain(5) |
| RRP15 | upregulated | | | 1 | lost(1) | lost(1), gain(2) |
| RTN1 | upregulated | | | 1 | lost(1) | conserved(1) |
| SASH3 | upregulated | | | 1 | lost(1),gain(1) | lost(1),gain(4) |
| SEC14L1 | upregulated | 1 | lost(1) | 15 | lost(14), conserved(1), gain(10) | lost(13), conserved(2), gain(6) |
| SEMA7A | downregulated | | | 1 | lost(1) | lost(1) |
| SEPP1 | upregulated | | | 3 | lost(3), gain(1) | lost(3), gain(3) |
| SGK1 | upregulated | 1 | lost(1) | | conserved(1) | |
| SLC16A7 | upregulated | 1 | lost(1) | 1 | lost(1) | lost(1) |
| SLC19A2 | upregulated | | | | conserved(1) | |
| SLC2A3 | upregulated | | | 4 | lost(4), gain(2) | lost(3), conserved(1), gain(1) |
| SLC30A5 | upregulated | | gain(2) | 2 | lost(2), gain(4) | lost(2), gain(3) |
| SLC46A3 | upregulated | | | 4 | lost(4), gain(3) | lost(3), conserved(1), gain(1) |
| SMAD3 | downregulated | 1 | lost(1) | 4 | lost(4) | lost(4) |
| SNTB2 | downregulated | | | 1 | lost(1) | lost(1) |
| SP110 | upregulated | 1 | lost(1) | | | |
| SPATA5L1 | upregulated | | | 1 | lost(1) | lost(1) |
| SRGN | upregulated | | | 2 | lost(2), gain(1) | lost(1), conserved(1), gain(1) |
| SSBP2 | upregulated | | | 2 | conserved(2) | conserved(2) |
| STC1 | downregulated | | | 2 | lost(2), gain(1) | lost(2) |
| STK39 | upregulated | | | 1 | lost(1) | conserved(1) |
| STOM | upregulated | | gain(1) | 1 | lost(1) | lost(1), gain(1) |
| SYT1 | downregulated | | | 2 | lost(2) | lost(2) |
| TAF9B | upregulated | | | 1 | lost(1), gain(1) | lost(1), gain(1) |

FIG. 16 (Continued)

| | | | | | |
|---|---|---|---|---|---|
| TBL1X | upregulated | | gain(1) | 6 | lost(4), conserved(2), gain(1) | lost(4), conserved(2), gain(1) |
| TBXA2R | downregulated | | | 1 | lost(1) | conserved(1), gain(1) |
| TCERG1 | upregulated | 1 | lost(1) | | | |
| TCF7L2 | upregulated | | | 1 | lost(1) | lost(1), gain(1) |
| TCN1 | downregulated | | | 1 | lost(1), gain(1) | lost(1) |
| TEF | downregulated | | | 1 | conserved(1) | conserved(1),gain(1) |
| TFPI | upregulated | | | 1 | | conserved(2) |
| TGFA | downregulated | 1 | lost(1) | 2 | lost(1), conserved(1) | |
| TGFB2 | upregulated | | lost(1) | 1 | lost(1) | lost(1), gain(2) |
| THOC2 | upregulated | | | 3 | lost(3), gain(3) | lost(2), conserved(1), gain(2) |
| TIAM2 | downregulated | | | 1 | lost(1), gain(1) | conserved(1), gain(1) |
| TIMM17A | upregulated | | | 2 | lost(2) | lost(1),conserved(1),gain(2) |
| TLR2 | upregulated | | | 3 | lost(3) | lost(1), conserved(2), gain(1) |
| TMEM165 | upregulated | | | 2 | lost(2) | lost(2),gain(1) |
| TMOD3 | upregulated | | | 1 | lost(1) | lost(1), gain(1) |
| TNFAIP3 | upregulated | | | 1 | lost(1) | lost(1) |
| TNFSF11 | downregulated | | | 8 | lost(8), gain(1) | lost(8), gain(9) |
| TRA2A | upregulated | | | 1 | lost(1) | conserved(1) |
| TSC22D3 | upregulated | | lost(1), conserved(1) | 10 | lost(7), conserved(3), gain(3) | lost(3), conserved(7), gain(2) |
| TXNIP | upregulated | 2 | lost(2) | 1 | lost(1), gain(3) | conserved(1), gain(2) |
| TYRO3 | downregulated | | | 2 | lost(2),gain(2) | lost(2) |
| UBE2B | upregulated | | | 1 | conserved(1) | conserved(1) |
| USE1 | upregulated | | | 2 | lost(2),gain(1) | lost(2) |
| USP36 | upregulated | 1 | lost(1), gain(1) | 3 | lost(3), gain(7) | lost(3), gain(11) |
| USP46 | upregulated | 1 | lost(1) | | | gain(1) |
| UTP14A | upregulated | | | 1 | lost(1),gain(2) | lost(1), gain(2) |

FIG. 16 (Continued)

| | | | | | |
|---|---|---|---|---|---|
| VEGFA | downregulated | | | | |
| WDFY3 | upregulated | | | 1 | lost(1) | lost(1),gain(3) |
| XIST | upregulated | | | 1 | lost(1) | lost(1), gain(1) |
| XPNPEP1 | upregulated | | | 1 | lost(1) | lost(1),gain(1) |
| ZBTB38 | upregulated | | | 1 | lost(1) | lost(1) |
| ZFAND5 | upregulated | 1 | lost(1) | 3 | lost(3) | lost(1), conserved(2), gain(1) |
| ZFP36L2 | upregulated | 1 | lost(1) | conserved(1) | 1 | lost(1) | lost(1), gain(2) |
| ZNF146 | upregulated | 1 | lost(1) | lost(1) | 1 | conserved(1) | conserved(1) |
| ZNF189 | upregulated | 2 | lost(2) | lost(2) | | gain(1) | gain(2) |
| ZNHIT6 | upregulated | | | 2 | lost(2) | lost(2), gain(1) |
| ZSCAN12 | upregulated | | | 1 | lost(1), gain(3) | lost(1), gain(3) |

SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggagaaactg ctgcctcata tc                                              22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagcagctgg caccttatt                                                  19

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcaccacca gtccaca                                                    17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcacgccgg agtatct                                                    17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctgacagcg cggaatct                                                    18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
gatttccacc gggccac                                                     17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
acaggccatg gatctggtga                                                  20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
cagctctcgg atctgctcct t                                                21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
tggctaaaca cttgaagacc                                                  20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
ggaagaactc cacaaaccc                                                   19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
gagcagaagt tctccagcct                                                  20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accattcgat tgtgtagcca                                               20
```

METHODS AND COMPOSITIONS RELATED TO TRIPLE-NEGATIVE BREAST CANCER

CROSS-REFERENCE TO RELATED APPLICATIONS

This application claims the benefit of priority of U.S. Provisional Patent Application No. 62/597,534 filed Dec. 12, 2017, which is hereby incorporated by reference in its entirety.

The instant application contains a Sequence Listing which has been submitted in ASCII format and is hereby incorporated by reference in its entirety. Said ASCII copy, created on Mar. 13, 2019, is named ARCD_P0638US_1001055257_SL.txt and is 3,202 bytes in size.

GOVERNMENT SUPPORT CLAUSE

This invention was made with government support under R01 CA089208 and P30 CA014599 awarded by the National Institutes of Health. The government has certain rights in the invention.

BACKGROUND OF THE INVENTION

I. Field of the Invention

Embodiments of this invention are directed generally to biology and medicine. In certain aspects methods involve determining the prognosis for a breast cancer patient including risk of recurrence. In other embodiments, there are methods and compositions for treating a breast cancer patient with radiation, chemotherapy, immunotherapy, an Hsp90 inhibitor, and/or a glucocorticoid antagonist.

II. Background

Aggressive breast cancers (BCs) that commonly lack the expression of estrogen receptor (ER), progesterone receptor (PR), and HER2 are broadly categorized together as triple-negative breast cancers (TNBCs). The absence of these receptors, particularly ER, poses a challenge to patient treatment options in part because of the lack of druggable targets for TNBC (1). Resistance (de-novo or acquired) of tumor cells to adjuvant treatment is also thought to contribute to increased relapse rates in early-stage TNBC patients (2). Recent efforts to distinguish the variable natural history of TNBC have used gene expression to divide these cancers into four subtypes: basal-like-1, basal-like-2, mesenchymal, and luminal androgen receptor (LAR) (3, 4). Additionally, genomic, epigenetic, and proteomic analyses of TNBCs have revealed several potential targets, including androgen receptor (AR), EGFR, JAK2, mTOR, and PI3K (5-16). Despite these advances, outside of clinical trials, patients with early-stage TNBC still receive generic adjuvant cytotoxic chemotherapy. Therefore, the identification of targetable regulators of TNBC aggressiveness and chemoresistance remains a critical need.

The identification of molecular targets that play a critical role in TNBC chemoresistance and recurrence is important for the development of more effective therapies. Given the diverse subtypes of TNBC, it seems unlikely that one molecule will be a master regulator of poor prognosis in all TNBC. Recently, GR has been identified as an upstream regulator of important pro-oncogenic pathways through its ability to regulate transcription and remodel chromatin. Previous reports from our laboratory (52) and others (44, 55) have found a significant association between shortened RFS in early-stage ER-negative BC patients and high tumor GR expression, suggesting that GC-activated GR-mediated regulation of gene expression may contribute to chemotherapy resistance and shortened RFS. Because endogenous cortisol-activated GR is a transcriptional regulator of thousands of direct and indirect target genes that vary in individual cell types (93-95), identifying those GR-regulated genes that are most relevant to prognosis and treatment of TNBC has been a challenge. Therefore, the identification of targetable regulators of TNBC chemoresistance, particularly GR-regulated genes, and the treatment of such breast cancers remains a critical need.

SUMMARY OF THE INVENTION

Embodiments concern methods, compositions, and apparatuses related to assessing, prognosing, and/or treating cancer patients. The identification of patients that may be especially suited for treatment with a particular therapy is a goal of some embodiments disclosed herein. In particular, genes that can be used to identify more accurately those patients are useful. In addition, methods, compositions, and apparatuses concerning determining a patient at risk for recurrence of cancer and treatment options in view of that risk are also provided.

Accordingly, embodiments include treating a breast cancer patient; treating a breast cancer patient with a GR antagonist; treating a cancer patient with a GR inhibitor, treating a breast cancer patient with radiation; treating a breast cancer patient determined to be at risk for recurrence; treating a triple-negative breast cancer patient; treating a breast cancer patient previously treated with a cancer treatment; evaluating a patient with breast cancer; evaluating a breast cancer patient for glucocorticoid receptor antagonist therapy; evaluating a biological sample from a patient; evaluating breast cancer cells from a patient; evaluating a biological sample from a breast cancer patient; assessing a breast cancer patient; testing a breast cancer sample or biopsy; testing a breast tumor; prognosing a breast cancer patient; treating a breast cancer patient, particularly a patient with a particular profile related to ER and GR; determining a treatment for a breast cancer patient; altering a treatment plan for a breast cancer patient; reporting prognosis of a breast cancer patient; determining a prognosis score for a breast cancer patient; generating a prognosis score for a breast cancer patient; assessing the risk of mortality of a breast cancer patient; generating a GR-antagonist responsive profile for a breast cancer patient; comparing a patient's GR-antagonist responsive profile to a standardized profile; and/or, determining a breast cancer patient has a poor prognosis based on one or more GR-antagonist responsive genes.

In specific embodiments there are methods for treating a breast cancer patient comprising administering a glucocorticoid receptor (GR) antagonist to the patient after the level of expression for at least 2 GR-antagonist responsive genes from Supplementary Table S2 ("Table S2") has been measured from a biological sample from the patient. In some embodiments, the patient is administered a GR inhibitor. A "GR inhibitor" refers to a compound or agent that inhibits or reduces GR expression or activity, though it includes, but is not limited to GR antagonists. In some embodiments, a GR inhibitor is not a GR ligand binding domain antagonist. Hsp90 inhibitors and Compound A are examples of non-GR ligand binding domain antagonist inhibitors. Any embodiment discussed herein in the context of administering a GR antagonist may be implemented with a GR inhibitor, and vice versa.

In further embodiments, there are methods for treating a breast cancer patient comprising administering a glucocorticoid receptor (GR) antagonist (or GR inhibitor) to the patient after the level of transcription for at least 5 genes from Supplementary Table S3 or Supplementary Table S4 has been measured from a biological sample from the patient.

Additional embodiments concern methods for treating a breast cancer patient comprising administering a glucocorticoid receptor (GR) antagonist (or GR inhibitor) to the patient whose transcription levels of at least 2 genes on Table S2 are measured and the breast cancer is determined to be GR-antagonist responsive.

Any embodiment discussed in the context of a method for treating may also be recited as a use of one or more therapeutic agents, and vice versa. In some embodiments, there is the use of a glucocorticoid receptor antagonist (or GR inhibitor) and a chemotherapeutic for the treatment of GR+, ER− breast cancer in a patient determined to be GR-antagonist responsive based on the level of transcription of at least two genes in any of Tables S2, S3, and/or S4. In specific embodiments, the genes are from Table S2. Alternatively or additionally, the treatment may include radiation, immunotherapy, hormone therapy, and/or other biological therapy In certain embodiments, a patient is treated with one or more therapies such as chemotherapeutics, immunotherapeutics, hormones, radiation, Hsp90 inhibitors, Compound A, glucocorticoid receptor inhibitors, and/or glucocorticoid receptor antagonists. A patient may be treated before, after, or both before and after with one or more of these agents with respect to being tested for gene expression of one or more GR-responsive genes. A "GR-responsive biomarker" refers to a gene whose mRNA expression is detectably increased or decreased in a biological sample relative to the level of expression of a gene whose expression is known to remain within a standard deviation of measurement in the presence of a glucocorticoid receptor agonist (like dexamethasone) or glucororticoid receptor antagonist (like mifepristone). In some embodiments, the change is an increase of at least 1.3× relative to a housekeeping gene or a decrease of at least 0.67× relative to a housekeeping gene. In certain embodiments, a GR-responsive biomarker is a gene listed in Table S2. Other GR-responsive biomarkers may be found in Tables S3 or S4. A number of embodiments concern measuring the level of expression of a panel of GR-responsive biomarkers.

Other embodiments concern methods for evaluating a breast cancer patient for GR antagonist or GR inhibitor therapy comprising measuring the level of expression of at least 2 genes in any of Tables S2, S3, and/or S4 and comparing the levels to a control level, which may a reference level(s) that has been previously determined or the levels of a control level may be measured using the patient's biological sample.

In additional embodiments, there are methods for evaluating risk of recurrence in a patient previously treated for breast cancer with a therapy other than with a GR-antagonist or inhibitor, such as radiation and/or chemotherapy, the methods comprising measuring the level of expression of at least 2 genes in any of Tables S2, S3, and/or S4 and comparing the levels to a control level. In some embodiments, a risk score is calculated based on the expression levels.

In some cases, methods concern evaluating a patient with breast cancer comprising: (a) measuring expression levels of at least two genes in any of Tables S2, S3, and/or S4 of primary breast cancer cells from a biological sample from the patient with breast cancer; (b) comparing the expression levels of the at least two genes from step (a) to a threshold activity level of expression in primary breast cancers derived from a cohort of at least 200 test individuals determined to be non-responsive to a GR antagonist or GR inhibitor. In additional embodiments, the extent of GR-antagonism or inhibition is measured using one or more assays that directly or indirectly measure GR activity.

Embodiments also cover apparatuses, kits, and computer readable medium and systems for assessing the expression level of GR-antagonist responsive genes in a patient's breast cancer sample and determining a treatment; and/or treating the patient accordingly. It is specifically contemplated that a breast cancer patient is a human. In some embodiments, the patient is female, while in others, the patient is male. Accordingly, in human patients, ER refers to an estrogen receptor in a human and GR refers to a glucocorticoid receptor in a human.

A number of embodiments concern one or more genes whose expression is altered in response to a glucocorticoid receptor agonist or antagonist, i.e., the one or more genes are GR-responsive biomarkers. In any embodiment discussed herein, there is involved at least, at most or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, or 462 (or any range derivable therein) genes (referred to as a plurality of genes) from those identified in Supplementary Table S2 ("Table S2"), Supplementary Table S3 ("Table S3"), or Supplementary Table S4 ("Table S4").

More specifically, the genes in Table S2 are ABHD5, ACSL3, AP1AR, ASMTL, ATP2B1, BBS10, BCOR, C12orf29, CACNAIG, CCT6A, CDK7, CDKN2D, CHMP2B, COL4A6, COL7A1, CORO2B, CPNE6, CRY1, CUL4A, DDX18, DLAT, DLG4, EIF3J, ETF1, F2R, FGF5, GL12, GRM5, GRM6, HEATR3, HOMER1, HPS5, HSPA9, IMPACT, IP07, IQCC, KCTD3, KISS1, LMNA, LYPLA1, MAPRES2, MAS1, MUCSAC, NAP1L1, NOL11, NOX5, PEX3, PGRMC2, PLCB4, POLQ, PRPF39, RABGGTB, RMND1, RPL31, RRH, SCN3B, SEH1L, SERP1, SERPIND1, SLC4A4, SPATASL1, SSB, SSBP3, SYT1, TBXA2R, TCEB1, TROAP, TSEN2, TYRO3, USE1, UTP14A, WDR43, WNTSA, and ZNF189 (referred collectively as the 72-gene panel"). It is specifically contemplated that any of these genes may be included or excluded in an embodiment.

The genes in Supplementary Table S3 are ABHD5, ACAA2, ACSL1, ADAMTS12, ADAMTS6, AGPAT5, ALCAM, AMMECR1, ANGEL2, ANK2, APOOL, ARIH2, ARMC8, ATP2B1, B3GALT5, BBS10, BCL3, BCLAF1, BIRC3, BIRC5, BPTF, BRWD1, C10orf10, C1QTNF3, CACNAIG, CALD1, CAMK4, CARD10, CAV2, CBL, CCDC6, CCT6A, CDKL2, CDKN1C, CDKN2D, CHN2, COL1A1, COL4A6, COL7A1, COPS2, COPS8, COX15, CPD, CPNE6, CREB3L1, CRIM1, CSPG4, CUL4A, CYR61, CYTH4, DGCR5, DLG4, DNAJC15, DPF3, DRP2, DUSP1, E2F2, EDNRA, EFCAB1, EFNA2, EIF1AX, EIF2S1, EIF3C, EIF4E, EIF5B, ELF1, ELOVL5, F2R, FAM13A, FGFR3, FOSL2, FOXN1, FOXO1, FTSJ1, GADD45B, GCSH, GNLY, GPR12, GPR137, GTPBP4, GUCA1A, HOMER1, ID1, IL15, IL1R1, ILIRAPLI, IL27RA, IL7R, IMPACT, IP07, IQCC, IQGAP2, IRAK3, ITGB3, JAK1, JAM3, KCTD3, KDR, KIAA0922, KIAA1462, KIF13A, KISS1, LARP4, LMNA, LRPPRC, LRRC41, MAPRE2, MAS1, MASP1, MBNL1, MCL1, METTL2B, MFSD6, MGAT4A, MICAL2, MORF4L2, MPL, MRS2, MTRR, MUC1, MXIl, MYBL1, NAP1L1, NBN, NCOR2, NEBL, NEDD9, NFKBIA, NIP7, NKTR, NNMT, NOL11, NOLC1, NOP16, NOX5, NR1D2, OPA1, PAK1IP1, PAPPA, PARD6B, PCSK5, PDCD2, PDLIM5, PDZD2, PGRMC2, PHB, PHF8, PHLDA2, PIK3R1, PKP2, PLAC8, PLD1, PLEKHF2, PLEKHG3, PLG, PLSCR1, PML, PNN, PPP1CB, PRKAR2B, PRKX, PTP4A1, PTPRG, RABEPI, RASA2, RASSF4, RGS2, RGS3, RHOBTB1, RIOK2, RPL13, RPL31, RPS6KA2, RPS6KB1, RRP15, RTN1, SASH3, SEC14L1, SEMA7A, SEPP1, SGK1, SLC16A7, SLC19A2, SLC2A3, SLC30A5, SLC46A3, SMAD3, SNTB2, SP110, SPATA5L1, SRGN, SSBP2, STC1, STK39, STOM, SYT1, TAF9B, TBL1X, TBXA2R, TCERG1, TCF7L2, TCN1, TEF, TFPI, TGFA, TGFB2, THOC2, TIAM2, TIMM17A, TLR2, TMEM165, TMOD3, TNFAIP3, TNFSF11, TRA2A, TSC22D3, TXNIP, TYRO3, UBE2B, USE1, USP36, USP46, UTP14A, VEGFA, WDFY3, XIST, XPNPEP1, ZBTB38, ZFAND5, ZFP36L2, ZNF146, ZNF189, ZNHIT6, and ZSCAN12 (referred collectively as the 232-gene panel"). It is specifically contemplated that any of these genes may be included or excluded in an embodiment.

The genes in Table S4 are ABCD4, ABCE1, ABHD5, ACAA2, ACSL1, ACSL3, ACSL4, ADAM10, ADAM19 ADAMTS12, ADAMTS6, AGFG1, AGPAT5, AIMP1, AKAP12, ALCAM, AMD1, AMMECR1, AMOTL2, ANGEL2, ANK2, AP1AR, AP4S1, APOOL, AREG, ARHGEF4, ARIH2, ARMC4, ARMC8, ARTN, ASCC3, ASMTL, ATG2B, ATM, ATN1, ATP11B, ATP13A3, ATP2B1, ATP5S, ATR, AZI2, B3GALT5, BBS10, BCL3, BCLAF1, BCOR, BIRC3, BIRC5, BMP7, BPTF, BRWD1, C10orf10, C11orf57, C12orf29, C1QTNF3, C1RL, CACNA1G, CALCA, CALD1, CAMK4, CARD10, CASC5, CAV2, CBL, CCDC6, CCNB1IP1, CCT6A, CD24, CDC25A, CDC25C, CDC37L1, CDK7, CDKL2, CDKN1C, CDKN2D, CDO1, CDON, CHCHD7, CHMP2B, CHN2, CHRM3, CIITA, CITED2, CLEC7A, CLSPN, COL1A1, COL4A6, COL7A1, COPS2, COPS8, COQ2, CORO2B, COX15, CPD, CPM, CPNE6, CREB3L1, CRIM1, CRY1, CSPG4, CUL4A, CXCL2, CYR61, CYTH4, CYTIP, DCN, DDX18, DGCR5, DHRS2, DLAT, DLG4, DNAJC15, DPF3, DRP2, DTWD1, DUSP1, E2F2, EBAG9, EDNRA, EFCAB1, EFNA2, EGR1, EIF1AX, EIF2S1, EIF3C, EIF3E, EIF3F, EIF3J, EIF3M, EIF4E, EIF5B, ELF1, ELOVL5, EPB41L5, EPHA5, ESF1, ESRRG, ETF1, ETNK1, EZR, F2R, FAM120A, FAM13A, FAM69A, FANCF, FBXO38, FBXW2, FGF5, FGFR1, FGFR3, FJX1, FOSL2, FOXN1, FOXO1, FTSJ1, FXR1, GAB1, GABARAPLI, GADD45B, GATA3, GCSH, GIMAP6, GIN1, GJA1, GLI2, GLUL, GNLY, GPR12, GPR135, GPR137, GPR161, GPR39, GRIK1, GRM5, GRM6, GTF2H5, GTPBP4, GUCA1A, HEATR3, HIRA, *HOMER*1, HOPX, HPS5, HSPA9, ID1, IGFBP3, IL15, IL1R1, ILIRAPLI, IL27RA, IL7R, IMPACT, IP07, IQCC, IQGAP2, IRAK3, ITGB3, ITGBL1, ITPR2, JAK1, JAK2, JAM2, JAM3, KCTD3, KDR, KIAA0922, KIAA1462, KIF13A, KIN, KISS1, LARP1, LARP4, LIMCH1, LMNA, LRPPRC, LRRC41, LYPLA1, MAFF, MAGI2, MAP9, MAPRE2, MAS1, MASP1, MATR3, MBNL1, MCL1, METAP2, METTL2B, METTL5, MFSD6, MGAT4A, MGAT5, MICAL2, MINA, MORF4L2, MPL, MPP5, MRS2, MS4A4A, MTO1, MTRR, MUC1, MUC5AC, MXIl, MYBL1, NAP1L1, NBN, NCOA3, NCOR2, NDUFAF4, NEBL, NEDD4, NEDD9, NEU3, NFIB, NFKBIA, NIP7, NKTR, NNMT, NOC3L, NOL11, NOLC1, NOP16, NOX5, NR1D2, NRIP1, NSUN7, ODAM, OPA1, OTUD4, PAKIIPI, PAPOLA, PAPPA, PARD6B, PCMTD2, PCNXL2, PCSK5, PDCD2, PDE7B, PDLIM5, PDS5A, PDZD2, PEX3, PEX5L, PGRMC2, PHB, PHF8, PHIP, PHLDA2, PIK3C2A, PIK3R1, PKLR, PKP2, PLAC8, PLCB4, PLD1, PLEKHF2, PLEKHG3, PLG, PLK4, PLOD2, PLSCR1, PML, PMS1, PNN, POLQ, PPP1CB, PRKAR2B, PRKCE, PRKG1, PRKX, PRPF38B, PRPF39, PRRG1, PSMF1, PTCH1, PTP4A1, PTPN13, PTPN2, PTPRG, RAB11FIP1, RABEPI, RABGGTB, RANBP2, RASA2, RASSF4, RBM12, RBM15, RCHY1, RFTN1, RGS12, RGS2, RGS3, RHOBTB1, RIOK2, RMND1, RPL13, RPL31, RPS27A, RPS6KA2, RPS6KB1, RRH, RRP15, RSL1D1, RTN1, SAA1, SASH3, SCAMPI, SCN3B, SCUBE3, SEC14L1, SEC24D, SEH1L, SEMA7A, SENP6, SEPP1, SERBP1, SERP1, SERPIND1, SETD6, SETMAR, SETX, SEZ6L, SGK1, SIK2, SIK3, SLC12A3, SLC16A7, SLC19A2, SLC25A32, SLC25A36, SLC2A3, SLC30A1, SLC30A5, SLC35A3, SLC46A3, SLC4A4, SMAD3, SNTB2, SNX24, SOS1, SOX2, SP110, SPATA5L1, SRGN, SSB, SSBP2, SSBP3, STC1, STK39, STOM, STX7, SULF1, SYNCRIP, SYT1, TAF9B, TAX1BP3, TBL1X, TBXA2R, TCEB1, TCEB3, TCERG1, TCF7L2, TCN1, TEF, TFB2M, TFPI, TGFA, TGFB2, TGFBR3, THOC2, TIAM2, TIMM17A, TIMM8B, TLR2, TM2D1, TMEM165, TMEM33, TMEM5, TMEM87A, TMOD3, TNFAIP3, TNFSF11, TNIP1, TOMM70A, TRA2A, TRA2B, TROAP, TSC22D3, TSEN2, TTC22, TXNIP, TXNL1, TYMS, TYRO3, TYROBP, UBA6, UBE2B, USE1, USP36, USP46, UTP14A, VEGFA, VWA5A, WDFY3, WDR43, WNT5A, WTAP, XIST, XPNPEP1, YIPF4, ZBTB38, ZFAND5, ZFAND6, ZFP36L2, ZMYM6, ZNF146, ZNF189, ZNF529, ZNF7, ZNHIT6, and ZSCAN12 (referred collectively as the "462 gene panel"). It is specifically contemplated that any of these genes may be included or excluded in an embodiment.

It is specifically contemplated that 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, or 462 (or any range derivable therein) of these listed genes or GR-responsive biomarkers may be included or excluded in embodiments described herein. In certain embodiments, at least, at most or exactly a certain plurality of genes may be measured, quantitated, detected, evaluated, and/or compared. In some methods, steps include but are not limited to measuring, quantitating, detecting, evaluating, and/or comparing a plurality of genes. The plurality of genes or biomarkers may be referred to as a panel. A plurality of GR-responsive biomarkers may be referred to as a GR-responsive biomarker panel and any embodiment provided herein with respect to a plurality of genes from any of Tables S2, S3, or S4 may also be implemented with a GR-responsive biomarker panel. In specific embodiments, the gene is a direct target gene, meaning These genes have regulator elements bound by activated GR (by dex) and not be vehicle (control) suggesting they are directly regulated by GR transcriptional activity—they tend to be robust across tumor types and breast cancer types because of the direct nature of the interaction of GR with the gene's regulatory elements.

Some embodiments include generating an expression profile for a patient of GR-responsive genes, which means measuring the level of expression of a plurality of genes whose expression is increased in the presence of or following exposure to a glucocorticoid receptor agonist or decreased in the presence of or following exposure to a glucocorticoid receptor antagonist.

In certain embodiments, methods may involve categorizing the patient as having an increased or decreased level of expression based on the measured level of expression of a GR agonist-responsive gene or GR antagonist-responsive gene and a predetermined threshold value for that GR agonist-responsive or GR antagonist-responsive gene.

In some embodiments, expression of GR agonist-responsive genes is measured, which may be part of generating a GR-responsive expression profile for a patient. GR agonist-responsive genes are those identified in any of Tables S2, S3, and S4. In certain embodiments, those genes are limited to either S2, S3, or S4. In other embodiments, GR-responsive genes are limited to certain genes listed in S2, S3, and/or S4. In Table S2, it shows the following genes are induced by a glucocorticoid agonist (such as dexamethasone) and exhibit an increase in expression (such as greater than 1.3×) following exposure to a GR agonist: ABHD5, ACSL3, AP1AR, ASMTL, ATP2B1, BBS10, BCOR, C12orf29, CCT6A, CDK7, CHMP2B, CRY1, CUL4A, DDX18, DLAT, EIF3J, ETF1, F2R, HEATR3, HOMER1, HPS5, HSPA9, IMPACT, IPO7, KCTD3, LYPLA1, NAP1L1, NOL11, PEX3, PGRMC2, PLCB4, PRPF39, RABGGTB, RMND1, RPL31, SEH1L, SERP1, SPATA5L1, SSB, TCEB1, TSEN2, USE1, UTP14A, WDR43, WNT5A, and ZNF189. In some embodiments, expression is measured with exactly, with at least, or with at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 of these genes (or any range derivable therein). In some embodiments, an increase in expression is measured in one or more of these genes.

In some embodiments, expression of GR antagonist-responsive genes is measured, which may be part of generating a GR-responsive expression profile for a patient. GR antagonist-responsive genes are those identified in any of Tables S2, S3, and S4. In certain embodiments, those genes are limited to either S2, S3, or S4. In other embodiments, GR-responsive genes are limited to certain genes listed in S2, S3, and/or S4. In Table S2, it shows the following genes are decreased by a glucocorticoid antagonist (such as mifepristone) and exhibit an decrease in expression (such as less than 0.67×) following exposure to a GR antagonist: CACNA1G, CDKN2D, COL4A6, COL7A1, CORO2B, CPNE6, DLG4, FGF5, GLI2, GRM5, GRM6, IQCC, KISS1, LMNA, MAPRE2, MAS1, MUC5AC, NOX5, POLQ, RRH, SCN3B, SERPIND1, SLC4A4, SSBP3, SYT1, TBXA2R, TROAP, and TYRO3. In some embodiments, expression is measured with exactly, with at least, or with at most 1, 2, 3, 4, 5, 6, 7, 8, 9, 10, 11, 12, 13, 14, 15, 16, 17, 18, 19, 20, 21, 22, 23, 24, 25, 26, 27, or 28 of these genes (or any range derivable therein). In some embodiments, a decrease in expression is measured in one or more of these genes.

A unique collection of biomarkers as a genetic classifier expressed in a cancer tissue is provided that is useful in determining responsiveness to therapeutic agents, such as GR antagonists or GR inhibitors, used to treat cancer. The panel also provides relevant information about recurrence and/or treatment with other cancer treatment such as chemotherapeutics, radiation, immunotherapeutics, and/or hormone therapy. Such a collection may be termed a "biomarker panel," "expression classifier," or "classifier."

In some embodiments, a score is calculated based on the expression profile of a patient. In certain embodiments, the value assigned to represent the expression of one or more genes may be adjusted. In some cases, a weight is attached to one or more values. The term "weight" refers to the relative importance of an item in a statistical calculation. The weight of each biomarker in a gene expression classifier may be determined on a data set of patient samples using analytical methods known in the art.

In certain embodiments, the relative expression levels of GR-responsive biomarkers in are measured to generate a gene expression profile. The gene expression profile of a set of biomarkers from a patient sample may be set forth as a decision score and compared to a score threshold that is mathematically derived from a training set of patient data. The score threshold separates a patient group based on different characteristics such as, but not limited to, responsiveness/non-responsiveness to treatment such as GR-antagonist or GR-inhibitor therapy The patient training set data may be generated from cancer samples that have been characterized by one or more of the following: prognosis, likelihood of recurrence, long term survival, clinical outcome, treatment response, diagnosis, cancer classification, or personalized genomics profile. In some embodiments, expression profiles and corresponding decision scores from patient samples may be correlated with the characteristics of patient samples in a training set that are on the same side of the mathematically derived score decision threshold. The threshold of the linear classifier scalar output is optimized to maximize the sum of sensitivity and specificity under cross-validation as observed within the training dataset.

In additional embodiments, the overall expression data for a given sample is normalized using methods known to those skilled in the art in order to correct for variables such as amounts of starting material, efficiencies of the isolation, purification, and/or amplification reactions, or in assay conditions. Using a linear classifier on the normalized data to make a prognostic call (e.g., responsiveness to a GR antagonist or recurrence) effectively means to split the data space, i.e. all possible combinations of expression values for all genes in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, i.e. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

In some embodiments, a biomarker expression profile of a patient sample is evaluated by a linear classifier. A linear classifier refers to a weighted sum of the individual biomarker values into a compound decision score ("decision function"). In certain embodiments a decision score is compared to a pre-defined cut-off score threshold that corresponds to a certain set-point with respect to sensitivity and specificity, which indicates whether a sample is above the score threshold (decision function positive) or below (decision function negative).

In further embodiments, a weighted sum of the pre-processed intensity values for each mRNA transcript is formed and compared with a threshold value optimized on the training set (Duda et al. Pattern Classification, 2 Ed., John Wiley, New York 2001). The weights can be derived by a multitude of linear classification methods, including but not limited to Partial Least Squares (PLS, (Nguyen et al., 2002, Bioinformatics 18 (2002) 39-50)) or Support Vector Machines (SVM, (Scholkopf et al. Learning with Kernels, MIT Press, Cambridge 2002)). In an additional embodiment, data is transformed non-linearly before applying a weighted sum as described above. This non-linear transformation might include increasing the dimensionality of the data. The non-linear transformation and weighted summation might also be performed implicitly, e.g., through the use of a kernel function. (Scholkopf et al., Learning with Kernels, MIT Press, Cambridge 2002).

Some embodiments for cancer treatment concern a GR antagonist, which means a compound or substance that does not provoke a biological response itself upon binding to the glucocorticoid receptor, but that blocks or dampens agonist-mediated responses. Some GR antagonists also have some agonist activity, in which case they may be referred to as GR modulator; unless otherwise specified, GR modulators are included as GR antagonists though in some embodiments, a GR modulator may be excluded specifically or as a class of compounds. An example of a GR modulator is CORT 108297, CORT 118335, CORT 12534, or CORT 108134.

In some embodiments, a GR antagonist is administered to a subject. In certain embodiments, the subject is tested for an ability to respond to one or more GR antagonists, which can be done by evaluating levels of expression of 1 or more GR antagonist responsive genes, which are genes whose level of expression changes in a number of individuals after exposure to a GR antagonist. In certain embodiments, a GR antagonist is non-selective, while in other embodiments, it is selective. In some embodiments, a GR antagonist is a steroidal compound, though in other embodiments, it is nonsteroidal. The GR antagonist may be a compound that is an octahydrophenanthrene (CAS Registry Number: 5325-97-3), spirocyclic dihydropyridine, triphenylmethanes and diaryl ether, chromene, dibenzyl aniline, dihydroisoquinoline, pyrimidinedione (CAS Registry Number: 504-07-4), azadecalin, and/or aryl pyrazolo azadecalin. In certain embodiments, the GR antagonist is CORT108297, CORT118335 (shown below), or CORT 125134 (J. Med. Chem., 2017, 60 (8), pp 3405-3421, which is hereby incorporated by reference), or any other GR antagonist identified in Mohler et al., Expert Opin. Ther. Patents (2007) 17(1): 59-81, which is hereby incorporated by reference. In other embodiments, the GR antagonist is ORG 34517 (PubChem CID 9824013) or an analog thereof or any other GR inhibitor in US Patent Publication 2016/0289261, which is hereby incorporated by reference. In some cases, the GR antagonist includes, but is not limited to, beclometasone, betamethasone, budesonide, ciclesonide, flunisolide, fluticasone, mifepristone, mometasone, and triamcinolone.

In some embodiments the GR antagonist includes compounds analogs discussed in Clark, 2008, Current Topics in Medicinal Chemistry. Vol. 8, No. 9. pp. 813-838 or Mohler et al., Expert Opin. Ther. Patents (2007) 17(1):59-81, which are both specifically incorporated by reference. Compounds include cortisol, dexamethasone, RTI 3021-012, RTI 3021-022, cyproterone acetate. Analogs and/or derivatives include those of the following compounds: RU-43044, RU-486 (mifepristone or RU-38486; for example, Compound 1, Compound 2, Compound 3, Compound 4, Compound 5, Compound 6, Compound 7, Compound 8, Compound 8, Compound 9, Compound 10, Compound 11, Compound 12, Compound 13 (or RU-486), Compound 14, Compound 15 and Compound 16, Compound 17, Compound 18, Compound 19, Compound 20, Compound 21, Compound 22, Compound 23, Compound 24, Compound 25, Compound 26, Compound 27, Compound 28, Compound 29, Compound 30), 11-Monoaryl steroids, 11,21 bisaryl steroids (for example Compound 31 (Org 34517), Compound 32 (Org 34850) and Compound 33 (Org 36410)), 110-Aryl conjugates of mifepristone (for example, Compound 34, Compound 35, Compound 36, Compound 37, Compound 38, Compound 39, Compound 40, Compound 41, Compound 42, Compound 43, Compound 44, and Compound 45); phosphorus-containing mifepristone analogues (for example, Compound 47 and Compound 48), octahydrophenanthrenes (for example, (S)-49, (R)-49, Compound 50 (or CP-409069), Compound 51 (or CP-394531), Compound 52, Compound 53, Compound 54, Compound 55, Compound 56, Compound 57, Compound 58, Compound 59, Compound 60, Compound 61 (CP-47255) Compound 62 and Compound 63), sprirocyclic dihydropyridines (for example, Compound 64, Compound 65, Compound 66, Compound 67, Compound 68 and Compound 69), triphenylmethanes (for example, Compound 70 and Compound 71), diaryl ethers (for example, Compound 72), chromenes (Compound 73, Compound 74, Compound 75, Compound 76, Compound 77, Compound 78, Compound 79, Compound 80, Compound 81, and Compound 82), dibenzyl anilines (for example, Compound 83, Compound 84, Compound 85, Compound 86, Compound 87, Compound 88, Compound 89, Compound 90, Compound 91 and Compound 92), dihydroquinolines (for example, Compound 93 and Compound 94), pyrimidinediones (for example, Compound 95, Compound 96, Compound 97, Compound 98, Compound 99, Compound 100, Compound 101, Compound 102, Compound 103, Compound 104 and Compound 105 as well as Compound 106, Compound 107, Compound 108, Compound 109, Compound 110, Compound 111, Compound 112, Compound 113, Compound 114, Compound 115, and Compound 116), azadecalins (For example Compound 117, Compound 118, Compound 119, Compound 120, Compound 121, Compound 122, Compound 123, Compound 124, (R)-123, Compound 124, Compound 125, Compound 126, Compound 127, Compound 128, and Compound 129), aryl pyrazolo azadecalins (for example Compound 130, Compound 131, Compound 132, Compound 133, Compound 134, Compound 135, Compound 136, Compound 137, Compound 138, Compound 139, Compound 140, Compound 141, Compound 142, Compound 143, Compound 144, Compound 145, Compound 146, Compound 147, Compound 148, Compound 149, Compound 150, Compound 151, Compound 152, Compound 153, Compound 154, Compound 155, Compound 156, Compound 157, Compound 158, Compound 159, Compound 160, Compound 161, Compound 162, Compound 163, Compound 164, Compound 165, Compound 166, Compound 167, Compound 168 and Compound 169). In other embodiments GR antagonists include nonsteroidal antagonist compound 8 (See Luz et al. 2015. Journal of Medicinal Chemistry. 58, 6607-6618). In some embodiments, GR antagonists include dexamethasone, prednisolone, RU-24858, Compound A, AL-438, LGD-5552, ZK-216348, Mapracorat (ZK-245186), C108297, MK-5932, Org 214007-0, PF-802, Fosdagrocorat, Compound 10 and derivatives and analogues thereof as described, for example in Pharmacology & Therapeutics, Volume 152, August 2015, Pages 28-41, which is specifically incorporated by reference. In specific embodiments, GR antagonists from Clark, Current Topics in Med. Chem., 2008, 8(9):813-838 are included or excluded.

In some embodiments, one or more of these antagonists is excluded. It is further contemplated that instead of a GR antagonist, the patient is administered a GR inhibitor. In some embodiments, a subject or a subject's cells are not given dexamethasone. In some embodiments, Compound A can be administered to the patient as or instead of a GR antagonist because Compound A is a GR inhibitor. Compound A, also known as CpdA, is a compound with anti-inflammatory and anti-cancer activity (see Lesovaya et al., *Oncotarget* 2015 Oct. 13; 6(31):30730-30744, 2015 and S. J. Desmet, N. Bougarne, L. Van Moortel, L. De Cauwer, J. Thommis, M. Vuylsteke, D. Ratman, R. Houtman, J. Tavernier & K. De Bosscher Scientific Reports 7, Article number: 8063 (2017), which are hereby incorporated by reference). Compound A influences gene regulation of the dexamethasone-activated glucocorticoid receptor by alternative cofactor recruitment. Compound A does not bind to ligand pocket but is a GR inhibitor.

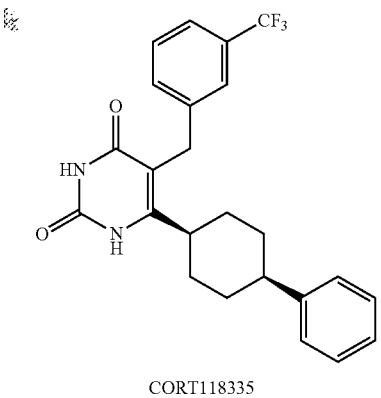 [SMILES: O=c1[nH]c(=O)c(Cc2cccc(C(F)(F)F)c2)c([C@H]2CC[C@@H](c3ccccc3)CC2)[nH]1]

CORT118335

In additional embodiments, a patient is administered an Hsp90 inhibitor. Hsp90 inhibitors block the proper folding of GR so that GR loses most of its transcriptional activity. Therefore Hsp90 inhibitors, by preventing Hsp90 from complexing with GR, blocks GR function in an indirect way. Examples of Hsp90 inhibitors include, but are not limited to, geldanamycin, ganetespib, radicicol, 17-N-Allylamino-17-demethoxygeldanamycin/tanespicmycin/17AAG (BMS), 17-DMAG, herbimycin A, novobiocin sodium (U-6591), 17-GMB-APA-GA, macbecin I, CCT 018159, gedunin, PU24FCl, PU-H71, PU-DZ8, PU3, AUY922 (Novartis), HSP990 (Novartis), retaspimycin hydrochloride/IPI-504 (Infinity), BIIB021/CNF2024 (Biogen Idec), STA-9090 (Synta), IPI-493 (Infinity), SNX-5422/mesylate (Pfizer), BIIB028 (Biogen Idec), KW-2478 (Kyowa Hakko Kirin), AT13387 (Astex), XL888 (Exelixis), MPC-3100 (Myriad), ABI-010/nab (nanoparticle, albumin bound)-17AAG (Abraxis). It is specifically contemplated that one or more of the Hsp90 discussed herein, in the incorporated references, or known to those of skill in the art may be excluded in certain embodiments. In certain embodiments, Hsp90 inhibitors used herein may not be a GR antagonist or may not bind to GR, even may not downregulate GR expression.

It is specifically contemplated that any embodiment discussed with respect to a GR antagonist may be implemented with an Hsp90 inhibitor instead of or in addition to one or more GR antagonists. In some embodiments, more than one Hsp90 inhibitor is used.

In some embodiments, one or more genes may be directly or indirectly measured or assayed for expression. Methods include directly measuring or assaying the level of expression which refers to measuring or assaying a sample to determine the level of gene expression (protein or transcript) in a cell. Indirectly obtaining the level of expression includes measuring or assaying expression or activity of a gene or protein that correlates with expression of the gene. In some embodiments, the level of expression of a GR-antagonist gene can be indirectly obtained by measuring or assaying expression of GR or a GR-responsive reporter gene, which refers to a gene whose expression is affected in a dose-dependent manner by GR expression or activity. Expression refers to either protein expression or RNA (transcript) expression unless otherwise specified. In specific embodiments, level of RNA transcripts is the level of expression being measured, compared, and/or evaluated. Methods may involve either type of expression and a variety of assays are well known to those of skill in the art. For example, quantitative PCR may be performed to obtain RNA expression levels. An Affymetrix chip also provides information regarding RNA expression levels. Alternatively, reagents to detect protein expression levels may be employed in embodiments. Methods may involve probes, primers, and/or antibodies that are specific to the GR-antagonist responsive gene product in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, or MAOA. In some embodiments, a GR antagonist-responsive gene is one whose expression is directly affected by GR through a GR-responsive element in its transcriptional control region.

In some embodiments, there is a step of assaying or measuring the activity level of glucocorticoid receptor (GR) in a biological sample from the patient containing breast cancer cells. ("breast cancer sample"). In some embodiments, the biological sample is a biopsy from the breast or from the lymph nodes that are adjacent to the breast. In other embodiments, the biological sample is comprises cells that are not breast cells and may be obtained from an organ or tissue other than the breast. In some embodiments, the biological sample comprises metastasized breast cancer cells. As discussed above, the activity level of GR can be obtained directly or indirectly. It is specifically contemplated that levels of glucocorticoid activity or expression refers to activity or expression of GR a, GR R, or both. Unless specifically stated otherwise, the terms "glucocorticoid receptor" or "GR" refer to both forms.

In some embodiments, methods include identifying the patient as having or not having a risk factor for cancer recurrence based on the levels of ER and GR expression. Methods may involve categorizing the patient as ER+ or ER− based the level of estrogen receptor expression and a predetermined threshold value for ER expression. The term "ER+" refers to a classification of ER expression that indicates the patient expresses estrogen receptor in breast cancer cells at or above a certain level. The term "ER−" refers to a classification of ER expression that indicates the patient expresses estrogen receptor at a relatively low level in breast cancer cells, meaning at or below a certain level. In certain embodiments, the patient being tested and/or treated has triple-negative breast cancer. In some cases, the patient has been tested for TNBC and/or determined to have TNBC.

In some embodiments, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

In certain embodiments, the predetermined threshold value for expression identifies a patient as having increased expression if the patient's expression level for that particular GR responsive gene is in the $25^{th}$ percentile or greater compared to a normalized sample. This means the patient may be designated as having a level of expression that is at or above 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as GR antagonist responsive if the patient's expression level for exactly, at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, or 462 (or any range derivable therein) GR antagonist responsive genes is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. The higher the percentile, the higher the relative expression level. A patient may be considered GR-antagonist non-responsive if a certain number of genes do not have a level of expression that are within or above the percentile of patients who are GR-antagonist responsive. In certain cases, the score for a patient may be calculated based on the patient's expression profile and it may be compared to other patients deemed GR-antagonist responsive, GR-antagonist non-responsive, at risk for recurrence and/not at risk for recurrence.

In some embodiments, after the expression levels of a panel of GR-responsive genes is measured, the results may be evaluated to determine the likelihood a patient will experience recurrence or be responsive to a cancer treatment. The patient may be classified as having a percent chance or being among a percentile of patients of having recurrent cancer, not having recurrent cancer, being responsive to a cancer treatment or not being responsive (or being non-responsive) to a cancer treatment.

Methods may involve the use of a normalized sample or control that is based on one or more breast cancer samples that are not from the patient being tested. In some embodiments, a control level of expression may be used. A control level of expression is determined based on average levels of expression from a plurality of patients, such as more than 10, 20, 30, 40, 50, 60, 70, 80, 90, 100 or more patients (or any range derivable therein). For example, a control level of expression can be the level of expression, with or without standard deviation(s), that is a level of expression for patients that are GR-antagonist responsive or who are GR-antagonist nonresponsive (meaning the level of expression of a particular gene identified herein does not change more than a certain specified level when exposed to a GR antagonist). A control level may be a threshold level. In some embodiments, measured levels of expression are compared to control levels. In some embodiments, one or more control levels is the altered expression level from a control that is a GR antagonist-reversible transcriptional target. A "GR-inhibitor-reversible transcription target" refers to a gene whose transcription level can be reversibly and detectably altered in the presence of a GR inhibitor compared to the absence of the GR inhibitor. In some embodiments, the GR inhibitor is a GR antagonist or a GR modulator as discussed in the Examples. In other embodiments, one or more control levels is the unaltered or unaffected expression level from a GR inhibitor-reversible transcriptional target; the unaltered or unaffected expression level is a level observed in a GR inhibitor-reversible transcriptional target in a tumor cell or tissue that is non-responsive to the GR inhibitor or is a "housekeeping gene" that is not subject to changes in expression from a GR inhibitor. Exemplary housekeeping genes include but are not limited to ACTB, GAPDH, GUSB, RPLP0, and TFRC. The level(s) of expression of an appropriate housekeeping gene or an "unaltered or unaffected" expression level means a normalized level of expression that is within a standard deviation for the type of measurement taken.

In some embodiments, the level of expression of a GR responsive gene relative to housekeeping genes exceeds a fixed ratio (e.g., 1.3 fold) to be considered induced or increased. In other embodiments, the level of expression of a measured gene is at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100-fold or more (or any range derivable therein).

In certain embodiments, a level of expression of a gene is increased compared to the control or a threshold level of a control. In other embodiments, a level of expression of a gene is increased compared to the control or a threshold level of a control. In certain embodiments, a level of expression of a gene is decreased compared to the control or a threshold level of a control. In other embodiments, a level of expression of a gene is decreased compared to the control or a threshold level of a control. In further embodiments, a level of expression of a gene is altered compared to the control or a threshold level of a control. The increase, decrease, or alteration may be about, at least about, at most about a difference of 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 percent or fold (or any range derivable therein). In certain embodiments, the expression level is similar, which means the levels of expression are within the error margins of each other.

In some embodiments, the level of expression of a GR responsive gene relative to housekeeping genes is below a fixed ratio (e.g., 0.67 fold) to be considered decreased or repressed. In other embodiments, the level of expression of a measured gene is below 0.7, 0.65, 0.60, 0.55, 0.50, 0.45, 0.4, 0.35, 0.3, 0.25, 0.2, 0.15, 0.1-fold or less (or any range derivable therein), for example, as compared to expression in the absence of a GR antagonist.

In certain embodiments, the overall expression score will be a function of GR-responsive gene expression levels. In some embodiments, an expression level for each gene measured is normalized to one or more housekeeping genes. In further embodiments, a signature risk for recurrence would be calculated for the patient based on the results of measuring expression levels from one or more genes in any of Tables S2, S3, and/or S4. In some embodiments the signature risk of an individual patient recurrence would be the weighted sum of this expression. In certain embodiments, this would be the risk recurrence score for the patient.

In some embodiments, there are methods comprising (a) determining expression level of one or more GR-responsive genes; (b) comparing the expression level(s) from step (a) with a cut-off value determined from a plurality of corresponding expression level(s) from a plurality of control samples; (c) determining a risk score and treating the patient accordingly.

Embodiments may also include where the patient is treated with more than one type of cancer therapy. Any method may also include treating the patient for breast cancer, which may include directly administering or providing a cancer therapy. In some embodiments, a practitioner or doctor may prescribe a cancer therapy that the patient administers to herself or himself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's expression profile, or the medical practitioner may be aware only that the test indicates directly or indirectly that the test reflects that the patient can be treated with a GR antagonist (or GR inhibitor) with or without other cancer therapy.

Embodiments also concern kits to determine the expression level of one or more GR-antagonist responsive genes such as any gene on Tables S2, S3 and/or S4.

Other embodiments include a computer readable medium having software modules for performing a method comprising the acts of: (a) comparing the expression levels of GR antagonist responsive genes obtained from a patient's breast cancer sample with a reference or control; and (b) providing an assessment of responsiveness of breast cancer cells to GR antagonism to a physician for use in determining an appropriate therapeutic regimen for a patient. In further embodiments, the computer readable medium further comprises a software module for assessing triple negative status of the patient's breast cancer sample.

Computer systems are also included. In some embodiments, they have a processor, memory, external data storage, input/output mechanisms, a display, for assessing expression levels of GR-antagonist responsive genes, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to ER status or triple negative status more generally. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise a glucocorticoid receptor antagonist (or GR inhibitor) and a chemotherapeutic.

In other embodiments, there are methods for treating breast cancer in a patient comprising administering to the patient an effective amount of glucocorticoid receptor antagonist (or GR inhibitor) and a chemotherapeutic.

In further embodiments, methods are provided for treating chemotherapy-insensitive breast cancer cells comprising administering to a breast cancer patient an effective amount of a glucocorticoid receptor antagonist (or GR inhibitor) followed by chemotherapy.

Other methods include methods for treating breast cancer in a patient comprising: a) administering radiation or at least a first chemotherapeutic to the patient; b) subsequently administering an effective amount of a glucocorticoid receptor antagonist (or GR inhibitor) to the patient; and, c) administering radiation again or at least a second chemotherapeutic to the patient after the glucocorticoid receptor antagonist (or GR inhibitor) is administered to the patient.

In some embodiments, there are methods for treating breast cancer in a patient comprising: a) administering an effective amount of a glucocorticoid receptor antagonist or GR inhibitor to the patient, wherein the patient expresses altered levels of GR-responsive genes as compared to prior to administration of the GR antagonist or GR inhibitor; b) then administering an effective amount of radiation or at least one chemotherapeutic.

It is contemplated that in methods described herein, breast cancer cells may undergo apoptosis following treatment set forth herein. Moreover, in some embodiments, the combination of a glucocorticoid receptor antagonist (or GR inhibitor) and an anticancer agent or compound induces more apoptosis than treatment with just the anticancer treatment alone. In other methods, it is specifically contemplated to exclude treatment with a synthetic glucocorticoid, such as dexamethasone.

In some embodiments, a patient had been previously treated with an anti-cancer therapy, such as radiation, hormone(s), chemotherapy, or immunotherapy (or a combination or multiple therapies thereof). In certain embodiments, a first anti-cancer therapy prior to therapy with glucocorticoid receptor antagonist (or GR inhibitor) was last administered more than two weeks prior to the glucocorticoid receptor antagonist (or GR inhibitor) or its combination with a second anti-cancer therapy. In certain embodiments, this first anti-cancer therapy that does not include a glucocorticoid receptor antagonist (or GR inhibitor) was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist (or GR inhibitor). Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®. In certain embodiments, the patient has been administered or continues to be administered tamoxifen as part of treatment, which may be before, after, or during treatment with a GR antagonist or GR inhibitor.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

Methods involve treating breast cancer, particularly a chemo-resistant breast cancer, with a combination of therapies that includes a glucocorticoid receptor antagonist and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan®), daunorubicin, docetaxel (Taxotere®), doxorubicin (Adriamycin®), epirubicin (Ellence®), fluorouracil (also called 5-fluorouracil or 5-FU), gemcitabine, eribulin, ixabepilone, methotrexate, mitomycin C, mitoxantrone, paclitaxel (Taxol®), thiotepa, vincristine, or vinorelbin, or a combination of these agents. In other embodiments, therapy with a glucocorticoid receptor antagonist is combined Herceptin®, radiation, chemotherapeutic(s) and radiation, a combination of chemotherapeutics, or a combination of one or more chemotherapeutic agents and Herceptin®. In additional embodiments, treatment may involve a biological therapy. Biological therapy could be an immune pathway modulator either alone or in combination with LAG3 inhibitor, IDO inhibitor, CD137 inhibitor, CD40 inhibitor, CSF1R inhibitor, NOTCH inhibitor, gamma secretase inhibitor, STAT3 inhibitor, and/or adenosine receptor inhibitor.

It is contemplated that in some embodiments of the combination therapy the glucocorticoid receptor antagonist (or GR inhibitor) is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist (or GR inhibitor) is administered within 2 hours, 12 hours or 24 hours of administration of an anticancer agent or compound (or a combination of such agents or compounds).

It is specifically contemplated that treatment may continue or be repeated. In some embodiments, once treated with the combination of a glucocorticoid receptor antagonist (or GR inhibitor) and at least one anticancer agent or compound, all or part of the treatment may be repeated alone or in combination with a different anticancer agent or compound.

In certain embodiments, the glucocorticoid receptor antagonist or GR inhibitor is administered prior to as the other agent or therapy included in the combination therapy. In certain embodiments, the glucocorticoid receptor antagonist or GR inhibitor is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist or GR inhibitor is given prior to administration of the anticancer agent or compound but that the glucocorticoid receptor antagonist or inhibitor is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist or inhibitor is administered up to three days prior to administering the anticancer agent or compound.

Additionally or alternatively, the glucocorticoid receptor antagonist or inhibitor is administered after administration of the other agent or therapy included in the combination therapy. In certain embodiments, the glucocorticoid receptor antagonist or inhibitor is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist or inhibitor is given after to administration of the anticancer agent or compound; such administration may be repeated. As discussed throughout, the anticancer agent or compound may be in a combination of such agents or compounds. In certain embodiments, the glucocorticoid receptor antagonist or inhibitor is administered up to three days after administering the anticancer agent or compound.

In certain embodiments, the glucocorticoid receptor antagonist (or GR inhibitor) or anticancer agent or compound are administered after the patient has been tested for GR-antagonist responsiveness.

In certain embodiments, the breast cancer is an unresectable breast cancer. In further embodiments, the breast cancer is inflammatory breast cancer.

It is specifically contemplated that in some methods, dexamethasone has not been administered to the patient within 24 hours of administration of the glucocorticoid receptor antagonist.

Compositions are contemplated to include a glucocorticoid receptor antagonist (or GR inhibitor) and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death due to disease of said patient over a predetermined period of time, e.g., over a period of 5 years.

The term "recurrence" refers to the detection of breast cancer in form of metastatic spread of tumor cells, local recurrence, contralateral recurrence or recurrence of breast cancer at any site of the body of the patient after breast cancer had been substantially undetectable or responsive to treatments.

As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D. High NR3C1 (GR) expression is associated with worse outcome in TNBC subtypes. Kaplan-Meier estimates of relapse-free survival in patients in the top quartile (versus all others) of tumor NR3C1 expression (125). NR3C1 expression association with RFS was analyzed in TNBCs classified (4) as (A) basal-like 1, (B) basal-like 2, (C) mesenchymal, (D) luminal AR.

FIGS. 2A-B. GR activation inhibits chemotherapy-induced cytotoxicity of cultured TNBC cells and selective GR antagonism increases sensitivity to chemotherapy in vivo. (A) MDA-MB-231 and SUM-159-PT cells were treated with paclitaxel alone (Pac, 10 nM), with Vehicle, Dex (100 nM), Dex/Pac, or C297(1 M)/Dex/Pac. C297 restored cytotoxic sensitivity at 96 hours (MDA-MB-231) and at 72 hours (SUM-159-PT) following Pac. The bars represent the average percentage cell death of n=3 independent experiments and error bars represent standard error of the mean (S.E.M). *=p value<0.05 and **=p<0.01 (two-sample Student's t-test) when compared to Dex/Pac. (B) MDA-MB-231 tumor xenograft re-growth is significantly inhibited by C297 (20 mg/kg/day) pre-treatment one hour prior to pac (10 mg/kg/day) compared to pac alone. Arrows refer to administration of pac/Veh +/−C297/Veh. Pac-treated tumor re-growth was significantly smaller than vehicle, p<0.05, while C297/paclitaxel versus paclitaxel alone delayed post-treatment tumor re-growth significantly. The dotted line represents a 6× increase in re-growth of tumor volume; time to tumor re-growth to this size was 18d (Veh), 27d (Pac), and 40d (Pac/C297). The asterisk (*) represents p<0.05, comparing C297/Pac to Pac alone. Both C/297 vs Pac and Pac alone vs Veh were significantly different based on a repeated measures ANOVA and the Holm-Sidak post-hoc significance test (Veh/Veh n=3, Veh/Pac n=6 and C297/Pac n=9).

FIGS. 3A-C. Differentially expressed GR target genes following GR antagonism. Genome-wide gene expression profiling was performed on MDA-MB-231 cells treated with GC (Dex) or GC/antagonist. (A) Total number of up- and downregulated genes by Dex or Dex/GR inhibitor treatment (relative to vehicle); (B) Subset of Dex-regulated genes (≥1.3-fold Dex vs. vehicle) reversed by C297 and/or Mif at 4, 8, and 12h by ≥25 percent change. (C) GR antagonist-identified genes ((B), n=3,066) overlapped with genes (n=5, 170) that were differentially expressed between GR-high versus GR-low primary tumors (56). N=462 genes were overlapped.

FIGS. 4A-C. GR chromatin association is altered by concomitant treatment with a GR antagonist. (A) Genome-wide GR peaks and associated genes annotated to TSSs +/−100 kB of these peaks; (B) GR chromatin association with transcription factor response elements (REs) following Dex and GR antagonist treatment reveals significant changes in GR enrichment at GREs, AP1 and ELK REs compared with Dex alone (CentriMO); C) GR chromatin association in proximal promoter regions (0-3kb from the TSS) is diminished following Dex/Mif or Dex/C297 treatment while more distal GR peak association is proportionally increased.

FIGS. 6A-D. Patients with above-median expression of the 74-gene GR activity signature (GRsig) have significantly decreased relapse-free survival. Genes in the GRsig were selected from among the n=462 tumor-relevant and antagonist-reversed Dex-regulated genes based on their univariate association with RFS in the Discovery cohort (HR≥1.5 or HR≤0.67; and p<1e-5). (A) Summary of GRsig genes (top line) and their Dex-mediated up- and downregulation, and the subset of GRsig genes that are putative direct GR target genes (middle line) with loss of GR peak with Dex/antagonist treatment (bottom line). (B) List of individual GRsig genes, separated by their Dex-mediated up- or down-regulation with bolded gene names indicating putative direct GR target genes. (C, D) Kaplan-Meier estimates showing that the above-median GRsig expression (versus all others) is associated with RFS in both the Discovery and Validation cohorts.

FIGS. 7A-B. Ligand displacement GC from the GR LBD. Fluorescent dexamethasone (F-Dex) was bound to recombinantly expressed GR LBD and GR ligands Dex, Mif, Cortisol, C335, C297, CpdA, and negative control DHT were titrated in at increasing concentrations. (A) Fluorescence polarization was measured, and the data were fitted to determine (B) Ligand concentrations of half-maximal FP signal. Triplicate FP measurements were scaled to percent maximal FP and averaged for each ligand concentration. Dose response curves were estimated using GraphPad Prism using the log(inhibitor) vs. normalized response curve equation. We were able to fit data for ligands (Dex, Mif, cortisol, C335, C297) but not for CpdA and negative control DHT, suggesting that CpdA does not bind the GR LBD. Error bars are standard error of the mean.

FIGS. 8A-B. Monotherapy is not cytotoxic in vitro and in vivo. The selective GR antagonist C297 was chosen to test increased TNBC cell sensitivity to paclitaxel, and monotherapy of C297 was determined to be not cytotoxic (A) in vitro using the SRB assay and (B) in vivo TNBC tumor-bearing mice. In vitro assay plotted bars represent the average percentage cell death of n=3 independent experiments and error bars represent the standard error of the mean (S.E.M). *=p value<0.05 and **=p<0.01 (two-sample Student's t-test) when compared to Veh. In vivo change from initial tumor volume is shown, with significance reported from a repeated-measures ANOVA the Holm-Sidak post-hoc significance test (n=2 C297/Veh, versus vehicle control n=3).

FIGS. 9A-C. Mif and C297 antagonize Dex-regulated gene expression in MDA-MB-231 cells. (A) Venn diagrams of unique and overlapped significantly up- and downregulated genes in Dex (red), Dex/Mif (blue), and Dex/C297 (green) at any timepoint (+/−1.3 fold-change versus vehicle). Venn diagrams were generated using the BioVenn application. (B) Principal components analysis (PCA) of significantly expressed (+/−1.3 fold-change versus vehicle) expression signatures of Dex (red), Dex/Mif (blue), and Dex/C297(green) at 4, 8, and 12h using Q-mode singular value decomposition PCA function in R. (C) A heatmap demonstrating relative gene expression (compared to vehicle) of probes for the n=3,066 genes that are significantly expressed in the Dex treatment (at any timepoint) and are commonly antagonized by at C297 and Mif by at least 25%. Row (probes) and column (treatment) clustering was performed using the one-minus Pearson correlation with complete linkage in the Morpheus program (Broad Institute).

FIGS. 10A-B. Dex-induced genome-wide GR peak locations (ChIP-seq) are altered by the addition of Mif or C297. A) Relative loss of n=8,448 genome-wide Dex-GR peaks in the Dex/Mif and Dex/C297 treatments. Heatmaps, generated using SeqPlot, of the genome-wide Dex-GR peaks, centered on the peak with +/−1kb flanking regions. When comparing vehicle-subtracted Dex/Mif or Dex/297 peaks with Dex peaks, numbers of overlapping regions (by at least 1 bp) are shown below the Dex/Mif and Dex/297 heatmaps. B) Genome-wide GR peak locations in Dex, Dex/Mif, and Dex/297 treatments were examined using ChIPseeker near the GR peak-associated TSS. Enrichment of Dex-GR was observed within nearest to the TSS (within +/−3kb), while loss of GR enrichment in this region was observed in Dex/Mif and Dex/297 treatments.

FIGS. 11A-D. GR antagonists inhibit Dex-induction of GR target genes, whereas the transient knockdown two target genes (MCL1 and NNMT) restores paclitaxel cytotoxicity in the presence of Dex. GR target gene steady-state mRNA levels in the presence of 100 nM Dex, Dex/Mif, or Dex/C297 in A) MDA-MB-231 and B) SUM159PT cells. Graphs are one replicate, representative of n=3. Average fold-change of transcript expression over vehicle is shown with an asterisk (*) representing p<0.05, Student's t-test with Welch's correction; C) Cytotoxicity of paclitaxel (x nM), tested via the SRB assay, was measured in siControl, siNNMT, or siMCL1 pool-transfected MDA-MB-231 cells, bars are average cytotoxic index of n=3 experiments, asterisks(*) represent p<0.05, Student's t-test; D) Efficiency of knock-down was tested using Q-RT-PCR for the respective gene (n=2).

FIGS. 12A-B. Association of NR3C1 expression with RFS in the Validation Cohort. Kaplan-Meier estimates of RFS in the Validation Cohort among patients with (A) above-median (versus all others) and (B) top-quartile (versus all others) of NR3C1 expression.

FIG. 13. GR antagonists diminish cell survival and invasive functions while promoting apoptosis.

FIG. 14: Supplementary Table S1
FIG. 15: Supplementary Table S2
FIG. 16. Supplementary Table S3

DETAILED DESCRIPTION OF THE INVENTION

Figure 5:
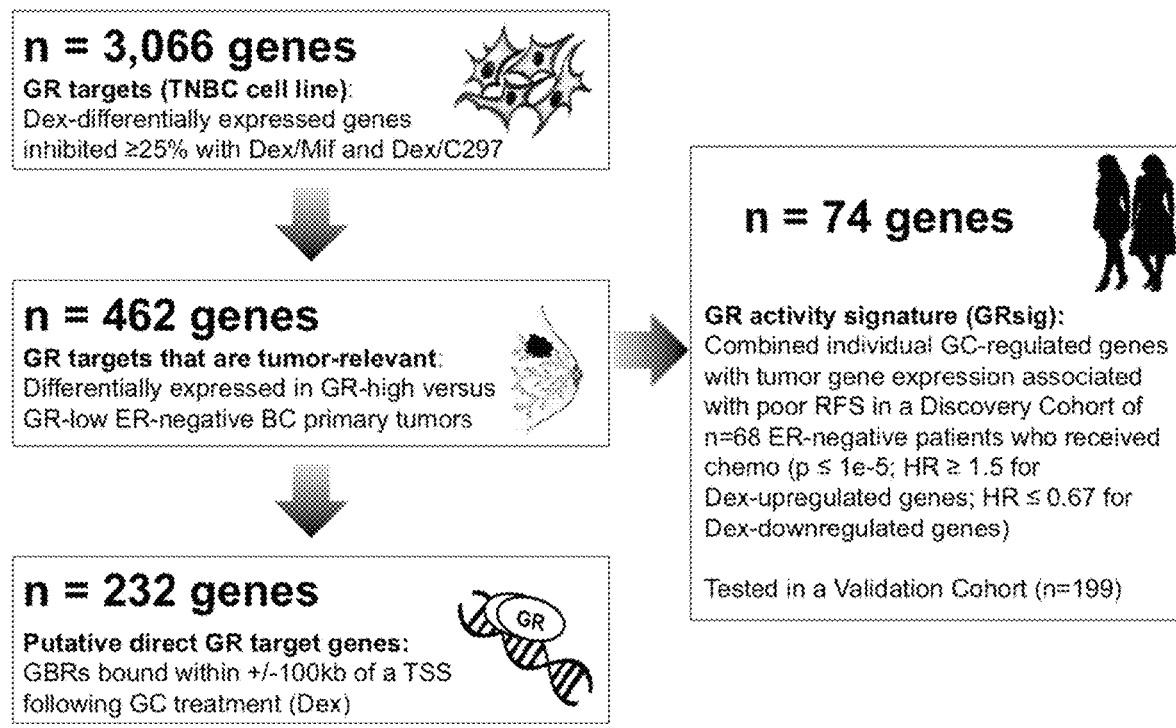
FIG. 5. Identification schema for the GR activity signature (GRsig). Genes that were Dex-regulated and inhibited at least 25% by Mif and C297 were identified in MDA-MB-231 cells (n=3,066). Next, the subset of genes also differentially expressed in the same direction in GR-high versus GR-low ER-negative BCs was identified (n=462). GR ChIP-seq determined putative GR direct target genes as having GR associated within 100 kb of the gene TSS (n=232). A GR "activity signature" (GRsig) was identified based on their univariate association with RFS (HR≥1.5 or HR≤0.67; and p≤1e-5) in the Discovery cohort of early-stage ER-negative BC patients with adjuvant chemotherapy. The 74-gene GRsig was applied to the Discovery and an independent Validation cohorts of early-stage patients treated with adjuvant chemotherapy.

Embodiments are based on several GR activity signatures using GR-mediated gene networks and then identified genes whose expression changes were reversed by GR antagonism. GR transcriptional activity was antagonized with the steroidal GR/PR antagonist mifepristone (Mif) or the highly-selective non-steroidal GR modulator CORT 108297 (C297) (62). Studies were performed using GR antagonists in the context of glucocorticoid (GC)-activated GR to mimic cortisol-activated GR in patient tumors. This experimental design allowed identification of antagonist-sensitive GC-mediated GR pathways for both mechanistic insight and identification of at least one GR activity signature (GRsig) for improved patient stratification.

GR is a widely active transcription factor with different tissue-specific activities, and in the context of TNBC, GR is likely to regulate many genes that contribute to recurrence. A panel of GR target genes can be a better indicator of GR activity in TNBC than GR expression alone. The analyses of antagonist-modulated GR gene expression in TNBC cells was combined with gene expression data from primary ER-negative BCs to identify the GRsig of n=74 genes associated with poor prognosis after adjuvant chemotherapy. The GRsig was validated in an independent dataset. The GRsig and/or other panel signatures identified herein can be used to identify individual early-stage TNBC patients with a relatively increased risk of relapse. Moreover, adding GR antagonism to adjuvant chemotherapy could reduce GR activity, increase chemotherapy efficacy, and improve clinical outcome in poor-prognosis ER-negative BC patients.

I. Glucocorticoid Receptors and Other Hormone Receptors

Intracellular receptors (IRs) form a class of structurally-related genetic regulators scientists have named "ligand dependent transcription factors" (R. M. Evans, Science, 240:889, 1988). Steroid receptors are a recognized subset of the IRs, including androgen receptor (AR), progesterone receptor (PR), estrogen receptor (ER), glucocorticoid receptor (GR), and mineralocorticoid receptor (MR).

Glucocorticoid receptor (GR) is a corticosteroid receptor with both transcription factor and chromatin remodeling functions (17-23). The role of GR in endocrine physiology and metabolism is cell-type specific (24), and its role in cell survival appears to be cancer subtype specific as well. For example, GR activation is pro-apoptotic in lymphoid (25, 26) and bladder (27) malignancies, whereas GR activation is anti-apoptotic and is associated with relapse in other cancers (28-39), including ER-negative BC (40-48). Interestingly, in ER-positive BC, GR/ER crosstalk appears to account for an improved patient outcome (49-54), highlighting GR's context-dependent function. Our laboratory and others have reported that higher tumor GR transcript (52) and protein (55) expression in early-stage ER-negative tumors is associated with shorter relapse-free survival (RFS). In a retrospective meta-analysis of tumor gene expression from n=354 ER-negative early-stage BC patients, high GR transcript expression (NR3C1, top quartile) was associated with poor long-term RFS regardless of whether patients received adjuvant chemotherapy (52). Furthermore, GR antagonism has been demonstrated to sensitize cells to chemotherapy-induced cytotoxicity in ovarian (32, 36, 38), prostate (34, 35, 39, 56), and TNBC (43, 44). A Phase I clinical trial of mifepristone (300 mg/day) administered to BC patients before weekly nab-paclitaxel treatment has established the safety and tolerability of this combination (57). Together, these data suggest that GR transcriptional activity plays a role in BC aggressiveness and chemoresistance, and that GR antagonism is a potential therapeutic strategy.

While GR/NR3C1 cellular expression levels are predicted to correlate with GR activity (as has been shown for ER (100)), many factors contribute to an individual tumor's GR activity level. The relative expression of nuclear receptor coregulators and cooperating transcription factors influence cell-type specific nuclear receptor activity (101-105). Other modifiers of GR activity include post-translational GR modification (106, 107) and the allosteric effect of chromatin landscape (108-110). These variables result in highly specific networks of GR target genes depending upon cellular context. For example, it was previously reported that GR activation in ER+BC increases the expression of pro-differentiating genes (57). However, as expected in this study of ER-negative BC, these pro-differentiating genes are not among the n=462 tumor-derived and GC-regulated genes shown in FIG. 3C. The ER-negative GRsig derived here likely reflects gene expression specifically observed in early-stage ER-negative BCs.

Estrogen, mediated through the estrogen receptor (ER), plays a major role in regulating the growth and differentiation of normal breast epithelium (Pike et al. Epidemiologic Reviews (1993) 15(1):17-35; Henderson et al. Cancer Res. (1988) 48:246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., Annals of Oncology 11(8): 1057 (2000)). Thus, ER negative and ER positive breast cancers are two distinct disease entities rather than phenotypic variations of the same disease.

Relatively increased expression of these genes in primary ER-negative human breast tumors is associated with high GR expression and with an earlier relapse in ER-negative breast cancer patients (described herein). Activation of the glucocorticoid receptor (GR) in epithelial cells has been shown to initiate an anti-apoptotic (i.e., cell survival) signaling pathway that prevents breast (Wu et al, 2004) and ovarian cancer (Melhem et al, 2009) cell death in vitro and in vivo (Pang et al, 2006). Blocking or antagonizing GR activation with a GR antagonist such as mifepristone reverses cell survival signaling pathways initiated by the GR (Moran et al., 2000). Other GR antagonists (e.g., dexamethasone oxetanone) also reverse GR-mediated cell survival and potentiate apoptosis in response to cell stressors such as growth factor withdrawal (Mikosz et al, 2001). The mechanism(s) whereby GR activation protects from cell death includes the transcriptional upregulation of genes encoding anti-apoptotic proteins such as SGK1, MKP1, MCL1, and BIRC3. However, experiments with a glucocorticoid receptor antagonist, RU486, in conjunction with dexamethasone did not increase the number of apoptotic cells induced by paclitaxel, compared to paclitaxel alone (Wu et al., 2004).

II. GR Antagonists and Inhibitors

The genes identified as GR-responsive were evaluated in the context of one or more GR antagonists. Moreover, embodiments concern treatment with one or more GR antagonists for cancer. A number of GR antagonists have been identified. GR antagonists include, but are not limited to, beclometasone, betamethasone, budesonide, ciclesonide, flunisolide, fluticasone, mifepristone, mometasone, and triamcinolone.

A recently completed Phase-I clinical trial of Mif given before administration of nab-paclitaxel to decrease anti-apoptotic tumor cell gene expression found that combining GR antagonism with chemotherapy appears to be safe and tolerable (61). A Phase-I clinical trial of the highly-selective GR antagonist CORT125134 [an azadecalin structurally related to C297(115)] in combination with nab-paclitaxel in solid tumors is currently underway (NCT02762981). Also, a Phase-II randomized clinical trial of Mif (versus placebo) with nab-paclitaxel in patients with advanced-stage TNBC has been recently activated (NCT02788981). While there is some concern that a potent GR antagonist might increase chemotherapy-induced side effects (because Dex is used to reduce chemotherapy-associated nausea), thus far, the Phase-I studies only suggest a potential for increased cytopenias (61). This will be further investigated in the upcoming randomized Phase-II trial of nab-paclitaxel +/− Mif.

III. Biomarkers and Evaluating Levels of Biomarkers

Biomarkers for identifying effective treatment for human breast cancer patients are provided. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of ER, GR, or ER and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene is preferably achieved by dividing the expression level of the individual marker gene to be normalized by the respective individual median expression of this marker genes, wherein said median expression is preferably calculated from multiple measurements of the respective gene in a sufficiently large cohort of test individuals. The test cohort preferably comprises at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, preferably more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of the gene in the cell type is at least about 2-fold, 5-fold, 10-fold, 100-fold, 1000-fold, or 10000-fold higher (or any range derivable therein) than in a reference cell type, or in a mixture of reference cell types. Reference cell types include non-cancerous breast tissue cells or a heterogenous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:
1. The individual marker genes are compared to their respective threshold levels.
2. The number of marker genes, the expression level of which is above their respective threshold level, is determined.
3. If a marker genes is expressed above its respective threshold level, then the expression level of the marker gene is taken to be "above the threshold level".

"A sufficiently large number", in this context, means preferably 30%, 50%, 80%, 90%, or 95% of the marker genes used.

In certain aspects, the determination of expression levels is on a gene chip, such as an Affymetrix™ gene chip. In other embodiments, RNA sequencing is employed.

In another aspect, the determination of expression levels is done by kinetic real time PCR.

In certain aspects, the methods can relate to a system for performing such methods, the system comprising (a) apparatus or device for storing data on regarding expression levels of one or more GR-antagonist responsive genes of the patient; (b) apparatus or device for determining the expression level of at least one marker gene; (c) apparatus or device for comparing the expression level of the first marker gene with a predetermined first threshold value; (d) apparatus or device for determining the expression level of at least one second marker gene; and (e) computing apparatus or device programmed to provide treatment with a GR antagonist if the data indicates altered expression levels of said first marker gene or activity as compared to the predetermined first threshold value and, alternatively, the expression level of said second marker gene is above or below a predetermined second threshold level, wherein the predetermined threshold values are based on expression levels for genes unaltered after exposure to a GR antagonist.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The content of all of these GenBank Accession numbers is specifically incorporated herein by reference as of the filing date of this application.

The following biomarkers are provided for implementation with additional embodiments discussed herein. All of them designate nucleic acid sequences for the particular gene identifier. Nucleic acid sequences related to these gene designation can be found in the Genbank sequence databases. Additional biomarkers include the MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA genes.

One or more of the biomarkers can be used to determine whether a human patient with breast cancer should be treated with one or more GR antagonists or inhibitors (with or without additional cancer therapy) as a therapy. The expression pattern of these biomarkers in breast cancer cells may be used to evaluate a patient to determine whether they are likely to respond to a GR antagonist/inhibitor or likely not to respond to GR antagonist/inhibitor.

The expression levels of breast cancer biomarkers can be compared to reference expression levels using various methods. These reference levels can be determined using expression levels of a reference based on all breast cancer patients or all breast cancer patients determined to be GR antagonist responsive. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03.

0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments of the invention.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect of the present invention, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Preferably, each probe/primer has relatively high sequence complexity and does not have any ambiguous residue (undetermined "n" residues). The probes/primers preferably can hybridize to the target gene, including its RNA transcripts, under stringent or highly stringent conditions. In some embodiments, because each of the biomarkers has more than one human sequence, it is contemplated that probes and primers may be designed for use with each one of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products preferably are carried out when the PCR reactions are in the linear portion of their curves. In addition, relative concentrations of the amplifiable cDNAs preferably are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and 3-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324, 633; 5,384,261; 5,405,783; 5,412,087; 5,424,186; 5,429, 807; 5,432,049; 5,436,327; 5,445,934; 5,468,613; 5,470, 710; 5,472,672; 5,492,806; 5,525,464; 5,503,980; 5,510, 270; 5,525,464; 5,527,681; 5,529,756; 5,532,128; 5,545, 531; 5,547,839; 5,554,501; 5,556,752; 5,561,071; 5,571, 639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween® (polyoxyethylene sorbitol ester) and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween® (polyoxyethylene sorbitol ester), or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween® (polyoxyethylene sorbitol ester)).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies for this invention include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip® by Ciphergen Biosystems Inc. (Fremont, Calif). The ProteinChip® is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip® system detects proteins ranging from small peptides of less than 1000 Da up to proteins of 300 kDa and calculates the mass based on time-of-flight (TOF).

The ProteinChip® biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

a. Breast Cancer Therapy

Certain embodiments are directed to methods of treating breast cancer based on responsiveness to GR antagonism of the breast cancer tissue.

In certain aspects, there may be provided methods for treating a subject determined to have cancer and with a predetermined expression profile of one or more biomarkers disclosed herein.

In a further aspect, biomarkers and related systems that can establish a prognosis of cancer patients with respect to GR antagonist/inhibitor therapy can be used to identify patients who may get benefit of conventional single or combined modality therapy.

In certain aspects, conventional cancer therapy may be applied to a subject wherein the subject is identified or reported as likely responsive to a GR antagonist/inhibitor based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern a glucocorticoid receptor antagonist. In some embodiments, the glucocorticoid receptor antagonist is a selective glucocorticoid receptor antagonist, as set forth in Clark, 2008, which is hereby incorporated by reference. In other embodiments, the glucocorticoid receptor antagonist is a non-selective glucocorticoid receptor antagonist, such as mifepristone. In certain embodiments, the glucocorticoid receptor antagonist is steroidal. In other embodiments, the glucocorticoid receptor antagonist is non-steroidal. A glucocorticoid receptor antagonist includes those in the following classes of chemical compounds: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins, and which are described in more detail in Clark, 2008, which is hereby incorporated by reference. Some embodiments of steroidal antagonists from Clark, 2008 are: RU-486, RU-43044, 11-monoaryl and 11,21 bisaryl steroids (including 11β-substituted steroids), 10β-substituted steroids, 11β-aryl conjugates of mifepristone, and phosphorous-containing mifepristone analogs. Further embodiments of nonsteroidal antagonists from Clark, 2008 are: octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines). Additional specific examples include, but are not limited to the following specific antagonists: beclometasone, betamethasone, budesonide, ciclesonide, flunisolide, fluticasone, mifepristone, mometasone, and triamcinolone. Other examples include those described and/or depicted in U.S. Patent Application Publication 2010/0135956, which is hereby incorporated by reference. Even further examples include ORG-34517 (Merck), RU-43044, dexamethasone mesylate (Dex-Mes), dexamethasone oxetanone (Dex-Ox), deoxycorticosterone (DOC) (Peeters et al., 2008, which is hereby incorporated by reference in its entirety and Cho et al. 2005, which is hereby incorporated by reference in its entirety). In additional embodiments the glucocorticoid receptor antagonist may be CORT 0113083 or CORT 00112716, which are described in Belanoff et al. (2011), which is hereby incorporated by reference. It is specifically contemplated that one or more of the antagonists discussed herein or in the incorporated references may be excluded in embodiments of the invention. It is also contemplated that in some embodiments, more than one glucocorticoid receptor antagonist is employed, while in other embodiments, only one is employed as part of the therapeutic method (though it may be administered multiple times). It is contemplated that the second one may be administered concurrently with the first one or may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, Taxol® (paclitaxel), gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan®), daunorubicin, docetaxel (Taxotere®), doxorubicin (Adriamycin®), epirubicin (Ellence®), fluorouracil (also called 5-fluorouracil or 5-FU), gemcitabine, eribulin, ixabepilone, methotrexate, mitomycin C, mitoxantrone, paclitaxel (Taxol®), thiotepa, vincristine, and vinorelbine.

In some embodiments, the chemotherapeutic agent is any of (and in some embodiments selected from the group consisting of) Adriamycin® (doxorubicin), colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, Taxotere® (docetaxel) and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist or GR inhibitor. Combinations of breast cancer therapeutics include, but are not limited to the following: AT (Adriamycin® (doxorubicin) and Taxotere® (docetaxel)), AC ±T: (Adriamycin® (doxorubicin) and Cytoxan® (cyclophosphamide), with or without Taxol® (paclitaxel) or Taxotere® (docetaxel)), CMF (Cytoxan® (cyclophosphamide), methotrexate, and fluorouracil), CEF (Cytoxan® (cyclophosphamide), Ellence® (epirubicin), and fluorouracil), FAC (fluorouracil, Adriamycin® (doxorubicin), and Cytoxan® (cyclophosphamide)), CAF (Cytoxan® (cyclophosphamide), Adriamycin® (doxorubicin), and fluorouracil) (the FAC and CAF regimens use the same medicines but use different doses and frequencies), TAC (Taxotere® (docetaxel), Adriamycin® (doxorubicin), and Cytoxan® (cyclophosphamide)), and GET (Gemzar® (gemcitabine), Ellence® (epirubicin), and Taxol® (paclitaxel)). In some embodiments trastuzumab (Herceptin®) is administered to a breast cancer patient with a glucocorticoid receptor antagonist, which may be with or without a chemotherapeutic or a combination of chemotherapeutics.

Various combinations with a glucocorticoid receptor antagonist (or GR inhibitor) and an anticancer agent or compound (or a combination of such agents and/or compounds) may be employed, for example glucocorticoid receptor antagonist is "A" and the anticancer agent or compound (or a combination of such agents and/or compounds) given as part of an anticancer therapy regime, is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | | A/B/B/A | B/B/A/A |
| B/A/B/A | B/A/A/B | A/A/A/B | B/A/A/A | | A/B/A/A | A/A/B/A |

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

Other examples of anticancer therapy that may be used in conjunction with GR antagonist (or GR inhibitor) therapy include but are not limited to checkpoint inhibitors such as those that inhibit PD-1 (e.g., Pembrolizumab and Nivolumab), PD-L1 (e.g., Atezolizumab, Avelumab, Durvalumab), or CTLA-4 (e.g., Ipilimumab).

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-.beta., lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E,6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as y-rays, X-rays, and/or the directed delivery of radioisotopes to tumor cells. Proton beam therapy or proton therapy is frequently used for cancer treatment. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a preferred embodiment of the method or use of the invention, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$ M or less, more preferably $10^{-10}$ M or less.

Particularly antibodies for use in the present invention include zalutumumab (2F8), cetuximab (Erbitux®), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

a. Kits

Certain aspects of the present disclosure also encompass kits for performing the methods described herein. They can be prepared from readily available materials and reagents. For example, such kits can comprise any one or more of the following materials: enzymes, reaction tubes, buffers, detergent, primers, probes, antibodies. In a preferred embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, any of the genes listed in Tables S2, S3, and/or S4, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers of the invention. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Materials and Methods for Examples 2-6

Study Design

When applicable, we have included information about the experimental design, sample size, rules for stopping data collection, selection of endpoints, experimental replicates, and randomization for each individual experiment in the Materials and Methods below.

Cell Lines and Reagents

MDA-MB-231 and SUM-159-PT cell lines were validated and tested negative for mycoplasma throughout the course of the experiments. MDA-MB-231 cells were cultured in Dulbelcco's Modified Eagle's Media (DMEM, Lonza), supplemented with 10% fetal bovine serum (FBS, Gemini Bio-Products) and 1% penicillin/streptomycin (Lonza). SUM-159-PT cells were cultured in Ham's F12 Media (Corning), supplemented with 10% FBS and 1% penicillin/streptomycin. Cells were cultured at 37° C. and 5% $CO_2$. Compounds for cell culture studies were acquired and dissolved as follows: Dexamethasone (Sigma) and Mifepristone (Enza) were dissolved into 1 mM stock solutions in ethanol (EtOH, Sigma). CORT108297 (C297, Corcept Therapeutics, Menlo Park, CA), and was dissolved at 1 mM in EtOH. Pharmaceutical-grade paclitaxel (APP Pharmaceuticals) was diluted to 1 mM in EtOH. Compounds for the fluorescent polarization assay were dissolved in dimethyl sulfoxide (DMSO) at 50 mM concentrations, including dexamethasone, mifepristone, CORT108297, CORT118335, dihydrotestosterone (DHT), and Compound A (Enzo Life Sciences). Fluorescein-dexamethasone (Invitrogen) was dissolved in DMSO in black microcentrifuge tubes at a concentration of 20 mM and further diluted as needed in water. For murine xenograft studies, pharmaceutical-grade paclitaxel (APP Pharmaceuticals) was suspended in saline and castor oil so that a 50 μL i.p. injection into a 20-gram mouse would be a 10 mg/kg dose. CORT108297 was dissolved in EtOH and suspended in sesame oil so that a 50 μL i.p. injection into a 20-gram mouse would be a 20 mg/kg dose.

In Vitro GR LBD Expression and Purification

The wild-type GR-LBD (amino acid residues 522-777) was cloned into a pFASTBAC plasmid with a TEV-cleavable 6X-His tag (SEQ ID NO: 1) and used to transform DH10BAC cells to produce bacmid DNA (Thermo Fischer). SF9 insect cells were transfected with recombinant bacmid and virus (collected after 6 days) was amplified prior to protein expression. Protein expression was initiated by infecting log phase SF9 cells with freshly prepared virus (MOI=1) and allowed to ferment for an additional 72 hours at 37° C. in the presence of 1.0 μM Dex. SF9 cells were pelleted at 3,000 RPM at 4° C., and lysed by sonication in a buffer containing 20 mM TRIS pH 8.0, 500 mM NaCl, 5% glycerol, 0.1% CHAPS, 0.25 mM TCEP that was supplemented with protease inhibitors and 1.0 μM Dex. GR-LBD was purified first using Ni-affinity chromatography followed by overnight dialysis with TEV protease to remove the His tag. Extensive dialysis into 20 mM TRIS pH 8.0, 500 mM NaCl, 5% glycerol, 0.1% CHAPS, 0.25 mM TCEP was performed to obtain non-ligand-bound GR LBD. The final protein was obtained using size exclusion chromatography where the protein consistently eluted as a dimer. The purified proteins were concentrated to 5 mg/ml, flash frozen in 50 ul aliquots in $N_2$(l), and stored at −80C.

Ligand Titration Assay Via Fluorescence Polarimetry (FP)

GR LBD was diluted in assay buffer (20 mM TRIS pH 7.5, 50 mM NaCl, 0.25 mM TCEP) to a concentration of 50 nM. After pre-equilibration of GR LBD with both ligand (ranging from concentrations ranging from 0 to 4000 nM) and 10 nM fluorescein-labeled dexamethasone (F-Dex, Life Technologies) for 30 minutes, FP signal was measured using the Beacon 2000 Fluorescence Polarization System (Invitrogen). Triplicate FP measurements were scaled to maximal FP and averaged for each ligand concentration. Dose response curves for each ligand were generated using GraphPad Prism using the log(inhibitor) vs. normalized response curve equation:

$$Y=100/(1+10^{((\text{Log IC50}-X)*\text{HillSlope})})$$

Cell Viability Assay

MDA-MB-231 and SUM-159-PT cells ($n=3\times10^4$) were seeded in 96-well plates. After culturing in DMEM with 10% FBS (for MDA-MB-231) or Ham's F12 with 5% FBS (for SUM-159-PT), the cells were cultured for 48h in charcoal-stripped FBS media (2.5% for MDA-MB-231 or 5% for SUM-159-PT). Cells were treated for 72h and 96h with varying concentrations of paclitaxel (0-100 nM) in the presence of Vehicle/Vehicle, 100 nM Dex/Vehicle, Vehicle/1 µM C297, or 100 nM Dex/1 µM C297. After compound treatment, cells were fixed in 10% trichloroacetic acid (TCA) at 4° C. overnight. The sulforhodamine B (SRB) assay was performed as reported (109). Absorbance at $\lambda=510$ nm was measured, and relative percentage dead/alive cells was calculated based on minimal and maximal optical densities measured per plate. The experiment was performed in three biological replicates per cell line. P-values comparing the means of cell death percentages were obtained using the two-sample Student's t-test (Graphpad).

Murine TNBC Xenograft

MDA-MB-231 tumors were established in the right pectoral mammary gland of n=23 five- or six-week old female SCID mice (Taconic). Tumor volume was measured by caliper and then calculated using the elliptical volume equation (43). When tumors reached a volume of 100-300 mm³, the mice were treated for five days with either 20 mg/kg/day C297 or vehicle one hour prior to 10 mg/kg/day paclitaxel or vehicle. Tumor volume was measured by caliper until reaching a volume of approximately 2000 mm³ or 40 days post-treatment initiation. Tumor data were analyzed using the repeated measures ANOVA using SigmaPlot 11.2 (Systat Software), and p-values between treatment groups over time were obtained using the Holm-Sidak post-hoc test.

Gene Expression Microarray and Analysis

MDA-MB-231 cells were grown to 80% confluence in 15-cm dishes in DMEM with 10% FBS. After culturing cells for 48h in DMEM with 2.5% charcoal-stripped FBS, $2\times10^7$ cells (per condition) were treated with either Vehicle, 100 nM Dex +/-100 nM C297 or 100 nM Mif for 4, 8, and 12h. Following compound exposure, cells were washed in PBS, and lysed in RNA lysis buffer (Qiagen) overnight at -80° C. RNA extraction, with accompanying DNase treatment, was performed using the RNeasy kit (Qiagen) following the manufacturer's protocol. A small sample of each condition was reverse transcribed to perform Q-RT-PCR as a quality control to test GR-induction of SGK1 by Dex over vehicle, and inhibition of that induction by Mif. Duplicate microarray experiments (n=2) for Vehicle, Dex, and Dex/Mif conditions were performed along with a single experiment for the Dex/C297 treatment condition. The University of Chicago Genomics Core facility carried out the reverse transcription on the samples, followed by microarray using the Affymetrix Human U133 Plus 2.0 platform. Expression data were normalized using RMA, and analyzed in R using Bioconductor (110) to determine genes that were up- or downregulated by ≥1.3-fold change. A principal components analysis (PCA) was performed using the prcomp function in R (Q-mode PCA using singular value decomposition). Genes became candidates for further analysis when their expression was altered significantly by Dex, and inhibited commonly by Mif and CORT108297 (within the same time point as Dex) by at least 25%, in at least one of two biological replicates. Heatmaps of the n=3,066 Dex-altered and Mif/C297-antagonized genes were generated using GENE-E (Broad Institute). Dex-regulated genes were overlapped with a list of n=5,170 differentially-expressed tumor-derived genes (in the same direction) from GR-high versus GR-low BCs (52). Ingenuity Pathway Analysis (Qiagen) of the n=462 patient-relevant and antagonist-inhibited genes was performed to obtain Activation Z-scores of the most significant Diseases and Biofunctions (cell functions).

GR ChIP-Sequencing and Analysis

MDA-MB-231 cells were grown to 80% confluence in 15-cm dishes in DMEM with 10% FBS, followed by 48h in DMEM supplemented with 2.5% charcoal-stripped FBS. Cells ($n=4\times10^7$ per treatment condition) were treated with Vehicle, or 100 nM Dex +/-100 nM C297 or 100 nM Mif for 60 minutes. Cells were cross-linked with 1% formaldehyde, quenched with glycine (final concentration of 1.25 mM), and harvested. After cell lysis with ChIP lysis buffer (Magna ChIP A Chromatin Immunoprecipitation Kit, EMD Millipore), cells were sonicated to achieve the majority of DNA fragments between 200-400 bp. Input samples were preserved at -80° C. GR was chromatin immunoprecipitated using 3 µg of ChIP-grade XP (D8H2) rabbit anti-GR antibody (Cell Signaling); 3 µg of rabbit IgG (Cell Signaling) was used for IgG control sample. Following manufacturer's protocol, chromatin was eluted from GR ChIP and input samples. Library build and sequencing was performed at the University of Oregon Genomics Core facility using the NextSeq 500 sequencer. Quality control on sequences and adapter sequencing trimming was performed using Kapa Biosystems Illumina Library Quantification Kit. ChIP-seq analysis was carried out using the Galaxy platform (usegalaxy.org (111)). Briefly, sequences were aligned to the human genome (version hg19) using Bowtie, and after PCR duplicates were removed and reads were filtered, peaks were called using the MACS2 (p-value=0.005 and bw=250). GR peaks for each treatment were normalized to its own input control sample. Peaks for Dex, Dex/Mif, and Dex/C297 were then normalized to Veh/Veh using deepTools2 (deeptools.ie-freiburg.mpg.de (112)). Heatmaps of lost and conserved GR peaks, relative to the Dex GR peak location were generated using Seqplots(113). Motif analysis of GR binding regions at transcription factor response elements was performed using CentriMO (114). ChIPseeker (115) was used to annotate peaks to nearest transcriptional start sites (TSSs) of genes, as well as to analyze GR peak enrichment at genomic features both genome-wide and within 100 kb of a TSS. Selected GR peak locations in hg19 and GR peak maps were also individually analyzed using Integrative Genomics Viewer, IGV (Broad Institute (116)).

Quantitative Real-Time PCR

MDA-MB-231 cells were grown to 80% confluence in 6-cm dishes in DMEM (10% FBS, 1% penicillin/streptomycin), followed by a 72h serum starvation period in charcoal-stripped DMEM (2.5% charcoal-stripped FBS, 1% penicillin/streptomycin). SUM-159PT cells were grown to 80% confluence in 6-cm dishes in Ham's F12 (5% FBS, 1 µg/ml hydrocortisone, 5 µg/ml insulin, 1% penicillin/streptomycin), followed by a 72h serum starvation period in charcoal-stripped Ham's F12 (5% charcoal-stripped FBS, 1% penicillin/streptomycin). Cells were treated with the following for 4, 8, and 12-hr: Vehicle (EtOH, 0.2% final volume), Veh/100 nM Dex, Dex/Mif (100 nM each), or Dex/C297 (100 nM each). Following treatment, cells were washed once with PBS and lysed in 500 μl of RLT buffer (Qiagen) supplemented with 1% 2-mercaptoethanol overnight at −80° C. Three biological replicates were performed for each compound treatment per cell line. Total RNA extraction, with accompanying DNase treatment, was performed using the Qiagen RNeasy kit (Qiagen) following manufacturer's protocol. cDNA was then reverse-transcribed from 1 μg of total RNA with Quanta reverse transcription reagents (Quanta Biosciences) using the GeneAmp PCR 9700 (Applied BioSystems) per manufacturer's instruction. PerfeCTa SYBR Green FastMix (Quanta Biosciences) was used to perform quantitative real-time PCR with the BioRad PCR System MyIQ (BioRad Life Sciences). Following primers were used: RPLP0 (housekeeping gene), 5'-GGAGAAACTGCTGCCTCATATC-3' (SEQ ID NO: 2) (forward) and 5'-CAGCAGCTGGCACCTTATT-3' (SEQ ID NO: 3) (reverse); SGK1, 5'-GGCACCACCAGTC-CACA-3' (SEQ ID NO: 4) (forward) and 5'-GGCACGCCG-GAGTATCT-3' (SEQ ID NO: 5) (reverse); DUSP1/MKP1, 5'-CCTGACAGCGCGGAATCT-3' (SEQ ID NO: 6) (forward) and 5'-GATTTCCACCGGGCCAC-3' (SEQ ID NO: 7) (reverse); G/LZ, 5'-ACAGGCCATGGATCTGGTGA-3' (SEQ ID NO: 8) (forward) and 5'-CAGCTCTCG-GATCTGCTCCTT-3' (SEQ ID NO: 9) (reverse); MCL1, 5'-TGGCTAAACACTTGAAGACC-3' (SEQ ID NO: 10) (forward) and 5'-GGAAGAACT CCACAAACCC-3' (SEQ ID NO: 11) (reverse); NNMT, 5'-GAGCAGAAGTTCTCCAGCCT-3' (SEQ ID NO: 12) (forward) and 5'-ACCATTCGATTGTGTAGCCA-3' (SEQ ID NO: 13) (reverse). Genomic contamination control primers for GR/E3 were also used to assure RNA purity. Fold change was calculated by using the ΔΔCt approach (117); Ct values were first normalized to the housekeeping gene RPLP0 and fold-changes were relative to vehicle controls. Propagated error (standard deviation) in fold change was calculated (117) and p-values were generated with the two-sample Student's t-test with Welch's correction for unequal variances (GraphPad).

siRNA Knockdown

MDA-MB-231 cells were cultured to 80% confluence in 10-cm dishes. siRNA knockdown was carried out using the Smartpool (Dharmakon) of four siRNAs against either MCL1 or NNMT. Scrambled control pool was used as well (Dharmakon). siRNAs were introduced into cells using the RNAimax forward transfection protocol (Invitrogen). Knockdown efficiency was analyzed by Q-RT-PCR (see Methods above) normalizing NNMT siRNA pool and MCL1 siRNA pool to the Control siRNA pool. After efficient knockdown (48h), cells were treated with Veh/Veh, a range of concentrations (10-100 nM) of paclitaxel +/−100 nM Dex for 48h. Cell death was assessed using the sulforhodamine B assay (see Methods above). Percentage of cell death was averaged over three experiments and significance of mean cell death was analyzed using the Student's t-test (GraphPad).

Retrospective Analysis of Early-Stage ER-Negative BC Tumor NR3C1 Gene Expression Association with RFS in TNBC Subtypes A gene expression database of TNBC gene arrays was established previously (59, 60). TNBC molecular subtypes were defined by Pietenpol et al (4). TNBC patients were classified according to NR3C1 gene expression (Affymetrix probeID 216321_s_at) being in the top quartile of expression versus all others. The cutoff values were determined based on all patients in a given group. RFS was estimated using the method of Kaplan-Meier and compared between patients in the top quartile of NR3C1 expression vs. all others using the logrank test. Hazard ratios (HRs) were estimated using Cox proportional hazards regression models.

Retrospective Analysis of Early-Stage ER-Negative BC Tumor Gene Expression Association with RFS in Discovery and Validation Cohorts A subset of n=68 ER-negative BC patients who received adjuvant chemotherapy from our previously reported study (52) was used as the Discovery cohort (FIG. 14). The independent Validation set of n=199 ER-negative BC patients who received adjuvant chemotherapy was also obtained (60) (FIG. 14). Expression data were processed and normalized as described in (52) and (118), respectively. The GR activity signature (GRsig) was defined as the subset of genes with individual RFS-associated p-value threshold of $p \leq 1 \times 10^{-5}$ and a $HR \geq 1.5$ for Dex-induced genes or $HR \leq 0.67$ (1/1.5) for Dex-repressed genes. To test the GRSig in both the Discovery and Validation cohorts, normalized expression levels of the 74 genes were added (Dex-upregulated genes) or subtracted (Dex-repressed genes) to obtain GRsig expressions. Patients were classified as having high GRsig expression if their GRsig expression was above the median GRsig expression among all n=354 ER-negative patients. RFS in each group was estimated using the method of Kaplan-Meier, and was compared using the logrank test. Hazard ratios (HRs) were estimated using Cox regression models.

Example 2

High GR Transcript Associates with Poor RFS Across TNBC Subtypes

Unique gene expression signatures, discovered and refined by Pietenpol and co-workers (3, 4), have allowed TNBCs to be classified into basal-like 1, basal-like 2, mesenchymal, and LAR subtypes, collectively named the TNBCtype-4. In light of our previous finding that high GR NR3C1 tumor gene expression from early-stage ER-negative BC patients associated with poor RFS (52), we asked whether high tumor GR NR3C1 transcript expression retained an association with poor outcome in these defined TNBC subtypes. A retrospective meta-analysis of gene expression was performed using n=624 TNBC tumors(59, 60). Kaplan-Meier estimates of RFS in TNBC patients in the highest quartile of tumor GR NR3C1 mRNA expression (versus all others) are shown in FIG. 1 for each of TNBC subtypes: basal-like-1 (n=171), basal-like-2 (n=76), mesenchymal (n=175), and LAR (n=202). We found that high tumor GR NR3C1 mRNA expression was significantly associated with poor RFS in the basal-like 1 (hazard ratio [HR]=1.87, p=0.013), mesenchymal (HR=1.65, p=0.040), and LAR (HR=1.68, p=0.015) subtypes. A non-significant trend toward high GR/NR3C1 association with poor RFS in the basal-like 2 was also observed, although the number of patients in this group was small. Together, these data suggest that GR expression levels, and by extrapolation, GR activity, can stratify most ER-negative BC patients.

Example 3

Selective Non-Steroidal GR Modulator C297 is Comparable to Mifepristone in its GR LBD Affinity and Chemosensitization of TNBC Cells We next sought to understand how relatively high GR transcriptional activity might lead to a chemoresistant and more aggressive tumor phenotype. We used the agonist Dex (100 nM) to mimic basally activated GR (by endogenous GCs in patients (61). We first performed an in vitro GR ligand competition assay to choose effective antagonists for this study. Selective non-steroidal GR modulators aryl pyrazole azadecalin C297 (58), pyrimidinedione CORT118335 (C335) (62, 63), as well as the GR/PR steroidal antagonist Mif, all potently displaced fluorescently-labeled Dex (F-Dex) from the GR ligand binding domain (LBD) with low nM affinities (FIGS. 7A and 7B). As expected, we did not observe GC competition using dihydrotestosterone (DHT as a negative control). The published GR modulator Compound A (CpdA), previously shown to displace $H^3$-Dex in cell lysates (64, 65), did not displace F-Dex from the GR LBD in our in competition assay (FIGS. 7A and 7B). This implies that regions outside the GR LBD are required for CpdA action on GR (66). Because C335 has been reported to also bind the mineralocorticoid receptor (62, 63), which may be expressed in TNBC (67), C297 and Mif were selected as the best antagonists available to further characterize GR transcriptional and functional activity.

We previously found that treatment with physiological concentrations of GCs decrease TNBC sensitivity to chemotherapy (41). This suggests that GR activation in high-GR-expressing TNBCs may contribute to chemotherapy resistance in tumor cells where GR is activated by endogenous cortisol. Indeed, we found that GR antagonism by Mif could counteract the effects of GC activation on tumor cell survival and thus increase paclitaxel cytotoxicity both in vitro and in vivo (43). To determine if non-steroidal C297 could likewise increase chemosensitivity in GR-positive TNBC, we first tested C297-altered paclitaxel cytotoxicity in two cell lines, MDA-MB-231 and SUM-159-PT. We observed that GC (Dex, 100 nM) dampened paclitaxel (10 nM) cytotoxicity, while the addition of the GR antagonist C297 (1 μM) caused a modest, but significant, relative increase in paclitaxel cytotoxicity in vitro (FIG. 2A). As was seen previously with Mif in ER-negative cell lines (40, 43), C297 treatment alone did not reduce cell viability in vitro (FIG. 8A). This suggests that C297 antagonism of GR increases cell susceptibility to paclitaxel-induced cytotoxicity rather than direct GR antagonist-induced cytotoxicity.

Next, we studied the in vivo effect of GR activity in paclitaxel-treated GR+TNBC-bearing female SCID mice (n=23). MDA-MB-231 xenograft tumors were established subcutaneously in the mammary fat pad of 6-week old female mice. When tumors reached a volume of 100-300 mm³, the mice were randomly assigned to treatment groups such that each group had an approximately equal average tumor volume. The mice were treated daily for five days with intraperitoneally with C297 (or vehicle), one hour prior to paclitaxel. The one-hour pre-treatment of the GR modulator was intended to compete with endogenous GC (murine corticosterone and cortisol (68)) bound to the tumor cell GR LBD. The 5 sequential dosing was selected to mimic an intensive adjuvant chemotherapy schedule often used in early-stage TNBC. Following cessation of the 5d treatment, time to tumor xenograft re-growth was measured as a readout for time to relapse post-treatment (43, 46). Consistent with previous in vivo results with Mif pre-treatment followed by paclitaxel (43), we observed a significantly increased time to post treatment tumor re-growth with C297/paclitaxel compared to treatment with vehicle/paclitaxel (FIG. 2B). Similar to the observations in vitro, C297 monotherapy did not cause a significant delay in tumor re-growth (FIG. 8B), suggesting that GR antagonism alone is neither cytotoxic nor sufficient to delay tumor progression in a TNBC model. These data are consistent with C297 increasing chemotherapy sensitivity by reversing GR-mediated expression of genes encoding anti-apoptotic proteins. These data further suggest that as with the non-selective GR antagonist Mif, selective GR antagonism can inhibit GR-mediated chemotherapy resistance both in vitro and in vivo, thereby delaying the time of tumor re-growth.

Example 4

GR Antagonism Identifies GR-Regulated Transcriptional Pathways Related to Chemoresistance and Aggressiveness Having established that both C297 and Mif displace GC at the GR LBD, increase chemotherapy sensitivity in the context of GC-activated GR, and also delay tumor growth in comparison to chemotherapy treatment alone, we next sought to define which GR-regulated genes were relevant to tumor cell survival. We first used genome-wide gene expression profiling to identify GC-altered gene expression. We then used signatures of antagonist-altered GC-regulated gene expression to determine the subset of those GR-regulated genes commonly antagonized by treatment with either Mif or C297. Using a GR-induced or repressed transcript expression cut-off of at least +/−1.3 fold-change over vehicle treatment, GC treatment (Dex 100 nM) resulted in n=2,719 upregulated genes and n=3,202 downregulated genes at 4, 8 and 12 hours combined (FIG. 3A). Markedly fewer genes were altered (in comparison to vehicle) upon co-treatment with either GR modulator (n=1,548 upregulated/1,416 downregulated for Dex/Mif, and n=1,904 upregulated/2,324 downregulated for Dex/C297, FIG. 3A). Interestingly, about half of the GC-mediated genes (upregulated: 50%, n=1363; or downregulated: 41%, n=1321) were unique to Dex treatment (FIG. 9A). A principal components analysis of the differentially altered gene signatures for the three treatments revealed that the Dex/Mif signatures were more closely correlated with the Dex/C297 signatures than to the Dex signatures at their respective timepoints (FIG. 9B). These data imply that Dex/Mif and Dex/C297 antagonize a GC-induced GR transcript profile and modulate a common subset of genes.

We next sought to identify the subset of GR-regulated genes whose activation or repression was commonly antagonized by both C297 and Mif treatment. We found n=3,066 genes for which both GR modulators antagonized GR induction or repression by at least 25% (FIG. 3B, FIG. 9C). Interestingly, 87% of the GR-regulated genes that C297 antagonized were also regulated in the same direction by Mif, whereas about two-thirds (68%) of the Mif-antagonized GR-regulated genes were shared with C297. These data suggest that Mif is less selective for GR than C297 and/or that Mif is the more potent GR modulator at 100 nM. Because both Mif and C297 displaced GC at the GR LBD and enhanced GR+TNBC chemosensitivity in vivo, these n=3,066 commonly GR-regulated genes were further considered as candidate GR activity genes relevant to poor prognosis in ER-negative BC.

We next used a restrospective meta-anaylsis dataset of primary early-stage ER-negative tumor gene expression signatures to identify the subset of the commonly antagonized GR-regulated genes (n=3,066 from FIG. 3B) that might contribute to a higher risk of TNBC relapse. We previously identified n=5,170 tumor-derived genes that were differentially expressed in GR-high versus GR-low tumors from n=354 ER-negative BCs (52). We found n=462 genes were shared between the n=3,066 genes that were commonly antagonized by C297/Mif and the n=5,170 tumor-derived genes from GR-high versus GR-low primary BCs (FIG. 3C). These n=462 genes were expressed in the same direction, i.e., an Dex-upregulated gene was overexpressed in the GR-high versus GR-low gene list. To better characterize the GR gene expression networks, we performed pathway analysis on the n=462 antagonist-modulated/tumor-relevant genes from FIG. 3C. Exploring known pathway functions in cancer cells using Ingenuity Pathway Analysis (IPA), we found that these GR-regulated genes were significantly associated with cancer cell survival (inhibition of apoptosis), tumor cell invasion, and epithelial-to-mesenchymal transition pathways. Shown in FIG. 13, the combination of a positive or negative pathway activation Z-score in the GC (Dex) treatment, and a relative dampening of Z-score magnitude upon the addition of either Mif or C297, confirmed antagonism of these GR activated and inactivated signaling pathways. This finding suggests that antagonized GR network genes contribute to tumor relapse and chemotherapy resistance through recognized cell viability pathways. Moreover, these GR-regulated gene expression networks are potentially reversible using GR antagonists to improve chemotherapy efficacy.

Example 5

GR Antagonism Reduces GR Association at Promoter Regions

The subset of putative direct GR target genes among the n=462 GR-altered/patient-relevant genes from FIG. 3C was next identified using GC-activated GR chromatin association data from MDA-MB-231 cells. To achieve this, we performed GR ChIP-sequencing in cells treated with vehicle, GC (Dex), Dex/Mif, or Dex/C297. After normalizing GR peaks from treated conditions with vehicle, we found n=8,448 Dex genome-wide GR peaks, n=6,361 Dex/Mif GR peaks, and n=11,198 Dex/C297 GR peaks (FIG. 4A, top). When examining Dex genome-wide GR peaks, we observed that only 7% (n=652) Dex GR peaks many were not conserved in the Dex/Mif and Dex/C297 treatments (FIG. 10A). Motif analysis of these peaks was performed and transcription factor (TF) response elements (REs) were identified. Shown in FIG. 4B, the most significant ligand-bound GR binding regions (GBRs) were found at GR response elements (GREs), regardless of treatment condition. Furthermore, we found some common GR enrichment at FOXO and POU REs in all three treatments, however these REs were much less significant with both Dex and Dex/C297 treatments compared to the Dex/Mif treatment. AP1 and ELK REs were only shared between Dex and Dex/C297 treatments, and were lost with Dex/Mif treatment. These data suggest that although Mif and C297 have many shared effects on GR-mediated gene expression, they also appear to alter GR chromatin association in many distinctive genomic locations.

While we observed genome-wide relative enrichment of activated GR (upon treatment with GC) within promoter regions, there was a decrease in relative GR promoter enrichment (+/−3kb) upon co-treatment with either Mif or C297, suggesting that the antagonists preferentially decrease GR association near the TSSs, (FIG. 10B), while they relatively increase distal GR chromatin association at putative enhancer regions. We next annotated GR peaks to the nearest transcriptional start site (TSS) using a maximum allowable distance of 100 kB from peak to TSS (FIG. 4A, bottom). When we limited the GR peak analysis to peaks within +/−100 kb of the TSS, GC treatment induced a robust GR enrichment within 1kb of the TSS, while GR association in this region was significantly decreased following the addition either GR antagonist (FIG. 4C). This finding suggests that GR antagonists may function, at least in part, through preferentially displacing GR from proximal promoter regions. Interestingly, there is not an overall loss of GR chromatin association with C297 treatment, but rather a redirection to new GBRs further away from the TTS, as demonstrated by the increase in genome-wide peak numbers shown in FIG. 4A.

To identify putative direct GR target genes that are antagonized in expression by either Mif or C297, we next determined the subset of n=462 tumor-relevant genes (from FIG. 3C) with Dex-GR peaks within +/−100 kb of their TSS (FIG. 4A). We found n=232 putative direct GR target genes with significant Dex GBRs within 100 kb, suggesting either promoter or enhancer interaction by GC-activated GR. Indeed, several previously characterized GR target genes were identified within this list, such as SGK1(69), DUSP1/MKP1 (70), and GILZ/TSC22D3(71). Additionally, the n=232 putative direct GR target genes also include those with known involvement in cancer cell chemoresistance and evasion of apoptosis (MCL1(72), MUC1(73), GADD45B (74), DNAJC15 MCJ(75)), epigenetic modification and metabolism (NMMT(76), SLC2A3/GLUT3(77), ACSL1 (78), SP110(79)), metastasis and invasion (CYR61(80), TGFB2(81), EIF4E(82), F2R/PAR1 (83)), angiogenesis (KDR(84), EIF4E(85), CALD1 (86)), and inflammation (IL15(87), IL1R1 (88, 89), IL7R(90), IRAK3(91)). We selected five of these GR target genes (SGK1, DUSP1/MKP1, TSC22D3, MCL1, NNMT) and validated antagonist-modulated gene expression by Q-RT-PCR in MDA-MB-231 or SUM-159-PT cells (FIGS. 11A and 11B). Furthermore, individual transient knockdown of two GR target genes of recent interest in TNBC, MCL1(72) and NNMT(76, 92), in MDA-MB-231 cells increased paclitaxel cytotoxicity (FIG. 11C, FIG. 11D). Finally, an examination of GR chromatin association within 100 kb +/− the gene TSS for these n=232 putative direct GR target genes revealed that the majority of Dex-GBRs were lost upon Mif or C297 treatment (Appendix). These n=232 genes make up gene expression pathways for which GR appears to be a common TF and for which GR antagonists reverse GC-mediated gene expression.

Example 6

A GR Activity Signature (Grsig) has a Stronger Association with Rfs than GR Expression Alone We next identified a GC-mediated gene set reflective of tumor-relevant GR activity and clinical outcome. To do this, we analyzed the association between RFS and tumor expression using the n=462 putative indirect and direct GR target genes from FIG. 3C. Using a Discovery cohort of n=68 ER-negative BC patients from two studies who received adjuvant chemotherapy (a dataset we previously reported (52), FIG. 13), we determined individual gene association with RFS using a Cox proportional hazards regression model with continuous expression as a predictor. Next, we formed a putative GR activity signature (GRsig) by selecting the most significantly RFS-associated genes using a stringent cut-off criteria including: RFS-associated $p<1\times10^{-5}$, and a $HR\geq1.5$ for GC-induced genes or $HR\leq0.67$ (1/1.5) for Dex-repressed genes (FIG. 5). From this, we obtained an n=74 gene GRsig (FIG. 14). Of the genes in the GRsig, about 42% (n=31, FIG. 6A) are putative GR direct target genes. For these direct GR target genes within the GRsig, nearly all of the Dex GBRs (within +/−100 kb of each GRsig gene TSS) was lost upon addition of Mif or C297 (FIG. 6A bottom, Appendix).

We then compared RFS between ER-negative patients with high (above-median of all ER − negative BC patients) and low (below-median of all ER-negative BC patients) tumor GRsig expression in the same Discovery Cohort (n=68) from which the signature was derived. As expected, patients with high tumor GRsig expression had worse RFS (HR=8.1; $p=2.3\times10^{-10}$, FIG. 6C). To validate this signature, we examined the GRsig in an external (non-overlapping) Validation Cohort of n=199 ER-negative BC early-stage and chemotherapy-treated patients ((59, 60), FIG. 14). The Cox regression model revealed that patients with high tumor GRsig expression had significantly shorter time to relapse compared to those with low GRsig expression (HR=1.9; p=0.012, FIG. 6D). Interestingly, the GRsig associated more significantly with poor RFS in the Validation Cohort compared to NR3C1 alone (supplementary FIG. 12). Taken together, these data imply that a GR signature derived from antagonizable transcriptional targets is a better indicator of GR activity than GR expression alone. Secondly, these data suggest that the GRsig could serve to stratify high-risk patients for the addition of GR antagonist treatment to their chemotherapy regimen.

REFERENCES

The following references, to the extent that they provide exemplary procedural or other details supplementary to those set forth herein, are specifically incorporated herein by reference.

1. G. Bianchini, J. M. Balko, I. A. Mayer, M. E. Sanders, L. Gianni, Triple-negative breast cancer: challenges and opportunities of a heterogeneous disease. *Nat Rev Clin Oncol* 13, 674-690 (2016).
2. B. Weigelt, J. L. Peterse, L. J. van't Veer, Breast cancer metastasis: markers and models. *Nat Rev Cancer* 5, 591-602 (2005).
3. B. D. Lehmann, J. A. Bauer, X. Chen, M. E. Sanders, A. B. Chakravarthy, Y. Shyr, J. A. Pietenpol,
Identification of human triple-negative breast cancer subtypes and preclinical models for selection of targeted therapies. *J Clin Invest* 121, 2750-2767 (2011).
4. B. D. Lehmann, B. Jovanovic, X. Chen, M. V. Estrada, K. N. Johnson, Y. Shyr, H. L. Moses, M. E. Sanders, J. A. Pietenpol, Refinement of Triple-Negative Breast Cancer Molecular Subtypes: Implications for Neoadjuvant Chemotherapy Selection. *PLoS One* 11, e0157368 (2016).
5. A. M. Gonzalez-Angulo, K. Stemke-Hale, S. L. Palla, M. Carey, R. Agarwal, F. Meric-Berstam, T. A. Traina, C. Hudis, G. N. Hortobagyi, W. L. Gerald, G. B. Mills, B. T. Hennessy, Androgen receptor levels and association with PIK3CA mutations and prognosis in breast cancer. *Clin Cancer Res* 15, 2472-2478 (2009).
6. J. A. Bauer, F. Ye, C. B. Marshall, B. D. Lehmann, C. S. Pendleton, Y. Shyr, C. L. Arteaga, J. A. Pietenpol, RNA interference (RNAi) screening approach identifies agents that enhance paclitaxel activity in breast cancer cells. *Breast Cancer Res* 12, R41 (2010).
7. N. Cancer Genome Atlas, Comprehensive molecular portraits of human breast tumours. *Nature* 490, 61-70 (2012).
8. A. Gucalp, S. Tolaney, S. J. Isakoff, J. N. Ingle, M. C. Liu, L. A. Carey, K. Blackwell, H. Rugo, L. Nabell, A. Forero, V. Stearns, A. S. Doane, M. Danso, M. E. Moynahan, L. F. Momen, J. M. Gonzalez, A. Akhtar, D. D. Giri, S. Patil, K. N. Feigin, C. A. Hudis, T. A. Traina, C. Translational Breast Cancer Research, Phase II trial of bicalutamide in patients with androgen receptor-positive, estrogen receptor-negative metastatic Breast Cancer. *Clin Cancer Res* 19, 5505-5512 (2013).
9. D. W. Craig, J. A. O'Shaughnessy, J. A. Kiefer, J. Aldrich, S. Sinari, T. M. Moses, S. Wong, J. Dinh, A. Christoforides, J. L. Blum, C. L. Aitelli, C. R. Osborne, T. Izatt, A. Kurdoglu, A. Baker, J. Koeman, C. Barbacioru, O. Sakarya, F. M. De La Vega, A. Siddiqui, L. Hoang, P. R. Billings, B. Salhia, A. W. Tolcher, J. M. Trent, S. Mousses, D. Von Hoff, J. D. Carpten, Genome and transcriptome sequencing in prospective metastatic triple-negative breast cancer uncovers therapeutic vulnerabilities. *Mol Cancer Ther* 12, 104-116 (2013).
10. Y. C. Hsu, H. Y. Chen, S. Yuan, S. L. Yu, C. H. Lin, G. Wu, P. C. Yang, K. C. Li, Genome-wide analysis of three-way interplay among gene expression, cancer cell invasion and anti-cancer compound sensitivity. *BMC Med* 11, 106 (2013).
11. J. M. Balko, J. M. Giltnane, K. Wang, L. J. Schwarz, C. D. Young, R. S. Cook, P. Owens, M. E. Sanders, M. G. Kuba, V. Sanchez, R. Kurupi, P. D. Moore, J. A. Pinto, F. D. Doimi, H. Gomez, D. Horiuchi, A. Goga, B. D. Lehmann, J. A. Bauer, J. A. Pietenpol, J. S. Ross, G. A. Palmer, R. Yelensky, M. Cronin, V. A. Miller, P. J. Stephens, C. L. Arteaga, Molecular profiling of the residual disease of triple-negative breast cancers after neoadjuvant chemotherapy identifies actionable therapeutic targets. *Cancer Discov* 4, 232-245 (2014).
12. Y. M. Kanaan, B. P. Sampey, D. Beyene, A. K. Esnakula, T. J. Naab, L. J. Ricks-Santi, S. Dasi, A. Day, K. W. Blackman, W. Frederick, R. L. Copeland, Sr., E. Gabrielson, R. L. Dewitty, Jr., Metabolic profile of triple-negative breast cancer in African-American women reveals potential biomarkers of aggressive disease. *Cancer Genomics Proteomics* 11, 279-294 (2014).
13. R. T. Lawrence, E. M. Perez, D. Hernandez, C. P. Miller, K. M. Haas, H. Y. Irie, S. I. Lee, C. A. Blau, J. Villen, The proteomic landscape of triple-negative breast cancer. *Cell Rep* 11, 630-644 (2015).
14. V. N. Barton, N. C. D'Amato, M. A. Gordon, H. T. Lind, N. S. Spoelstra, B. L. Babbs, R. E. Heinz, A. Elias, P. Jedlicka, B. M. Jacobsen, J. K. Richer, Multiple molecular subtypes of triple-negative breast cancer critically rely on androgen receptor and respond to enzalutamide in vivo. *Mol Cancer Ther* 14, 769-778 (2015).
15. J. M. Balko, L. J. Schwarz, N. Luo, M. V. Estrada, J. M. Giltnane, D. Davila-Gonzalez, K. Wang, V. Sanchez, P. T. Dean, S. E. Combs, D. Hicks, J. A. Pinto, M. D. Landis, F. D. Doimi, R. Yelensky, V. A. Miller, P. J. Stephens, D. L. Rimm, H. Gomez, J. C. Chang, M. E. Sanders, R. S. Cook, C. L. Arteaga,
Triple-negative breast cancers with amplification of JAK2 at the 9p24 locus demonstrate JAK2-specific dependence. *Sci TranslMed* 8, 334ra353 (2016).
16. N. E. Bhola, V. M. Jansen, J. P. Koch, H. Li, L. Formisano, J. A. Williams, J. R. Grandis, C. L. Arteaga, Treatment of Triple-Negative Breast Cancer with TORC1/2 Inhibitors Sustains a Drug-Resistant and Notch-Dependent Cancer Stem Cell Population. *Cancer Res* 76, 440-452 (2016).
17. C. Stirzaker, E. Zotenko, S. J. Clark, Genome-wide DNA methylation profiling in triple-negative breast cancer reveals epigenetic signatures with important clinical value. *Mol Cell Oncol* 3, e1038424 (2016).
18. V. N. Barton, J. L. Christenson, M. A. Gordon, L. I. Greene, T. J. Rogers, K. Butterfield, B. Babbs, N. S. Spoelstra, N. C. D'Amato, A. Elias, J. K. Richer, Androgen Receptor Supports an Anchorage-Independent, Cancer Stem Cell-like Population in Triple-Negative Breast Cancer. *Cancer Res* 77, 3455-3466 (2017).
19. S. Shu, C. Y. Lin, H. H. He, R. M. Witwicki, D. P. Tabassum, J. M. Roberts, M. Janiszewska, S. J. Huh, Y. Liang, J. Ryan, E. Doherty, H. Mohammed, H. Guo, D. G. Stover, M. B. Ekram, J. Brown, C. D'Santos, I. E. Krop, D. Dillon, M. McKeown, C. Ott, J. Qi, M. Ni, P. K. Rao, M. Duarte, S. Y. Wu, C. M. Chiang, L. Anders, R. A. Young, E. Winer, A. Letai, W. T. Barry, J. S. Carroll, H. Long, M. Brown, X. S. Liu, C. A. Meyer, J. E. Bradner, K. Polyak, Response and resistance to BET bromodomain inhibitors in triple-negative breast cancer. *Nature* 529, 413-417 (2016).
20. M. G. Cordingley, A. T. Riegel, G. L. Hager, Steroid-dependent interaction of transcription factors with the inducible promoter of mouse mammary tumor virus in vivo. Cell 48, 261-270 (1987).
21. C. J. Fryer, H. K. Kinyamu, I. Rogatsky, M. J. Garabedian, T. K. Archer, Selective activation of the glucocorticoid receptor by steroid antagonists in human breast cancer and osteosarcoma cells. *J Biol Chem* 275, 17771-17777 (2000).
22. H. K. Kinyamu, C. J. Fryer, K. B. Horwitz, T. K. Archer, The mouse mammary tumor virus promoter adopts distinct chromatin structures in human breast cancer cells with and without glucocorticoid receptor. *J Biol Chem* 275, 20061-20068 (2000).
23. E. K. Keeton, T. M. Fletcher, C. T. Baumann, G. L. Hager, C. L. Smith, Glucocorticoid receptor domain requirements for chromatin remodeling and transcriptional activation of the mouse mammary tumor virus promoter in different nucleoprotein contexts. *J Biol Chem* 277, 28247-28255 (2002).
24. S. Aoyagi, T. K. Archer, Differential glucocorticoid receptor-mediated transcription mechanisms. *J Biol Chem* 286, 4610-4619 (2011).
25. T. B. Miranda, S. A. Morris, G. L. Hager, Complex genomic interactions in the dynamic regulation of transcription by the glucocorticoid receptor. *Mol Cell Endocrinol* 380, 16-24 (2013).
26. S. Muratcioglu, D. M. Presman, J. R. Pooley, L. Grontved, G. L. Hager, R. Nussinov, O. Keskin, A. Gursoy, Structural Modeling of GR Interactions with the SWI/SNF Chromatin Remodeling Complex and C/EBP. *Biophys J* 109, 1227-1239 (2015).
27. R. H. Oakley, J. A. Cidlowski, The biology of the glucocorticoid receptor: new signaling mechanisms in health and disease. *J Allergy Clin Immunol* 132, 1033-1044 (2013).
28. S. Schmidt, J. Rainer, C. Ploner, E. Presul, S. Riml, R. Kofler, Glucocorticoid-induced apoptosis and glucocorticoid resistance: molecular mechanisms and clinical relevance. *CellDeath Differ* 11 Suppl 1, S45-55 (2004).
29. G. Schlossmacher, A. Stevens, A. White, Glucocorticoid receptor-mediated apoptosis: mechanisms of resistance in cancer cells. *J Endocrinol* 211, 17-25 (2011).
30. H. Ishiguro, T. Kawahara, Y. Zheng, E. Kashiwagi, Y. Li, H. Miyamoto, Differential regulation of bladder cancer growth by various glucocorticoids: corticosterone and prednisone inhibit cell invasion without promoting cell proliferation or reducing cisplatin cytotoxicity. *Cancer Chemother Pharmacol* 74, 249-255 (2014).
31. J. E. Wolff, J. Denecke, H. Jurgens, Dexamethasone induces partial resistance to cisplatinum in C6 glioma cells. *Anticancer Res* 16, 805-809 (1996).
32. I. Herr, E. Ucur, K. Herzer, S. Okouoyo, R. Ridder, P. H. Krammer, M. von Knebel Doeberitz, K. M. Debatin, Glucocorticoid cotreatment induces apoptosis resistance toward cancer therapy in carcinomas. *Cancer Res* 63, 3112-3120 (2003).
33. C. Zhang, A. Kolb, P. Buchler, A. C. Cato, J. Mattern, W. Rittgen, L. Edler, K. M. Debatin, M. W. Buchler, H. Friess, I. Herr, Corticosteroid co-treatment induces resistance to chemotherapy in surgical resections, xenografts and established cell lines of pancreatic cancer. *BMC Cancer* 6, 61 (2006).
34. C. Zhang, A. Marme, T. Wenger, P. Gutwein, L. Edler, W. Rittgen, K. M. Debatin, P. Altevogt, J. Mattern, I. Herr, Glucocorticoid-mediated inhibition of chemotherapy in ovarian carcinomas. *Int J Oncol* 28, 551-558 (2006).
35. A. A. Goyeneche, R. W. Caron, C. M. Telleria, Mifepristone inhibits ovarian cancer cell growth in vitro and in vivo. *Clin Cancer Res* 13, 3370-3379 (2007).
36. N. Yang, H. Zhang, H. Si-Ma, Y. Fu, W. Zhao, D. Li, G. Yang, Dexamethasone decreases hepatocellular carcinoma cell sensitivity to cisplatin-induced apoptosis. *Hepatogastroenterology* 58, 1730-1735 (2011).
37. V. K. Arora, E. Schenkein, R. Murali, S. K. Subudhi, J. Wongvipat, M. D. Balbas, N. Shah, L. Cai, E. Efstathiou, C. Logothetis, D. Zheng, C. L. Sawyers, Glucocorticoid receptor confers resistance to antiandrogens by bypassing androgen receptor blockade. *Cell* 155, 1309-1322 (2013).
38. M. Isikbay, K. Otto, S. Kregel, J. Kach, Y. Cai, D. J. Vander Griend, S. D. Conzen, R. Z. Szmulewitz, Glucocorticoid receptor activity contributes to resistance to androgen-targeted therapy in prostate cancer. *Horm Cancer* 5, 72-89 (2014).
39. E. M. Stringer-Reasor, G. M. Baker, M. N. Skor, M. Kocherginsky, E. Lengyel, G. F. Fleming, S. D. Conzen, Glucocorticoid receptor activation inhibits chemotherapy-induced cell death in high-grade serous ovarian carcinoma. *Gynecol Oncol* 138, 656-662 (2015).
40. G. X. Huang, X. Y. Pan, Y. D. Jin, Y. Wang, X. L. Song, C. H. Wang, Y. D. Li, J. Lu, The mechanisms and significance of up-regulation of RhoB expression by hypoxia and glucocorticoid in rat lung and A549 cells. *J CellMolMed* 20, 1276-1286 (2016).
41. J. T. Veneris, K. M. Darcy, P. Mhawech-Fauceglia, C. Tian, E. Lengyel, R. R. Lastra, T. Pejovic, S. D. Conzen, G. F. Fleming, High glucocorticoid receptor expression predicts short progression-free survival in ovarian cancer. *Gynecol Oncol*, (2017).
42. J. Kach, T. M. Long, P. Selman, E. Y. Tonsing-Carter, M. A. Bacalao, R. R. Lastra, L. de Wet, S. Comiskey, M. Gillard, C. VanOpstall, D. C. West, W. C. Chan, D. Vander Griend, S. D. Conzen, R. Z. Szmulewitz, Selective glucocorticoid receptor modulators (SGRMs) delay castrate-resistant prostate cancer growth. *Mol Cancer Ther*, (2017).
43. T. J. Moran, S. Gray, C. A. Mikosz, S. D. Conzen, The glucocorticoid receptor mediates a survival signal in human mammary epithelial cells. *Cancer Res* 60, 867-872 (2000).

44. W. Wu, S. Chaudhuri, D. R. Brickley, D. Pang, T. Karrison, S. D. Conzen, Microarray analysis reveals glucocorticoid-regulated survival genes that are associated with inhibition of apoptosis in breast epithelial cells. *Cancer Res* 64, 1757-1764 (2004).

45. D. Pang, M. Kocherginsky, T. Krausz, S. Y. Kim, S. D. Conzen, Dexamethasone decreases xenograft response to Paclitaxel through inhibition of tumor cell apoptosis. Cancer Biol Ther 5, 933-940 (2006).

46. M. N. Skor, E. L. Wonder, M. Kocherginsky, A. Goyal, B. A. Hall, Y. Cai, S. D. Conzen, Glucocorticoid receptor antagonism as a novel therapy for triple-negative breast cancer. *Clin Cancer Res* 19, 6163-6172 (2013).

47. Z. Chen, X. Lan, D. Wu, B. Sunkel, Z. Ye, J. Huang, Z. Liu, S. K. Clinton, V. X. Jin, Q. Wang, Ligand-dependent genomic function of glucocorticoid receptor in triple-negative breast cancer. *Nat Commun* 6, 8323 (2015).

48. P. A. Volden, M. N. Skor, M. B. Johnson, P. Singh, F. N. Patel, M. K. McClintock, M. J. Brady, S. D. Conzen, Mammary Adipose Tissue-Derived Lysophospholipids Promote Estrogen Receptor-Negative Mammary Epithelial Cell Proliferation. *Cancer Prev Res (Phila)* 9, 367-378 (2016).

49. A. S. Agyeman, W. J. Jun, D. A. Proia, C. R. Kim, M. N. Skor, M. Kocherginsky, S. D. Conzen, Hsp90 Inhibition Results in Glucocorticoid Receptor Degradation in Association with Increased Sensitivity to Paclitaxel in Triple-Negative Breast Cancer. *Horm Cancer* 7, 114-126 (2016).

50. Z. Li, J. Dong, T. Zou, C. Du, S. Li, C. Chen, R. Liu, K. Wang, Dexamethasone induces docetaxel and cisplatin resistance partially through up-regulating Kruppel-like factor 5 in triple-negative breast cancer. Oncotarget, (2016).

51. G. Sorrentino, N. Ruggeri, A. Zannini, E. Ingallina, R. Bertolio, C. Marotta, C. Neri, E. Cappuzzello, M. Forcato, A. Rosato, M. Mano, S. Bicciato, G. Del Sal, Glucocorticoid receptor signalling activates YAP in breast cancer. *Nat Commun* 8, 14073 (2017).

52. T. M. Regan Anderson, S. H. Ma, G. V. Raj, J. A. Cidlowski, T. M. Helle, T. P. Knutson, R. I. Krutilina, T. N. Seagroves, C. A. Lange, Breast Tumor Kinase (Brk/PTK6) Is Induced by HIF, Glucocorticoid Receptor, and PELP1-Mediated Stress Signaling in Triple-Negative Breast Cancer. *Cancer Res* 76, 1653-1663 (2016).

53. M. Lippman, G. Bolan, K. Huff, The effects of glucocorticoids and progesterone on hormone-responsive human breast cancer in long-term tissue culture. *Cancer Res* 36, 4602-4609 (1976).

54. Y. Wan, K. K. Coxe, V. G. Thackray, P. R. Housley, S. K. Nordeen, Separable features of the ligand-binding domain determine the differential subcellular localization and ligand-binding specificity of glucocorticoid receptor and progesterone receptor. *Mol Endocrinol* 15, 17-31 (2001).

55. W. Jiang, Z. Zhu, N. Bhatia, R. Agarwal, H. J. Thompson, Mechanisms of energy restriction: effects of corticosterone on cell growth, cell cycle machinery, and apoptosis. *Cancer Res* 62, 5280-5287 (2002).

56. D. Pan, M. Kocherginsky, S. D. Conzen, Activation of the glucocorticoid receptor is associated with poor prognosis in estrogen receptor-negative breast cancer. *Cancer Res* 71, 6360-6370 (2011).

57. D. C. West, D. Pan, E. Y. Tonsing-Carter, K. M. Hernandez, C. F. Pierce, S. C. Styke, K. R. Bowie, T. I. Garcia, M. Kocherginsky, S. D. Conzen, GR and ER Coactivation Alters the Expression of Differentiation Genes and Associates with Improved ER+Breast Cancer Outcome. *Mol Cancer Res* 14, 707-719 (2016).

58. F. Yang, Q. Ma, Z. Liu, W. Li, Y. Tan, C. Jin, W. Ma, Y. Hu, J. Shen, K. A. Ohgi, F. Telese, W. Liu, M. G. Rosenfeld, Glucocorticoid Receptor: MegaTrans Switching Mediates the Repression of an ERalpha-Regulated Transcriptional Program. *Mol Cell* 66, 321-331 e326 (2017).

59. R. Abduljabbar, O. H. Negm, C. F. Lai, D. A. Jerjees, M. Al-Kaabi, M. R. Hamed, P. J. Tighe, L. Buluwela, A. Mukherjee, A. R. Green, S. Ali, E. A. Rakha, I. O. Ellis, Clinical and biological significance of glucocorticoid receptor (GR) expression in breast cancer. *Breast Cancer Res Treat* 150, 335-346 (2015).

60. J. Kroon, M. Puhr, J. T. Buijs, G. van der Horst, D. M. Hemmer, K. A. Marijt, M. S. Hwang, M. Masood, S. Grimm, G. Storm, J. M. Metselaar, O. C. Meijer, Z. Culig, G. van der Pluijm, Glucocorticoid receptor antagonism reverts docetaxel resistance in human prostate cancer. *Endocr Relat Cancer* 23, 35-45 (2016).

61. R. Nanda, E. M. Stringer-Reasor, P. Saha, M. Kocherginsky, J. Gibson, B. Libao, P. C. Hoffman, E. Obeid, D. E. Merkel, G. Khramtsova, M. Skor, T. Krausz, R. N. Cohen, M. J. Ratain, G. F. Fleming, S. D. Conzen, A randomized phase I trial of nanoparticle albumin-bound paclitaxel with or without mifepristone for advanced breast cancer. *Springerplus* 5, 947 (2016).

62. R. D. Clark, N. C. Ray, K. Williams, P. Blaney, S. Ward, P. H. Crackett, C. Hurley, H. J. Dyke, D. E. Clark, P. Lockey, R. Devos, M. Wong, S. S. Porres, C. P. Bright, R. E. Jenkins, J. Belanoff, 1H-Pyrazolo[3,4-g]hexahydro-isoquinolines as selective glucocorticoid receptor antagonists with high functional activity. *BioorgMed Chem Lett* 18, 1312-1317 (2008).

63. B. Gyorffy, A. Lanczky, A. C. Eklund, C. Denkert, J. Budczies, Q. Li, Z. Szallasi, An online survival analysis tool to rapidly assess the effect of 22,277 genes on breast cancer prognosis using microarray data of 1,809 patients. *Breast Cancer Res Treat* 123, 725-731 (2010).

64. Z. Mihaly, M. Kormos, A. Lanczky, M. Dank, J. Budczies, M. A. Szasz, B. Gyorffy, A meta-analysis of gene expression-based biomarkers predicting outcome after tamoxifen treatment in breast cancer. *Breast Cancer Res Treat* 140, 219-232 (2013).

65. J. M. Zeitzer, B. Nouriani, E. Neri, D. Spiegel, Correspondence of plasma and salivary cortisol patterns in women with breast cancer. *Neuroendocrinology* 100, 153-161 (2014).

66. H. J. Hunt, N. C. Ray, G. Hynd, J. Sutton, M. Sajad, E. O'Connor, S. Ahmed, P. Lockey, S. Daly, G. Buckley, R. D. Clark, R. Roe, C. Blasey, J. Belanoff, Discovery of a novel non-steroidal GR antagonist with in vivo efficacy in the olanzapine-induced weight gain model in the rat. *BioorgMed Chem Lett* 22, 7376-7380 (2012).

67. E. T. Nguyen, J. Streicher, S. Berman, J. L. Caldwell, V. Ghisays, C. M. Estrada, A. C. Wulsin, M. B. Solomon, A mixed glucocorticoid/mineralocorticoid receptor modulator dampens endocrine and hippocampal stress responsivity in male rats. *PhysiolBehav*, (2017).

68. K. De Bosscher, W. Vanden Berghe, I. M. Beck, W. Van Molle, N. Hennuyer, J. Hapgood, C. Libert, B. Staels, A. Louw, G. Haegeman, A fully dissociated compound of plant origin for inflammatory gene repression. *Proc Natl Acad Sci USA* 102, 15827-15832 (2005).

69. S. Robertson, F. Allie-Reid, W. Vanden Berghe, K. Visser, A. Binder, D. Africander, M. Vismer, K. De Bosscher, J. Hapgood, G. Haegeman, A. Louw, Abrogation of glucocorticoid receptor dimerization correlates with dissociated glucocorticoid behavior of compound a. *J Biol Chem* 285, 8061-8075 (2010).
70. K. Ronacher, K. Hadley, C. Avenant, E. Stubsrud, S. S. Simons, Jr., A. Louw, J. P. Hapgood, Ligand-selective transactivation and transrepression via the glucocorticoid receptor: role of cofactor interaction. *Mol Cell Endocrinol* 299, 219-231 (2009).
71. I. A. Voutsadakis, Epithelial-Mesenchymal Transition (EMT) and Regulation of EMT Factors by Steroid Nuclear Receptors in Breast Cancer: A Review and in Silico Investigation. *J Clin Med* 5, (2016).
72. S. Gong, Y. L. Miao, G. Z. Jiao, M. J. Sun, H. Li, J. Lin, M. J. Luo, J. H. Tan, Dynamics and correlation of serum cortisol and corticosterone under different physiological or stressful conditions in mice. *PLoS One* 10, e0117503 (2015).
73. C. A. Mikosz, D. R. Brickley, M. S. Sharkey, T. W. Moran, S. D. Conzen, Glucocorticoid receptor-mediated protection from apoptosis is associated with induction of the serine/threonine survival kinase gene, sgk-1. J Biol Chem 276, 16649-16654 (2001).
74. W. Wu, T. Pew, M. Zou, D. Pang, S. D. Conzen, Glucocorticoid receptor-induced MAPK phosphatase-1 (MKP-1) expression inhibits paclitaxel-associated MAPK activation and contributes to breast cancer cell survival. *J Biol Chem* 280, 4117-4124 (2005).
75. E. Ayroldi, G. Migliorati, S. Bruscoli, C. Marchetti, O. Zollo, L. Cannarile, F. D'Adamio, C. Riccardi,
Modulation of T-cell activation by the glucocorticoid-induced leucine zipper factor via inhibition of nuclear factor kappaB. *Blood* 98, 743-753 (2001).
76. A. I. Young, A. M. Law, L. Castillo, S. Chong, H. D. Cullen, M. Koehler, S. Herzog, T. Brummer, E. F. Lee, W. D. Fairlie, M. C. Lucas, D. Herrmann, A. Allam, P. Timpson, D. N. Watkins, E. K. Millar, S. A. O'Toole, D. Gallego-Ortega, C. J. Ormandy, S. R. Oakes, MCL-1 inhibition provides a new way to suppress breast cancer metastasis and increase sensitivity to dasatinib. *Breast Cancer Res* 18, 125 (2016).
77. M. Hiraki, Y. Suzuki, M. Alam, K. Hinohara, M. Hasegawa, C. Jin, S. Kharbanda, D. Kufe, MUC1-C Stabilizes MCL-1 in the Oxidative Stress Response of Triple-Negative Breast Cancer Cells to BCL-2 Inhibitors. *Sci Rep* 6, 26643 (2016).
78. J. Yoo, M. Ghiassi, L. Jirmanova, A. G. Balliet, B. Hoffman, A. J. Fornace, Jr., D. A. Liebermann, E. P. Bottinger, A. B. Roberts, Transforming growth factor-beta-induced apoptosis is mediated by Smad-dependent expression of GADD45b through p38 activation. *J Biol Chem* 278, 43001-43007 (2003).
79. M. J. Fernandez-Cabezudo, I. Faour, K. Jones, D. P. Champagne, M. A. Jaloudi, Y. A. Mohamed, G. Bashir, S. Almarzoogi, A. Albawardi, M. J. Hashim, T. S. Roberts, H. El-Salhat, H. El-Taji, A. Kassis, D. E. O'Sullivan, B. C. Christensen, J. DeGregori, B. K. Al-Ramadi, M. Rincon, Deficiency of mitochondrial modulator MCJ promotes chemoresistance in breast cancer. *JCIInsight* 1, (2016).
80. O. A. Ulanovskaya, A. M. Zuhl, B. F. Cravatt, NNMT promotes epigenetic remodeling in cancer by creating a metabolic methylation sink. *Nat Chem Biol* 9, 300-306 (2013).
81. D. Samanta, D. M. Gilkes, P. Chaturvedi, L. Xiang, G. L. Semenza, Hypoxia-inducible factors are required for chemotherapy resistance of breast cancer stem cells. *Proc NatlAcadSci USA* 111, E5429-5438 (2014).
82. M. Warmoes, J. E. Jaspers, G. Xu, B. K. Sampadi, T. V. Pham, J. C. Knol, S. R. Piersma, E. Boven, J. Jonkers, S. Rottenberg, C. R. Jimenez, Proteomics of genetically engineered mouse mammary tumors identifies fatty acid metabolism members as potential predictive markers for cisplatin resistance. *Mol Cell Proteomics* 12, 1319-1334 (2013).
83. D. B. Bloch, A. Nakajima, T. Gulick, J. D. Chiche, D. Orth, S. M. de La Monte, K. D. Bloch, Sp110 localizes to the PML-Sp100 nuclear body and may function as a nuclear hormone receptor transcriptional coactivator. *Mol Cell Biol* 20, 6138-6146 (2000).
84. M. P. Sanchez-Bailon, A. Calcabrini, V. Mayoral-Varo, A. Molinari, K. U. Wagner, J. P. Losada, S. Ciordia, J. P. Albar, J. Martin-Perez, Cyr61 as mediator of Src signaling in triple negative breast cancer cells. *Oncotarget* 6, 13520-13538 (2015).
85. R. R. Mercer, C. Miyasaka, A. M. Mastro, Metastatic breast cancer cells suppress osteoblast adhesion and differentiation. *Clin Exp Metastasis* 21, 427-435 (2004).
86. J. R. Graff, S. G. Zimmer, Translational control and metastatic progression: enhanced activity of the mRNA cap-binding protein eIF-4E selectively enhances translation of metastasis-related mRNAs. *Clin Exp Metastasis* 20, 265-273 (2003).
87. A. Boire, L. Covic, A. Agarwal, S. Jacques, S. Sherifi, A. Kuliopulos, PAR1 is a matrix metalloprotease-1 receptor that promotes invasion and tumorigenesis of breast cancer cells. *Cell* 120, 303-313 (2005).
88. B. Millauer, S. Wizigmann-Voos, H. Schnurch, R. Martinez, N. P. Moller, W. Risau, A. Ullrich, High affinity VEGF binding and developmental expression suggest Flk-1 as a major regulator of vasculogenesis and angiogenesis. *Cell* 72, 835-846 (1993).
89. P. A. Scott, K. Smith, R. Poulsom, A. De Benedetti, R. Bicknell, A. L. Harris, Differential expression of vascular endothelial growth factor mRNA vs protein isoform expression in human breast cancer and relationship to eIF-4E. *Br J Cancer* 77, 2120-2128 (1998).
90. P. P. Zheng, A. M. Sieuwerts, T. M. Luider, M. van der Weiden, P. A. Sillevis-Smitt, J. M. Kros, Differential expression of splicing variants of the human caldesmon gene (CALD1) in glioma neovascularization versus normal brain microvasculature. *Am JPathol* 164, 2217-2228 (2004).
91. A. Gillgrass, N. Gill, A. Babian, A. A. Ashkar, The absence or overexpression of IL-15 drastically alters breast cancer metastasis via effects on NK cells, CD4 T cells, and macrophages. *J Immunol* 193, 6184-6191 (2014).
92. S. Nozaki, G. W. Sledge, Jr., H. Nakshatri, Cancer cell-derived interleukin 1alpha contributes to autocrine and paracrine induction of pro-metastatic genes in breast cancer. *Biochem Biophys Res Commun* 275, 60-62 (2000).
93. E. Voronov, D. S. Shouval, Y. Krelin, E. Cagnano, D. Benharroch, Y. Iwakura, C. A. Dinarello, R. N. Apte, IL-1 is required for tumor invasiveness and angiogenesis. *Proc NatlAcadSci* USA 100, 2645-2650 (2003).
94. C. J. Creighton, A gene transcription signature associated with hormone independence in a subset of both breast and prostate cancers. *BMC Genomics* 8, 199 (2007).
95. R. Kesselring, J. Glaesner, A. Hiergeist, E. Naschberger, H. Neumann, S. M. Brunner, A. K. Wege, C. Seebauer, G. Kohl, S. Merkl, R. S. Croner, C. Hackl, M. Sturzl, M. F. Neurath, A. Gessner, H. J. Schlitt, E. K. Geissler, S.

Fichtner-Feigl, IRAK-M Expression in Tumor Cells Supports Colorectal Cancer Progression through Reduction of Antimicrobial Defense and Stabilization of STAT3. *Cancer Cell* 29, 684-696 (2016).
96. J. Zhang, Y. Wang, G. Li, H. Yu, X. Xie, Down-regulation of nicotinamide N-methyltransferase induces apoptosis in human breast cancer cells via the mitochondria-mediated pathway. *PLoS One* 9, e89202 (2014).
97. M. Maurer, Z. Trajanoski, G. Frey, N. Hiroi, J. Galon, H. S. Willenberg, P. W. Gold, G. P. Chrousos, W. A. Scherbaum, S. R. Bornstein, Differential gene expression profile of glucocorticoids, testosterone, and dehydroepiandrosterone in human cells. *Horm Metab Res* 33, 691-695 (2001).
98. J. C. Wang, M. K. Derynck, D. F. Nonaka, D. B. Khodabakhsh, C. Haqq, K. R. Yamamoto, Chromatin immunoprecipitation (ChIP) scanning identifies primary glucocorticoid receptor target genes. *Proc Natl AcadSci USA* 101, 15603-15608 (2004).
99. J. Chen, H. K. Kinyamu, T. K. Archer, Changes in attitude, changes in latitude: nuclear receptors remodeling chromatin to regulate transcription. *Mol Endocrinol* 20, 1-13 (2006).
100. J. A. Sparano, R. J. Gray, D. F. Makower, K. I. Pritchard, K. S. Albain, D. F. Hayes, C. E. Geyer, Jr., E. C. Dees, E. A. Perez, J. A. Olson, Jr., J. Zujewski, T. Lively, S. S. Badve, T. J. Saphner, L. I. Wagner, T. J. Whelan, M. J. Ellis, S. Paik, W. C. Wood, P. Ravdin, M. M. Keane, H. L. Gomez Moreno, P. S. Reddy, T. F. Goggins, I. A. Mayer, A. M. Brufsky, D. L. Toppmeyer, V. G. Kaklamani, J. N. Atkins, J. L. Berenberg, G. W. Sledge, Prospective Validation of a 21-Gene Expression Assay in Breast Cancer. *N Engl J Med* 373, 2005-2014 (2015).
101. C. K. Glass, M. G. Rosenfeld, The coregulator exchange in transcriptional functions of nuclear receptors. *Genes Dev* 14, 121-141 (2000).
102. Y. Shang, M. Myers, M. Brown, Formation of the androgen receptor transcription complex. *Mol Cell* 9, 601-610 (2002).
103. I. M. Wolf, M. D. Heitzer, M. Grubisha, D. B. DeFranco, Coactivators and nuclear receptor transactivation. *JCell Biochem* 104, 1580-1586 (2008).
104. K. M. Jozwik, J. S. Carroll, Pioneer factors in hormone-dependent cancers. *Nat Rev Cancer* 12, 381-385 (2012).
105. R. Chodankar, D. Y. Wu, B. J. Schiller, K. R. Yamamoto, M. R. Stallcup, Hic-5 is a transcription coregulator that acts before and/or after glucocorticoid receptor genome occupancy in a gene-selective manner. *Proc Natl Acad Sci USA* 111, 4007-4012 (2014).
106. A. J. Galliher-Beckley, J. G. Williams, J. A. Cidlowski, Ligand-independent phosphorylation of the glucocorticoid receptor integrates cellular stress pathways with nuclear receptor signaling. *Mol Cell Biol* 31, 4663-4675 (2011).
107. K. A. Leehy, T. M. Regan Anderson, A. R. Daniel, C. A. Lange, J. H. Ostrander, Modifications to glucocorticoid and progesterone receptors alter cell fate in breast cancer. *JMol Endocrinol* 56, R99-R114 (2016).
108. J. A. Lefstin, K. R. Yamamoto, Allosteric effects of DNA on transcriptional regulators. *Nature* 392, 885-888 (1998).
109. M. I. Love, M. R. Huska, M. Jurk, R. Schopflin, S. R. Starick, K. Schwahn, S. B. Cooper, K. R. Yamamoto, M. Thomas-Chollier, M. Vingron, S. H. Meijsing, Role of the chromatin landscape and sequence in determining cell type-specific genomic glucocorticoid receptor binding and gene regulation. *Nucleic Acids Res* 45, 1805-1819 (2017).
110. E. R. Weikum, M. T. Knuesel, E. A. Ortlund, K. R. Yamamoto, Glucocorticoid receptor control of transcription: precision and plasticity via allostery. *Nat Rev Mol Cell Biol* 18, 159-174 (2017).
111. J. C. Wang, N. Shah, C. Pantoja, S. H. Meijsing, J. D. Ho, T. S. Scanlan, K. R. Yamamoto, Novel arylpyrazole compounds selectively modulate glucocorticoid receptor regulatory activity. *Genes Dev* 20, 689-699 (2006).
112. R. D. Clark, Glucocorticoid receptor antagonists. *Curr Top Med Chem* 8, 813-838 (2008).
113. A. McMaster, D. W. Ray, Drug insight: selective agonists and antagonists of the glucocorticoid receptor. *Nat Clin PractEndocrinol Metab* 4, 91-101 (2008).
114. B. W. Peeters, G. S. Ruigt, M. Craighead, P. Kitchener, Differential effects of the new glucocorticoid receptor antagonist ORG 34517 and RU486 (mifepristone) on glucocorticoid receptor nuclear translocation in the AtT20 cell line. *Ann N YAcad Sci* 1148, 536-541 (2008).
115. H. J. Hunt, J. K. Belanoff, I. Walters, B. Gourdet, J. Thomas, N. Barton, J. Unitt, T. Phillips, D. Swift, E. Eaton, Identification of the Clinical Candidate (R)-(1-(4-Fluorophenyl)-6-((1-methyl-1H-pyrazol-4-yl)sulfonyl)-4,4a,5,6,7,8-hexah ydro-1H-pyrazolo[3,4-g]isoquinolin-4a-yl)(4-(trifluoromethyl)pyridin-2-yl)methano ne (CORT125134): A Selective Glucocorticoid Receptor (GR) Antagonist. *J Med Chem* 60, 3405-3421 (2017).
116. V. Vichai, K. Kirtikara, Sulforhodamine B colorimetric assay for cytotoxicity screening. *Nat Protoc* 1, 1112-1116 (2006).
117. R. C. Gentleman, V. J. Carey, D. M. Bates, B. Bolstad, M. Dettling, S. Dudoit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. Yang, J. Zhang, Bioconductor: open software development for computational biology and bioinformatics. *Genome Biol* 5, R80 (2004).
118. J. Goecks, A. Nekrutenko, J. Taylor, T. Galaxy, Galaxy: a comprehensive approach for supporting accessible, reproducible, and transparent computational research in the life sciences. *Genome Biol* 11, R86 (2010).
119. F. Ramirez, F. Dundar, S. Diehl, B. A. Gruning, T. Manke, deepTools: a flexible platform for exploring deep-sequencing data. *Nucleic Acids Res* 42, W187-191 (2014).
120. P. Stempor, J. Ahringer, SeqPlots—Interactive software for exploratory data analyses, pattern discovery and visualization in genomics. *Wellcome Open Res* 1, 14 (2016).
121. T. L. Bailey, P. Machanick, Inferring direct DNA binding from ChIP-seq. *Nucleic Acids Res* 40, e128 (2012).
122. G. Yu, L. G. Wang, Q. Y. He, ChIPseeker: an R/Bioconductor package for ChIP peak annotation, comparison and visualization. *Bioinformatics* 31, 2382-2383 (2015).
123. H. Thorvaldsdottir, J. T. Robinson, J. P. Mesirov, Integrative Genomics Viewer (IGV): high-performance genomics data visualization and exploration. *BriefBioinform* 14, 178-192 (2013).
124. A. Biosystems, "Guide to performing relative quantitation of gene expression using real-time quantitative PCR," (2008).
125. A. M. Szasz, A. Lanczky, A. Nagy, S. Forster, K. Hark, J. E. Green, A. Boussioutas, R. Busuttil, A. Szabo, B. Gyorffy, Cross-validation of survival associated biomarkers in gastric cancer using transcriptomic data of 1,065 patients. *Oncotarget* 7, 49322-49333 (2016)

What is claimed is:

1. A method for treating a triple-negative, glucocorticoid receptor (GR) positive breast cancer patient comprising administering a glucocorticoid receptor (GR) inhibitor to the patient after the level of expression for at least 2 genes of ABHD5, ACSL3, APIAR, ASMTL, ATP2B1, B8S10, BCOR, Cl2orf29, CACNAIG, CCT6A, CDK7, CDKN2D, CHMP2B, COL4A6, COL7A1, CORO2B, CPNE6, CRYI, CUL4A, DDX18, DLAT, DLG4, EIF3J, ETF1, F2R, FGF5, GL12, GRM5, GRM6, HEATR3, HOMER1, HPS5, HSPA9, IMPACT, IP07, IQCC, KCTD3, KISS 1, LMNA, LYPLA1, MAPRE2, MAS1, MUC5AC, NAP1L1, NOL11, NOX5, PEX3, PGRMC2, PLCB4, POLO, PRPF39, RABGGTB, RMND1, RPL31, RRH, SCN3B, SEH1L, SERP1, SERPIND1, SLC4A4, SPATA5L1, SSB, SSBP3, SYT1, TBXA2R, TCEB1, TROAP, TSEN2, TYRO3, USEI, UTP14A, WDR43, WNTSA, and ZNF189 has been measured from a biological sample from the patient.

2. A method for measuring the level of gene expression in a triple-negative, glucocorticoid receptor (GR) positive breast cancer patient for GR inhibitor therapy comprising measuring the level of expression of at least 2 genes of ABHD5, ACSL3, APIAR, ASMTL, ATP2B1, B8S10, BCOR, Cl2orf29, CACNAIG, CCT6A, CDK7, CDKN2D, CHMP2B, COL4A6, COL7A1, CORO2B, CPNE6, CRYI, CUL4A, DDX18, DLAT, DLG4, EIF3J, ETF1, F2R, FGF5, GL12, GRM5, GRM6, HEATR3, HOMER1, HPS5, HSPA9, IMPACT, IP07, IQCC, KCTD3, KISS1, LMNA, LYPLAI, MAPRE2, MAS1, MUC5AC, NAP1L1, NOL11, NOX5, PEX3, PGRMC2, PLCB4, POLO, PRPF39, RABGGTB, RMND1, RPL31, RRH, SCN3B, SEH1L, SERP1, SERPIND1, SLC4A4, SPATA5L1, SSB, SSBP3, SYT1, TBXA2R, TCEB1, TROAP, TSEN2, TYRO3, USEI, UTP14A, WDR43, WNTSA, and ZNF 189 in a biological sample from the breast cancer patient and comparing the levels to a control level.

3. The method of claim 2, wherein the level of expression of at least 5 genes on Table S2 has been measured in a sample from the patient.

4. The method of claim 3, wherein the level of expression of at least 10 genes is measured in a sample from the patient.

5. The method of claim 4, wherein the level of expression of at least 20 genes is been measured in a sample from the patient.

6. The method of claim 5, wherein the level of expression of at least 40 genes is measured in a sample from the patient.

7. The method of claim 6, wherein the level of expression of 74 genes is measured in a sample from the patient.

8. The method of claim 2, wherein one or more control levels are altered expression levels from a control that is a GR antagonist-reversible transcriptional target.

9. The method of claim 2, wherein one or more control levels are unaffected expression levels from a GR antagonist-reversible transcriptional target.

10. The method of claim 9, wherein the level of expression of at least ETF1 and SSB are increased compared to the control.

11. The method of claim 9, wherein the level of expression of at least two genes is decreased compared to the control.

12. The method of claim 11, wherein the at least two genes are CACNAIG, CDKN2D, COL4A6, COL7A1, CORO2B, CPNE6, DLG4, FGF5, GI12, GRM5, GRM6, IQCC, KISS1, LMNA, MAPRE2, MAS1, MUCSAC, NOXS, POLQ, RRH, SCN3B, SERPIND1, SLC4A4, SSBP3, SYT1, TBXA2R, TROAP, and/or TYRO3.

13. The method of claim 8, wherein the level of expression of at least two genes is equivalent to the control level.

14. The method of claim 2, wherein the patient has not been administered dexamethasone.

15. The method of claim 2, wherein the patient's sample is determined to have a level of GR transcription that is higher than a median or average level of GR expression levels in breast cancer cells.

* * * * *